(12) United States Patent
Bossio et al.

(10) Patent No.: US 10,818,387 B2
(45) Date of Patent: Oct. 27, 2020

(54) DOSE PREPARATION DATA ANALYTICS

(71) Applicant: Baxter Corporation Englewood, Englewood, CO (US)

(72) Inventors: Robert Joseph Bossio, Palm Coast, FL (US); Bhavesh S. Padmani, Port Orange, FL (US); Matthew A. Valentine, Ormond Beach, FL (US)

(73) Assignee: Baxter Corporation Englewood, Englewood, CO (US)

( * ) Notice: Subject to any disclaimer, the term of this patent is extended or adjusted under 35 U.S.C. 154(b) by 899 days.

(21) Appl. No.: 14/957,819

(22) Filed: Dec. 3, 2015

(65) Prior Publication Data

US 2016/0180057 A1 Jun. 23, 2016

Related U.S. Application Data

(60) Provisional application No. 62/088,358, filed on Dec. 5, 2014.

(51) Int. Cl.
*G16H 15/00* (2018.01)
*G16H 40/20* (2018.01)
*G16H 20/10* (2018.01)

(52) U.S. Cl.
CPC .............. *G16H 15/00* (2018.01); *G16H 20/10* (2018.01); *G16H 40/20* (2018.01)

(58) Field of Classification Search
CPC ........ G16H 10/60; G16H 20/10; G16H 50/70; G16H 70/40; G16H 15/00; G16H 40/20
See application file for complete search history.

(56) References Cited

U.S. PATENT DOCUMENTS

| 641,748 | A | 1/1900 | Smith |
| 819,339 | A | 5/1906 | Cleland |
| 3,426,150 | A | 2/1969 | Tygart |

(Continued)

FOREIGN PATENT DOCUMENTS

| CN | 1516257 | 5/1999 |
| CN | 2440518 | 8/2001 |

(Continued)

OTHER PUBLICATIONS

Extended European Search Report (EESR) dated Jun. 11, 2018 in corresponding EP Application No. 15865852.6; (10 Pages).

(Continued)

*Primary Examiner* — John P Go
(74) *Attorney, Agent, or Firm* — K&L Gates LLP

(57) ABSTRACT

Providing selective, secure access to an aggregated, multi-dimensional data set comprising dose order records for generation of data analytics with respect thereto. The aggregated data may correspond to a plurality of unaffiliated facilities. As such, upon a user from a given facility attempting to access a data analytics tool may be identified in relation to a facility from which the user is accessing the tool. In turn, a data cube class definition from which all other data analytics data cubes inherit from may be used to, in conjunction with the user identification, limit the data used to generate data analytics outputs to source data to which the user has authorization to view. The outputs may include including, for example, reports, dashboards, tables, or the like.

22 Claims, 11 Drawing Sheets

(56) References Cited

U.S. PATENT DOCUMENTS

| | | |
|---|---|---|
| 3,739,943 A | 6/1973 | Williamsen et al. |
| 3,742,938 A | 7/1973 | Stern |
| 3,756,752 A | 9/1973 | Stenner |
| 3,774,762 A | 11/1973 | Lichtenstein |
| 3,786,190 A | 1/1974 | Pori |
| 3,809,871 A | 5/1974 | Howard et al. |
| 3,810,102 A | 5/1974 | Parks, III et al. |
| 3,848,112 A | 11/1974 | Weichselbaum et al. |
| 3,858,574 A | 1/1975 | Page |
| 3,878,967 A | 4/1975 | Joslin et al. |
| 3,910,257 A | 10/1975 | Fletcher et al. |
| 3,910,260 A | 10/1975 | Sarnoff et al. |
| 3,921,196 A | 11/1975 | Patterson |
| 3,971,000 A | 7/1976 | Cromwell |
| 3,995,630 A | 12/1976 | Verrdonk |
| 3,998,103 A | 12/1976 | Bjorklund et al. |
| 4,032,908 A | 6/1977 | Rice et al. |
| 4,078,562 A | 3/1978 | Friedman |
| 4,144,496 A | 3/1979 | Cunningham et al. |
| 4,151,407 A | 4/1979 | McBride et al. |
| 4,156,867 A | 5/1979 | Bench et al. |
| 4,164,320 A | 8/1979 | Irazoqui et al. |
| 4,173,971 A | 11/1979 | Karz |
| 4,199,307 A | 4/1980 | Jassawalla |
| 4,270,532 A | 6/1981 | Franetzki et al. |
| 4,273,121 A | 6/1981 | Jassawalla |
| 4,282,872 A | 8/1981 | Franetzki et al. |
| 4,308,866 A | 1/1982 | Jelliffe et al. |
| 4,319,338 A | 3/1982 | Grudowski et al. |
| 4,320,757 A | 3/1982 | Whitney et al. |
| 4,354,252 A | 10/1982 | Lamb et al. |
| 4,369,780 A | 1/1983 | Sakai |
| 4,370,983 A | 2/1983 | Lichtenstein |
| 4,373,527 A | 2/1983 | Fischell |
| 4,381,776 A | 5/1983 | Latham, Jr. |
| 4,385,630 A | 5/1983 | Gilcher et al. |
| 4,398,289 A | 8/1983 | Schoate |
| 4,398,908 A | 8/1983 | Siposs |
| 4,414,566 A | 11/1983 | Peyton et al. |
| 4,416,654 A | 11/1983 | Schoendorfer et al. |
| 4,425,114 A | 1/1984 | Schoendorfer et al. |
| 4,428,381 A | 1/1984 | Hepp |
| 4,443,216 A | 4/1984 | Chappell |
| 4,447,224 A | 5/1984 | Decant, Jr. et al. |
| 4,449,538 A | 5/1984 | Corbitt et al. |
| 4,451,255 A | 5/1984 | Bujan et al. |
| 4,457,750 A | 7/1984 | Hill |
| 4,458,693 A | 7/1984 | Badzinski et al. |
| 4,460,358 A | 7/1984 | Somerville et al. |
| 4,464,172 A | 8/1984 | Lichtenstein |
| 4,469,481 A | 9/1984 | Kobayashi |
| 4,475,901 A | 10/1984 | Kraegen et al. |
| 4,476,381 A | 10/1984 | Rubin |
| 4,480,751 A | 11/1984 | Lueptow |
| 4,481,670 A | 11/1984 | Freeburg |
| 4,487,604 A | 12/1984 | Iwatschenko et al. |
| 4,490,798 A | 12/1984 | Franks et al. |
| 4,496,351 A | 1/1985 | Hillel et al. |
| 4,511,352 A | 4/1985 | Theeuwes et al. |
| 4,525,861 A | 6/1985 | Freeburg |
| 4,526,574 A | 7/1985 | Pekkarinen |
| 4,529,401 A | 7/1985 | Leslie et al. |
| 4,531,527 A | 7/1985 | Reinhold, Jr. et al. |
| 4,538,138 A | 8/1985 | Harvey et al. |
| 4,545,071 A | 10/1985 | Freeburg |
| 4,551,133 A | 11/1985 | Zegers de Beyl et al. |
| 4,559,038 A | 12/1985 | Berg et al. |
| 4,560,979 A | 12/1985 | Rosskopf |
| 4,561,443 A | 12/1985 | Hogrefe et al. |
| 4,562,751 A | 1/1986 | Nason |
| 4,564,054 A | 1/1986 | Gustavsson |
| 4,590,473 A | 5/1986 | Burke et al. |
| 4,602,249 A | 7/1986 | Abbott |
| 4,619,653 A | 10/1986 | Fischell |
| 4,622,979 A | 11/1986 | Katchis et al. |
| 4,624,661 A | 11/1986 | Arimond |
| 4,636,950 A | 1/1987 | Caswell et al. |
| 4,637,817 A | 1/1987 | Archibald et al. |
| 4,650,469 A | 3/1987 | Berg et al. |
| 4,652,262 A | 3/1987 | Veracchi |
| 4,653,010 A | 3/1987 | Figler et al. |
| 4,676,776 A | 6/1987 | Howson |
| 4,681,563 A | 7/1987 | Deckert et al. |
| 4,688,167 A | 8/1987 | Agarwal |
| 4,691,580 A | 9/1987 | Fosslien |
| 4,695,954 A | 9/1987 | Rose et al. |
| 4,696,671 A | 9/1987 | Epstein et al. |
| 4,697,928 A | 10/1987 | Csongor |
| 4,702,595 A | 10/1987 | Mutschler et al. |
| 4,705,506 A | 11/1987 | Archibald |
| D293,135 S | 12/1987 | Medema et al. |
| 4,714,462 A | 12/1987 | DiComenico |
| 4,717,042 A | 1/1988 | McLaughlin |
| 4,718,576 A | 1/1988 | Tamura et al. |
| 4,722,224 A | 2/1988 | Scheller et al. |
| 4,722,349 A | 2/1988 | Baumberg |
| 4,722,734 A | 2/1988 | Kolln |
| 4,730,849 A | 3/1988 | Siegel |
| 4,731,058 A | 3/1988 | Doan |
| 4,732,411 A | 3/1988 | Siegel |
| 4,741,732 A | 5/1988 | Crankshaw et al. |
| 4,741,736 A | 5/1988 | Brown |
| 4,756,706 A | 7/1988 | Kerns et al. |
| 4,759,756 A | 7/1988 | Forman |
| 4,770,184 A | 9/1988 | Greene et al. |
| 4,778,449 A | 10/1988 | Weber et al. |
| 4,779,626 A | 10/1988 | Peel et al. |
| 4,784,645 A | 11/1988 | Fischell |
| 4,785,799 A | 11/1988 | Schoon et al. |
| 4,785,969 A | 11/1988 | McLaughlin |
| 4,796,644 A | 1/1989 | Polaschegg |
| 4,797,840 A | 1/1989 | Fraden |
| 4,803,625 A | 2/1989 | Fu et al. |
| 4,810,090 A | 3/1989 | Boucher |
| 4,810,243 A | 3/1989 | Howson |
| 4,811,844 A | 3/1989 | Moulding, Jr. et al. |
| 4,816,208 A | 3/1989 | Woods et al. |
| 4,817,044 A | 3/1989 | Ogren |
| 4,828,545 A | 5/1989 | Epstein et al. |
| 4,829,524 A | 5/1989 | Yoshida |
| 4,830,018 A | 5/1989 | Treach |
| 4,831,562 A | 5/1989 | Mcintosh et al. |
| 4,832,033 A | 5/1989 | Maher et al. |
| 4,835,372 A | 5/1989 | Gombrich et al. |
| 4,835,521 A | 5/1989 | Andrejasich et al. |
| 4,838,275 A | 6/1989 | Lee |
| 4,839,806 A | 6/1989 | Goldfischer et al. |
| 4,845,644 A | 7/1989 | Anthias et al. |
| 4,847,764 A | 7/1989 | Halvorson |
| 4,850,009 A | 7/1989 | Zook et al. |
| 4,850,972 A | 7/1989 | Schulman et al. |
| 4,853,521 A | 8/1989 | Claeys et al. |
| 4,854,324 A | 8/1989 | Hirschman et al. |
| 4,857,713 A | 8/1989 | Brown |
| 4,857,716 A | 8/1989 | Gombrich et al. |
| 4,865,584 A | 9/1989 | Epstein et al. |
| 4,871,351 A | 10/1989 | Feingold |
| 4,878,175 A | 10/1989 | Norden-Paul et al. |
| 4,880,013 A | 11/1989 | Chio |
| 4,889,132 A | 12/1989 | Hutcheson et al. |
| 4,889,134 A | 12/1989 | Greenwold et al. |
| 4,893,270 A | 1/1990 | Beck et al. |
| 4,897,777 A | 1/1990 | Janke et al. |
| 4,898,209 A | 2/1990 | Zbed |
| 4,898,576 A | 2/1990 | Philip |
| 4,898,578 A | 2/1990 | Rubalcaba, Jr. |
| 4,901,728 A | 2/1990 | Hutchison |
| 4,905,163 A | 2/1990 | Garber et al. |
| 4,908,017 A | 3/1990 | Howson et al. |
| 4,912,623 A | 3/1990 | Rantala et al. |
| 4,916,441 A | 4/1990 | Gombrich et al. |
| 4,922,922 A | 5/1990 | Pollock et al. |
| 4,925,444 A | 5/1990 | Orkin et al. |
| 4,933,843 A | 6/1990 | Scheller et al. |

(56) References Cited

U.S. PATENT DOCUMENTS

| | | |
|---|---|---|
| 4,937,777 A | 6/1990 | Flood et al. |
| 4,941,808 A | 7/1990 | Qureshi et al. |
| 4,943,279 A | 7/1990 | Samiotes et al. |
| 4,943,987 A | 7/1990 | Asahina et al. |
| 4,946,445 A | 8/1990 | Lynn |
| 4,949,274 A | 8/1990 | Hollander et al. |
| 4,952,928 A | 8/1990 | Carroll et al. |
| 4,953,074 A | 8/1990 | Kametani et al. |
| 4,960,230 A | 10/1990 | Marelli |
| 4,964,847 A | 10/1990 | Prince |
| 4,966,579 A | 10/1990 | Polaschegg |
| 4,967,928 A | 11/1990 | Carter |
| 4,968,295 A | 11/1990 | Neumann |
| 4,975,647 A | 12/1990 | Downer et al. |
| 4,977,590 A | 12/1990 | Milovancevic |
| 4,978,335 A | 12/1990 | Arthur, III |
| 4,991,091 A | 2/1991 | Allen |
| 4,992,926 A | 2/1991 | Janke et al. |
| 4,993,068 A | 2/1991 | Piosenka et al. |
| 4,993,506 A | 2/1991 | Angel |
| 4,998,249 A | 3/1991 | Bennett et al. |
| 5,002,055 A | 3/1991 | Merki et al. |
| 5,003,296 A | 3/1991 | Lee |
| 5,006,699 A | 4/1991 | Felkner et al. |
| 5,007,429 A | 4/1991 | Treatch et al. |
| 5,012,402 A | 4/1991 | Akiyama |
| 5,012,411 A | 4/1991 | Policastro et al. |
| 5,014,875 A | 5/1991 | McLaughlin et al. |
| 5,016,172 A | 5/1991 | Dessertine |
| 5,023,770 A | 6/1991 | Siverling |
| 5,025,374 A | 6/1991 | Roizen et al. |
| 5,036,852 A | 8/1991 | Leishman |
| 5,038,800 A | 8/1991 | Oba |
| 5,041,086 A | 8/1991 | Koenig et al. |
| 5,045,048 A | 9/1991 | Kaleskas et al. |
| 5,047,959 A | 9/1991 | Phillips et al. |
| 5,053,031 A | 10/1991 | Borsanyi |
| 5,053,990 A | 10/1991 | Kreifels et al. |
| 5,055,001 A | 10/1991 | Natwick et al. |
| 5,057,076 A | 10/1991 | Polaschegg |
| 5,061,243 A | 10/1991 | Winchell et al. |
| 5,072,356 A | 12/1991 | Watt et al. |
| 5,072,383 A | 12/1991 | Brimm et al. |
| 5,072,412 A | 12/1991 | Henderson, Jr. et al. |
| 5,078,683 A | 1/1992 | Sancoff et al. |
| 5,084,828 A | 1/1992 | Kaufman et al. |
| 5,087,245 A | 2/1992 | Doan |
| 5,088,904 A | 2/1992 | Okada |
| 5,088,981 A | 2/1992 | Howson et al. |
| 5,088,990 A | 2/1992 | Hivale et al. |
| 5,096,385 A | 3/1992 | Georgi et al. |
| 5,098,377 A | 3/1992 | Borsanyi et al. |
| 5,100,380 A | 3/1992 | Epstein et al. |
| 5,100,394 A | 3/1992 | Dudar et al. |
| 5,103,211 A | 4/1992 | Daoud et al. |
| 5,104,374 A | 4/1992 | Bishko et al. |
| 5,108,131 A | 4/1992 | Nassim |
| 5,108,363 A | 4/1992 | Tuttle et al. |
| 5,108,367 A | 4/1992 | Epstein et al. |
| 5,108,372 A | 4/1992 | Swenson |
| 5,109,487 A | 4/1992 | Ohgomori et al. |
| 5,109,849 A | 5/1992 | Goodman et al. |
| 5,112,319 A | 5/1992 | Lai |
| 5,116,203 A | 5/1992 | Natwick et al. |
| 5,116,312 A | 5/1992 | Blankenship et al. |
| 5,131,092 A | 7/1992 | Sackmann et al. |
| 5,134,574 A | 7/1992 | Beaverstock et al. |
| 5,135,500 A | 8/1992 | Zdeb |
| 5,137,023 A | 8/1992 | Mendelson et al. |
| 5,151,978 A | 9/1992 | Bronikowski et al. |
| 5,152,296 A | 10/1992 | Simons |
| 5,153,416 A | 10/1992 | Neeley |
| 5,153,827 A | 10/1992 | Coutre et al. |
| 5,155,693 A | 10/1992 | Altmayer et al. |
| 5,157,595 A | 10/1992 | Lovrenich |
| 5,158,091 A | 10/1992 | Butterfield et al. |
| 5,159,673 A | 10/1992 | Sackmann et al. |
| 5,160,320 A | 11/1992 | Yum et al. |
| 5,161,211 A | 11/1992 | Taguchi et al. |
| 5,167,235 A | 12/1992 | Seacord et al. |
| 5,169,642 A | 12/1992 | Brinker et al. |
| 5,172,698 A | 12/1992 | Stanko |
| 5,176,004 A | 1/1993 | Gaudet |
| 5,179,569 A | 1/1993 | Sawyer |
| 5,179,700 A | 1/1993 | Aihara et al. |
| 5,181,910 A | 1/1993 | Scanlon |
| 5,190,185 A | 3/1993 | Blechl |
| 5,190,522 A | 3/1993 | Wojcicki et al. |
| 5,191,891 A | 3/1993 | Righter |
| 5,208,762 A | 5/1993 | Charhut et al. |
| 5,208,907 A | 5/1993 | Shelton et al. |
| 5,211,849 A | 5/1993 | Kitaevich et al. |
| 5,213,099 A | 5/1993 | Tripp, Jr. |
| 5,213,232 A | 5/1993 | Kraft et al. |
| 5,213,568 A | 5/1993 | Lattin et al. |
| 5,219,330 A | 6/1993 | Bollish et al. |
| 5,219,331 A | 6/1993 | Vanderveen |
| 5,225,974 A | 7/1993 | Mathews et al. |
| 5,226,425 A | 7/1993 | Righter |
| 5,228,450 A | 7/1993 | Sellers |
| 5,231,990 A | 8/1993 | Gauglitz |
| 5,234,404 A | 8/1993 | Tuttle et al. |
| 5,235,510 A | 8/1993 | Yamada et al. |
| 5,236,416 A | 8/1993 | McDaniel et al. |
| 5,238,001 A | 8/1993 | Gallant et al. |
| 5,240,007 A | 8/1993 | Pytel et al. |
| 5,244,463 A | 9/1993 | Cordner, Jr. et al. |
| 5,245,704 A | 9/1993 | Weber et al. |
| 5,254,096 A | 10/1993 | Rondelet et al. |
| 5,256,156 A | 10/1993 | Kern et al. |
| 5,256,157 A | 10/1993 | Samiotes et al. |
| 5,261,884 A | 11/1993 | Stern et al. |
| 5,262,943 A | 11/1993 | Thibado et al. |
| 5,265,010 A | 11/1993 | Evans-Paganelli et al. |
| 5,265,431 A | 11/1993 | Gaudet et al. |
| 5,267,174 A | 11/1993 | Kaufman et al. |
| 5,271,405 A | 12/1993 | Boyer et al. |
| 5,272,318 A | 12/1993 | Gorman |
| 5,272,321 A | 12/1993 | Otsuka et al. |
| 5,273,517 A | 12/1993 | Barone et al. |
| 5,277,188 A | 1/1994 | Selker |
| 5,283,861 A | 2/1994 | Dangler et al. |
| 5,284,150 A | 2/1994 | Butterfield et al. |
| 5,286,252 A | 2/1994 | Tuttle et al. |
| 5,292,029 A | 3/1994 | Pearson |
| 5,297,257 A | 3/1994 | Struger et al. |
| 5,298,021 A | 3/1994 | Sherer |
| 5,304,126 A | 4/1994 | Epstein et al. |
| 5,307,263 A | 4/1994 | Brown |
| 5,307,372 A | 4/1994 | Sawyer et al. |
| 5,307,463 A | 4/1994 | Hyatt et al. |
| 5,311,908 A | 5/1994 | Barone et al. |
| 5,314,243 A | 5/1994 | McDonald et al. |
| 5,315,505 A | 5/1994 | Pratt et al. |
| 5,317,506 A | 5/1994 | Coutre et al. |
| 5,319,363 A | 6/1994 | Welch et al. |
| 5,319,543 A | 6/1994 | Wilhelm |
| 5,321,618 A | 6/1994 | Gessman |
| 5,321,829 A | 6/1994 | Zifferer |
| 5,324,422 A | 6/1994 | Colleran et al. |
| 5,325,478 A | 6/1994 | Shelton et al. |
| 5,327,341 A | 7/1994 | Whalen et al. |
| 5,331,549 A | 7/1994 | Crawford, Jr. |
| 5,336,245 A | 8/1994 | Adams et al. |
| 5,337,230 A | 8/1994 | Baumgartner et al. |
| 5,337,747 A | 8/1994 | Neftel |
| 5,337,919 A | 8/1994 | Spaulding et al. |
| 5,338,157 A | 8/1994 | Blomquist |
| 5,339,421 A | 8/1994 | Housel, III |
| 5,339,821 A | 8/1994 | Fujimoto |
| 5,341,291 A | 8/1994 | Roizen et al. |
| 5,341,412 A | 8/1994 | Ramot et al. |
| 5,348,008 A | 9/1994 | Bornn et al. |
| 5,348,539 A | 9/1994 | Herskowitz |

(56) References Cited

U.S. PATENT DOCUMENTS

| | | |
|---|---|---|
| 5,349,675 A | 9/1994 | Fitzgerald et al. |
| 5,356,378 A | 10/1994 | Doan |
| 5,360,410 A | 11/1994 | Wacks |
| 5,361,202 A | 11/1994 | Doue |
| 5,361,758 A | 11/1994 | Hall et al. |
| 5,366,896 A | 11/1994 | Margrey et al. |
| 5,366,904 A | 11/1994 | Qureshi et al. |
| 5,367,555 A | 11/1994 | Isoyama |
| 5,368,562 A | 11/1994 | Blomquist et al. |
| 5,370,612 A | 12/1994 | Maeda et al. |
| 5,371,687 A | 12/1994 | Holmes, II et al. |
| 5,374,251 A | 12/1994 | Smith |
| 5,374,813 A | 12/1994 | Shipp |
| 5,374,965 A | 12/1994 | Kanno |
| 5,375,604 A | 12/1994 | Kelly et al. |
| 5,376,070 A | 12/1994 | Purvis et al. |
| 5,377,864 A | 1/1995 | Blechl et al. |
| 5,378,231 A | 1/1995 | Johnson et al. |
| 5,379,214 A | 1/1995 | Arbuckle et al. |
| 5,389,078 A | 2/1995 | Zalesky et al. |
| 5,390,238 A | 2/1995 | Kirk et al. |
| 5,392,951 A | 2/1995 | Gardner et al. |
| 5,395,320 A | 3/1995 | Padda et al. |
| 5,395,321 A | 3/1995 | Kawahara et al. |
| 5,398,336 A | 3/1995 | Tantry et al. |
| 5,401,059 A | 3/1995 | Ferrario |
| 5,404,292 A | 4/1995 | Hendrickson |
| 5,404,384 A | 4/1995 | Colburn et al. |
| 5,406,473 A | 4/1995 | Yoshikura et al. |
| 5,412,715 A | 5/1995 | Volpe |
| 5,415,167 A | 5/1995 | Wilk |
| 5,416,695 A | 5/1995 | Stutman et al. |
| 5,417,222 A | 5/1995 | Dempsey et al. |
| 5,420,977 A | 5/1995 | Sztipanovits et al. |
| 5,421,343 A | 6/1995 | Feng |
| 5,423,746 A | 6/1995 | Burkett et al. |
| 5,429,602 A | 7/1995 | Hauser |
| 5,431,201 A | 7/1995 | Torchia et al. |
| 5,431,299 A | 7/1995 | Brewer et al. |
| 5,431,627 A | 7/1995 | Pastrone et al. |
| 5,433,736 A | 7/1995 | Nilsson |
| 5,438,607 A | 8/1995 | Przygoda, Jr. et al. |
| 5,440,699 A | 8/1995 | Farrand et al. |
| 5,441,047 A | 8/1995 | David et al. |
| 5,445,294 A | 8/1995 | Gardner et al. |
| 5,445,621 A | 8/1995 | Poli et al. |
| 5,446,868 A | 8/1995 | Gardea, II et al. |
| 5,453,098 A | 9/1995 | Botts et al. |
| 5,455,851 A | 10/1995 | Chaco et al. |
| 5,458,123 A | 10/1995 | Unger |
| 5,460,294 A | 10/1995 | Williams |
| 5,460,605 A | 10/1995 | Tuttle et al. |
| 5,461,665 A | 10/1995 | Shur et al. |
| 5,462,051 A | 10/1995 | Oka et al. |
| 5,464,392 A | 11/1995 | Epstein et al. |
| 5,465,286 A | 11/1995 | Clare et al. |
| 5,467,773 A | 11/1995 | Bergelson et al. |
| 5,468,110 A | 11/1995 | McDonald et al. |
| 5,469,855 A | 11/1995 | Pompei et al. |
| 5,471,382 A | 11/1995 | Tallman et al. |
| 5,474,552 A | 12/1995 | Palti |
| 5,482,043 A | 1/1996 | Zulauf |
| 5,482,446 A | 1/1996 | Williamson et al. |
| 5,485,408 A | 1/1996 | Blomquist |
| 5,490,610 A | 2/1996 | Pearson |
| 5,494,592 A | 2/1996 | Latham, Jr. et al. |
| 5,496,265 A | 3/1996 | Langley et al. |
| 5,496,273 A | 3/1996 | Pastrone et al. |
| 5,502,944 A | 4/1996 | Kraft et al. |
| 5,507,412 A | 4/1996 | Ebert et al. |
| 5,508,912 A | 4/1996 | Schneiderman |
| 5,509,318 A | 4/1996 | Gomes |
| 5,509,422 A | 4/1996 | Fukami |
| 5,513,957 A | 5/1996 | O'Leary |
| 5,514,088 A | 5/1996 | Zakko |
| 5,514,095 A | 5/1996 | Brightbill et al. |
| 5,515,426 A | 5/1996 | Yacenda et al. |
| 5,520,450 A | 5/1996 | Colson, Jr. et al. |
| 5,520,637 A | 5/1996 | Pager et al. |
| 5,522,396 A | 6/1996 | Langer et al. |
| 5,522,798 A | 6/1996 | Johnson et al. |
| 5,526,428 A | 6/1996 | Arnold |
| 5,528,503 A | 6/1996 | Moore et al. |
| 5,529,063 A | 6/1996 | Hill |
| 5,531,680 A | 7/1996 | Dumas et al. |
| 5,531,697 A | 7/1996 | Olsen et al. |
| 5,531,698 A | 7/1996 | Olsen |
| 5,533,079 A | 7/1996 | Colburn et al. |
| 5,533,981 A | 7/1996 | Mandro et al. |
| 5,534,691 A | 7/1996 | Holdaway et al. |
| 5,536,084 A | 7/1996 | Curtis et al. |
| 5,537,313 A | 7/1996 | Pirelli |
| 5,537,853 A | 7/1996 | Finburgh et al. |
| 5,542,420 A | 8/1996 | Goldman et al. |
| 5,544,649 A | 8/1996 | David et al. |
| 5,544,651 A | 8/1996 | Wilk |
| 5,544,661 A | 8/1996 | Davis et al. |
| 5,545,140 A | 8/1996 | Conero et al. |
| 5,546,580 A | 8/1996 | Seliger et al. |
| 5,547,470 A | 8/1996 | Johnson et al. |
| 5,549,117 A | 8/1996 | Tacklind et al. |
| 5,549,460 A | 8/1996 | O'Leary |
| 5,553,609 A | 9/1996 | Chen et al. |
| 5,558,638 A | 9/1996 | Evers et al. |
| 5,558,640 A | 9/1996 | Pfeiler et al. |
| 5,560,352 A | 10/1996 | Heim et al. |
| 5,562,232 A | 10/1996 | Pearson |
| 5,562,621 A | 10/1996 | Claude et al. |
| 5,563,347 A | 10/1996 | Martin et al. |
| 5,564,434 A | 10/1996 | Halperin et al. |
| 5,564,803 A | 10/1996 | McDonald et al. |
| 5,568,912 A | 10/1996 | Minami et al. |
| 5,569,186 A | 10/1996 | Lord et al. |
| 5,569,187 A | 10/1996 | Kaiser |
| 5,571,258 A | 11/1996 | Pearson |
| 5,573,502 A | 11/1996 | LeCocq et al. |
| 5,573,506 A | 11/1996 | Vasko |
| 5,575,632 A | 11/1996 | Morris et al. |
| 5,576,952 A | 11/1996 | Stutman et al. |
| 5,579,001 A | 11/1996 | Dempsey et al. |
| 5,579,378 A | 11/1996 | Arlinghaus, Jr. |
| 5,581,369 A | 12/1996 | Righter et al. |
| 5,581,687 A | 12/1996 | Lyle et al. |
| 5,582,593 A | 12/1996 | Hultman |
| 5,583,758 A | 12/1996 | Mcilroy et al. |
| 5,588,815 A | 12/1996 | Zaleski, II |
| 5,589,932 A | 12/1996 | Garcia-Rubio et al. |
| 5,590,648 A | 1/1997 | Mitchell et al. |
| 5,591,344 A | 1/1997 | Kenley et al. |
| 5,593,267 A | 1/1997 | McDonald et al. |
| 5,594,637 A | 1/1997 | Eisenberg et al. |
| 5,594,786 A | 1/1997 | Chaco et al. |
| 5,597,995 A | 1/1997 | Williams et al. |
| 5,598,536 A | 1/1997 | Slaughter, III et al. |
| 5,601,445 A | 2/1997 | Schipper et al. |
| 5,609,575 A | 3/1997 | Larson et al. |
| 5,609,576 A | 3/1997 | Voss et al. |
| 5,613,115 A | 3/1997 | Gihl et al. |
| 5,619,428 A | 4/1997 | Lee et al. |
| 5,619,991 A | 4/1997 | Sloane |
| 5,623,652 A | 4/1997 | Vora et al. |
| 5,623,925 A | 4/1997 | Swenson et al. |
| 5,626,144 A | 5/1997 | Tacklind et al. |
| 5,628,619 A | 5/1997 | Wilson |
| 5,630,710 A | 5/1997 | Tune et al. |
| 5,631,844 A | 5/1997 | Margrey et al. |
| 5,633,910 A | 5/1997 | Cohen |
| D380,260 S | 6/1997 | Hyman |
| 5,634,893 A | 6/1997 | Rishton |
| 5,637,082 A | 6/1997 | Pages et al. |
| 5,637,093 A | 6/1997 | Hyman et al. |
| 5,640,301 A | 6/1997 | Roecher et al. |
| 5,640,953 A | 6/1997 | Bishop et al. |
| 5,641,628 A | 6/1997 | Bianchi |

(56) References Cited

U.S. PATENT DOCUMENTS

| | | |
|---|---|---|
| 5,643,193 A | 7/1997 | Papillon et al. |
| 5,643,212 A | 7/1997 | Coutre et al. |
| 5,647,853 A | 7/1997 | Feldmann et al. |
| 5,647,854 A | 7/1997 | Olsen et al. |
| 5,651,775 A | 7/1997 | Walker et al. |
| 5,652,566 A | 7/1997 | Lambert |
| 5,658,240 A | 8/1997 | Urdahl et al. |
| 5,658,250 A | 8/1997 | Blomquist et al. |
| 5,661,978 A | 9/1997 | Holmes et al. |
| 5,664,270 A | 9/1997 | Bell et al. |
| 5,666,404 A | 9/1997 | Ciccotelli et al. |
| D385,646 S | 10/1997 | Chan |
| 5,678,562 A | 10/1997 | Sellers |
| 5,678,568 A | 10/1997 | Uchikubo et al. |
| 5,681,285 A | 10/1997 | Ford et al. |
| 5,682,526 A | 10/1997 | Smokoff et al. |
| 5,683,367 A | 11/1997 | Jordan et al. |
| 5,685,844 A | 11/1997 | Marttila |
| 5,687,717 A | 11/1997 | Halpern |
| 5,687,734 A | 11/1997 | Dempsey et al. |
| 5,695,473 A | 12/1997 | Olsen |
| 5,697,951 A | 12/1997 | Harpstead |
| 5,700,998 A | 12/1997 | Palti |
| 5,701,894 A | 12/1997 | Cherry et al. |
| 5,704,351 A | 1/1998 | Mortara et al. |
| 5,704,364 A | 1/1998 | Saltzstein et al. |
| 5,704,366 A | 1/1998 | Tacklind et al. |
| 5,712,798 A | 1/1998 | Langley et al. |
| 5,712,912 A | 1/1998 | Tomko et al. |
| 5,713,485 A | 2/1998 | Liff et al. |
| 5,713,856 A | 2/1998 | Eggers et al. |
| 5,715,823 A | 2/1998 | Wood et al. |
| 5,716,114 A | 2/1998 | Holmes et al. |
| 5,716,194 A | 2/1998 | Butterfield et al. |
| 5,718,562 A | 2/1998 | Lawless et al. |
| 5,719,761 A | 2/1998 | Gatti et al. |
| RE35,743 E | 3/1998 | Pearson |
| 5,724,025 A | 3/1998 | Tavori |
| 5,724,580 A | 3/1998 | Levin et al. |
| 5,732,709 A | 3/1998 | Tacklind et al. |
| 5,733,259 A | 3/1998 | Valcke et al. |
| 5,735,887 A | 4/1998 | Barreras, Sr. et al. |
| 5,737,539 A | 4/1998 | Edelson et al. |
| 5,740,185 A | 4/1998 | Bosse |
| 5,740,800 A | 4/1998 | Hendrickson et al. |
| 5,745,366 A | 4/1998 | Higham et al. |
| 5,745,378 A | 4/1998 | Barker et al. |
| 5,752,917 A | 5/1998 | Fuchs |
| 5,752,976 A | 5/1998 | Duffin et al. |
| 5,755,563 A | 5/1998 | Clegg et al. |
| 5,758,095 A | 5/1998 | Albaum et al. |
| 5,764,923 A | 6/1998 | Tallman et al. |
| 5,766,155 A | 6/1998 | Hyman et al. |
| 5,769,811 A | 6/1998 | Stacey et al. |
| 5,771,657 A | 6/1998 | Lasher et al. |
| 5,772,585 A | 6/1998 | Lavin et al. |
| 5,772,586 A | 6/1998 | Heinonen et al. |
| 5,772,635 A | 6/1998 | Dastur et al. |
| 5,772,637 A | 6/1998 | Heinzmann et al. |
| 5,776,057 A | 7/1998 | Swenson et al. |
| 5,778,345 A | 7/1998 | McCartney |
| 5,778,882 A | 7/1998 | Raymond et al. |
| 5,781,442 A | 7/1998 | Engleson et al. |
| 5,782,805 A | 7/1998 | Meinzer et al. |
| 5,782,878 A | 7/1998 | Morgan et al. |
| 5,785,650 A | 7/1998 | Akasaka et al. |
| 5,788,669 A | 8/1998 | Peterson |
| 5,788,851 A | 8/1998 | Kenley et al. |
| 5,790,409 A | 8/1998 | Fedor et al. |
| 5,791,342 A | 8/1998 | Woodard |
| 5,791,880 A | 8/1998 | Wilson |
| 5,793,861 A | 8/1998 | Haigh |
| 5,793,969 A | 8/1998 | Kamentsky et al. |
| 5,795,317 A | 8/1998 | Brierton et al. |
| 5,795,327 A | 8/1998 | Wilson et al. |
| 5,797,515 A | 8/1998 | Liff et al. |
| 5,800,387 A | 9/1998 | Duffy et al. |
| 5,801,755 A | 9/1998 | Echerer |
| 5,803,906 A | 9/1998 | Pratt et al. |
| 5,805,442 A | 9/1998 | Crater et al. |
| 5,805,454 A | 9/1998 | Valerino et al. |
| 5,805,456 A | 9/1998 | Higham et al. |
| 5,805,505 A | 9/1998 | Zheng et al. |
| 5,807,321 A | 9/1998 | Stoker et al. |
| 5,807,322 A | 9/1998 | Lindsey et al. |
| 5,807,336 A | 9/1998 | Russo et al. |
| 5,810,747 A | 9/1998 | Brudny et al. |
| 5,812,410 A | 9/1998 | Lion et al. |
| 5,814,015 A | 9/1998 | Gargano et al. |
| 5,815,566 A | 9/1998 | Ramot et al. |
| 5,818,528 A | 10/1998 | Roth et al. |
| 5,822,418 A | 10/1998 | Yacenda et al. |
| 5,822,544 A | 10/1998 | Chaco et al. |
| 5,823,949 A | 10/1998 | Goltra |
| 5,826,237 A | 10/1998 | Macrae et al. |
| 5,829,438 A | 11/1998 | Gibbs et al. |
| 5,832,447 A | 11/1998 | Rieker et al. |
| 5,832,448 A | 11/1998 | Brown |
| 5,832,450 A | 11/1998 | Myers et al. |
| 5,833,599 A | 11/1998 | Schrier et al. |
| 5,835,897 A | 11/1998 | Dang |
| 5,836,910 A | 11/1998 | Duffy et al. |
| 5,841,975 A | 11/1998 | Layne et al. |
| 5,842,841 A | 12/1998 | Danby et al. |
| 5,842,976 A | 12/1998 | Williamson |
| 5,845,253 A | 12/1998 | Rensimer et al. |
| 5,848,593 A | 12/1998 | McGrady et al. |
| 5,851,186 A | 12/1998 | Wood et al. |
| 5,852,590 A | 12/1998 | De La Huerga |
| 5,853,387 A | 12/1998 | Clegg et al. |
| 5,855,550 A | 1/1999 | Lai et al. |
| 5,857,967 A | 1/1999 | Frid et al. |
| 5,859,972 A | 1/1999 | Subramaniam et al. |
| 5,865,745 A | 2/1999 | Schmitt et al. |
| 5,865,786 A | 2/1999 | Sibalis et al. |
| 5,867,821 A | 2/1999 | Ballantyne et al. |
| 5,871,465 A | 2/1999 | Vasko |
| 5,876,926 A | 3/1999 | Beecham |
| 5,880,443 A | 3/1999 | McDonald et al. |
| 5,882,338 A | 3/1999 | Gray |
| 5,883,370 A | 3/1999 | Walker et al. |
| 5,883,576 A | 3/1999 | De La Huerga |
| 5,884,273 A | 3/1999 | Sattizahn et al. |
| 5,884,457 A | 3/1999 | Ortiz et al. |
| 5,885,245 A | 3/1999 | Lynch et al. |
| 5,891,035 A | 4/1999 | Wood et al. |
| 5,891,734 A | 4/1999 | Gill et al. |
| 5,893,697 A | 4/1999 | Zimi et al. |
| 5,894,273 A | 4/1999 | Meador et al. |
| 5,895,371 A | 4/1999 | Levitas et al. |
| 5,897,493 A | 4/1999 | Brown |
| 5,897,530 A | 4/1999 | Jackson |
| 5,897,989 A | 4/1999 | Beecham |
| 5,899,665 A | 5/1999 | Makino et al. |
| 5,899,855 A | 5/1999 | Brown |
| 5,901,150 A | 5/1999 | Jhuboo et al. |
| 5,904,668 A | 5/1999 | Hyman et al. |
| 5,905,653 A | 5/1999 | Higham et al. |
| 5,907,291 A | 5/1999 | Chen et al. |
| 5,907,493 A | 5/1999 | Boyer et al. |
| 5,908,027 A | 6/1999 | Butterfield et al. |
| 5,910,107 A | 6/1999 | Iliff |
| 5,910,252 A | 6/1999 | Truitt et al. |
| 5,911,132 A | 6/1999 | Sloane |
| 5,911,687 A | 6/1999 | Sato et al. |
| 5,912,818 A | 6/1999 | McGrady et al. |
| 5,913,197 A | 6/1999 | Kameda |
| 5,913,310 A | 6/1999 | Brown |
| 5,915,089 A | 6/1999 | Stevens et al. |
| 5,915,240 A | 6/1999 | Karpf |
| 5,919,154 A | 7/1999 | Toays et al. |
| 5,921,938 A | 7/1999 | Aoyama et al. |
| 5,923,018 A | 7/1999 | Kameda et al. |
| 5,924,074 A | 7/1999 | Evans |

(56) References Cited

U.S. PATENT DOCUMENTS

| | | |
|---|---|---|
| 5,924,103 A | 7/1999 | Ahmed et al. |
| 5,927,540 A | 7/1999 | Godlewski |
| 5,931,791 A | 8/1999 | Saltzstein et al. |
| 5,935,060 A | 8/1999 | Iliff |
| 5,935,099 A | 8/1999 | Peterson et al. |
| 5,935,106 A | 8/1999 | Olsen |
| 5,938,413 A | 8/1999 | Makino et al. |
| 5,939,326 A | 8/1999 | Chupp et al. |
| 5,939,699 A | 8/1999 | Perttunen et al. |
| 5,940,306 A | 8/1999 | Gardner et al. |
| 5,940,802 A | 8/1999 | Hildebrand et al. |
| 5,941,829 A | 8/1999 | Saltzstein et al. |
| 5,941,846 A | 8/1999 | Duffy et al. |
| 5,942,986 A | 8/1999 | Shabot et al. |
| 5,943,423 A | 8/1999 | Muftic |
| 5,943,633 A | 8/1999 | Wilson et al. |
| 5,944,659 A | 8/1999 | Flach et al. |
| 5,945,651 A | 8/1999 | Chorosinski et al. |
| 5,946,083 A | 8/1999 | Melendez et al. |
| 5,946,659 A | 8/1999 | Lancelot et al. |
| D414,578 S | 9/1999 | Chen et al. |
| 5,950,006 A | 9/1999 | Crater et al. |
| 5,951,300 A | 9/1999 | Brown |
| 5,951,510 A | 9/1999 | Barak |
| 5,954,640 A | 9/1999 | Szabo |
| 5,954,885 A | 9/1999 | Bollish et al. |
| 5,954,971 A | 9/1999 | Pages et al. |
| 5,956,023 A | 9/1999 | Lyle et al. |
| 5,957,885 A | 9/1999 | Bollish et al. |
| 5,959,529 A | 9/1999 | Kail, IV |
| 5,960,085 A | 9/1999 | de la Huerga |
| 5,960,403 A | 9/1999 | Brown |
| 5,960,991 A | 10/1999 | Ophardt |
| 5,961,446 A | 10/1999 | Beller et al. |
| 5,961,448 A | 10/1999 | Swenson et al. |
| 5,961,487 A | 10/1999 | Davis |
| 5,961,923 A | 10/1999 | Nova et al. |
| 5,963,641 A | 10/1999 | Crandall et al. |
| 5,964,700 A | 10/1999 | Tallman et al. |
| 5,966,304 A | 10/1999 | Cook et al. |
| 5,967,975 A | 10/1999 | Ridgeway |
| 5,970,423 A | 10/1999 | Langley et al. |
| 5,971,593 A | 10/1999 | McGrady |
| 5,971,921 A | 10/1999 | Timbel |
| 5,971,948 A | 10/1999 | Pages et al. |
| 5,974,124 A | 10/1999 | Schlueter, Jr. et al. |
| 5,975,737 A | 11/1999 | Crater et al. |
| 5,980,490 A | 11/1999 | Tsoukalis |
| 5,983,193 A | 11/1999 | Heinonen et al. |
| 5,987,519 A | 11/1999 | Peifer et al. |
| 5,991,731 A | 11/1999 | Colon et al. |
| 5,993,046 A | 11/1999 | McGrady et al. |
| 5,993,420 A | 11/1999 | Hyman et al. |
| 5,995,077 A | 11/1999 | Wilcox et al. |
| 5,995,939 A | 11/1999 | Berman et al. |
| 5,995,965 A | 11/1999 | Experton |
| 5,997,167 A | 12/1999 | Crater et al. |
| 5,997,476 A | 12/1999 | Brown |
| 6,003,006 A | 12/1999 | Colella et al. |
| 6,004,020 A | 12/1999 | Bartur |
| 6,004,276 A | 12/1999 | Wright et al. |
| 6,006,191 A | 12/1999 | DiRienzo |
| 6,006,946 A | 12/1999 | Williams et al. |
| 6,009,333 A | 12/1999 | Chaco |
| 6,010,454 A | 1/2000 | Arieff et al. |
| 6,011,858 A | 1/2000 | Stock et al. |
| 6,011,999 A | 1/2000 | Holmes |
| 6,012,034 A | 1/2000 | Hamparian et al. |
| 6,013,057 A | 1/2000 | Danby et al. |
| 6,014,631 A | 1/2000 | Teagarden et al. |
| 6,016,444 A | 1/2000 | John |
| 6,017,318 A | 1/2000 | Gauthier et al. |
| 6,018,713 A | 1/2000 | Coli et al. |
| 6,019,745 A | 2/2000 | Gray |
| 6,021,392 A | 2/2000 | Lester et al. |
| 6,022,315 A | 2/2000 | Iliff |
| 6,023,522 A | 2/2000 | Draganoff et al. |
| 6,024,539 A | 2/2000 | Blomquist |
| 6,024,699 A | 2/2000 | Surwit et al. |
| 6,027,217 A | 2/2000 | McClure et al. |
| 6,029,138 A | 2/2000 | Khorasani et al. |
| 6,032,119 A | 2/2000 | Brown et al. |
| 6,032,155 A | 2/2000 | de la Huerga |
| 6,033,076 A | 3/2000 | Braeuning et al. |
| 6,039,251 A | 3/2000 | Holowko et al. |
| 6,039,467 A | 3/2000 | Holmes |
| 6,047,259 A | 4/2000 | Campbell et al. |
| 6,048,086 A | 4/2000 | Valerino |
| 6,050,940 A | 4/2000 | Braun et al. |
| 6,055,487 A | 4/2000 | Margery et al. |
| 6,057,758 A | 5/2000 | Dempsey et al. |
| 6,059,736 A | 5/2000 | Tapper |
| 6,061,603 A | 5/2000 | Papadopoulos et al. |
| 6,065,819 A | 5/2000 | Holmes et al. |
| 6,068,153 A | 5/2000 | Young et al. |
| 6,068,156 A | 5/2000 | Liff et al. |
| 6,073,046 A | 6/2000 | Patel et al. |
| 6,074,345 A | 6/2000 | van Oostrom et al. |
| 6,079,621 A | 6/2000 | Vardanyan et al. |
| 6,080,106 A | 6/2000 | Lloyd et al. |
| 6,081,048 A | 6/2000 | Bergmann et al. |
| 6,081,786 A | 6/2000 | Barry et al. |
| 6,082,776 A | 7/2000 | Feinberg |
| 6,083,206 A | 7/2000 | Molko |
| 6,093,146 A | 7/2000 | Filangeri |
| 6,095,985 A | 8/2000 | Raymond et al. |
| 6,096,561 A | 8/2000 | Tayi |
| 6,098,892 A | 8/2000 | Peoples, Jr. |
| 6,101,407 A | 8/2000 | Groezinger |
| 6,101,478 A | 8/2000 | Brown |
| 6,102,856 A | 8/2000 | Groff et al. |
| 6,108,399 A | 8/2000 | Hernandez-Guerra et al. |
| 6,108,588 A | 8/2000 | McGrady |
| 6,109,774 A | 8/2000 | Holmes et al. |
| 6,112,224 A | 8/2000 | Peifer et al. |
| RE36,871 E | 9/2000 | Epstein et al. |
| 6,113,554 A | 9/2000 | Gilcher et al. |
| 6,116,461 A | 9/2000 | Broadfield et al. |
| 6,117,940 A | 9/2000 | Mjalli |
| 6,123,524 A | 9/2000 | Danby et al. |
| 6,125,350 A | 9/2000 | Dirbas |
| 6,129,517 A | 10/2000 | Danby et al. |
| 6,132,371 A | 10/2000 | Dempsey et al. |
| 6,134,504 A | 10/2000 | Douglas et al. |
| 6,135,949 A | 10/2000 | Russo et al. |
| 6,139,177 A | 10/2000 | Venkatraman et al. |
| 6,139,495 A | 10/2000 | De La Huerga |
| 6,141,412 A | 10/2000 | Smith et al. |
| 6,144,922 A | 11/2000 | Douglas et al. |
| 6,145,695 A | 11/2000 | Garrigues |
| 6,146,523 A | 11/2000 | Kenley et al. |
| 6,148,297 A | 11/2000 | Swor et al. |
| 6,149,063 A | 11/2000 | Reynolds et al. |
| 6,151,536 A | 11/2000 | Arnold et al. |
| 6,152,364 A | 11/2000 | Schoonen et al. |
| 6,154,668 A | 11/2000 | Pedersen et al. |
| 6,154,726 A | 11/2000 | Rensimer et al. |
| 6,157,914 A | 12/2000 | Seto et al. |
| 6,158,965 A | 12/2000 | Butterfield et al. |
| 6,160,478 A | 12/2000 | Jacobsen et al. |
| 6,161,095 A | 12/2000 | Brown |
| 6,161,141 A | 12/2000 | Dillon |
| 6,163,737 A | 12/2000 | Fedor et al. |
| 6,165,154 A | 12/2000 | Gray et al. |
| 6,168,563 B1 | 1/2001 | Brown |
| 6,170,007 B1 | 1/2001 | Venkatraman et al. |
| 6,170,746 B1 | 1/2001 | Brook et al. |
| 6,171,112 B1 | 1/2001 | Clark et al. |
| 6,171,237 B1 | 1/2001 | Avitall et al. |
| 6,171,264 B1 | 1/2001 | Bader |
| 6,173,198 B1 | 1/2001 | Schulze et al. |
| 6,175,779 B1 | 1/2001 | Barrett |
| 6,175,977 B1 | 1/2001 | Schumacher et al. |
| 6,176,392 B1 | 1/2001 | William et al. |

(56) References Cited

U.S. PATENT DOCUMENTS

| | | |
|---|---|---|
| 6,182,047 B1 | 1/2001 | Dirbas |
| 6,183,417 B1 | 2/2001 | Geheb et al. |
| 6,186,145 B1 | 2/2001 | Brown |
| 6,192,320 B1 | 2/2001 | Margrey et al. |
| 6,193,480 B1 | 2/2001 | Butterfield |
| 6,195,887 B1 | 3/2001 | Danby et al. |
| 6,198,394 B1 | 3/2001 | Jacobsen et al. |
| 6,200,264 B1 | 3/2001 | Satherley et al. |
| 6,200,289 B1 | 3/2001 | Hochman et al. |
| 6,202,923 B1 | 3/2001 | Boyer et al. |
| 6,203,495 B1 | 3/2001 | Bardy |
| 6,203,528 B1 | 3/2001 | Decked et al. |
| 6,206,238 B1 | 3/2001 | Ophardt |
| 6,206,829 B1 | 3/2001 | Iliff |
| 6,210,361 B1 | 4/2001 | Kamen et al. |
| 6,213,391 B1 | 4/2001 | Lewis |
| 6,213,738 B1 | 4/2001 | Danby et al. |
| 6,213,972 B1 | 4/2001 | Butterfield et al. |
| 6,219,439 B1 | 4/2001 | Burger |
| 6,219,587 B1 | 4/2001 | Ahlin et al. |
| 6,221,009 B1 | 4/2001 | Doi et al. |
| 6,221,011 B1 | 4/2001 | Bardy |
| 6,221,012 B1 | 4/2001 | Maschke et al. |
| 6,222,619 B1 | 4/2001 | Herron et al. |
| 6,224,549 B1 | 5/2001 | Drongelen |
| 6,225,901 B1 | 5/2001 | Kail, IV |
| 6,226,564 B1 | 5/2001 | Stuart |
| 6,226,745 B1 | 5/2001 | Wiederhold |
| 6,230,142 B1 | 5/2001 | Benigno et al. |
| 6,230,927 B1 | 5/2001 | Schoonen et al. |
| 6,234,997 B1 | 5/2001 | Kamen et al. |
| 6,245,013 B1 | 6/2001 | Minoz et al. |
| 6,246,473 B1 | 6/2001 | Smith, Jr. et al. |
| 6,248,063 B1 | 6/2001 | Barnhill et al. |
| 6,248,065 B1 | 6/2001 | Brown |
| 6,255,951 B1 | 7/2001 | De La Huerga |
| 6,256,643 B1 | 7/2001 | Cork et al. |
| 6,256,967 B1 | 7/2001 | Hebron et al. |
| 6,259,355 B1 | 7/2001 | Chaco et al. |
| 6,259,654 B1 | 7/2001 | De La Huerga |
| 6,260,021 B1 | 7/2001 | Wong et al. |
| 6,266,645 B1 | 7/2001 | Simpson |
| 6,269,340 B1 | 7/2001 | Ford et al. |
| D446,854 S | 8/2001 | Cheney, II et al. |
| 6,270,455 B1 | 8/2001 | Brown |
| 6,270,457 B1 | 8/2001 | Bardy |
| 6,272,394 B1 | 8/2001 | Lipps |
| 6,272,505 B1 | 8/2001 | De La Huerga |
| 6,277,072 B1 | 8/2001 | Bardy |
| 6,278,999 B1 | 8/2001 | Knapp |
| 6,283,322 B1 | 9/2001 | Liff et al. |
| 6,283,944 B1 | 9/2001 | McMullen et al. |
| 6,290,646 B1 | 9/2001 | Cosentino et al. |
| 6,290,650 B1 | 9/2001 | Butterfield et al. |
| 6,294,999 B1 | 9/2001 | Yarin et al. |
| 6,295,506 B1 | 9/2001 | Heinonen |
| 6,304,788 B1 | 10/2001 | Eady et al. |
| 6,306,088 B1 | 10/2001 | Krausman et al. |
| 6,307,956 B1 | 10/2001 | Black |
| 6,308,171 B1 | 10/2001 | De La Huerga |
| 6,311,163 B1 | 10/2001 | Sheehan et al. |
| 6,312,227 B1 | 11/2001 | Davis |
| 6,312,378 B1 | 11/2001 | Bardy |
| 6,314,384 B1 | 11/2001 | Goetz |
| 6,317,719 B1 | 11/2001 | Schrier et al. |
| 6,319,200 B1 | 11/2001 | Lai et al. |
| 6,321,203 B1 | 11/2001 | Kameda |
| 6,322,502 B1 | 11/2001 | Schoenberg et al. |
| 6,322,504 B1 | 11/2001 | Kirshner |
| 6,322,515 B1 | 11/2001 | Goor et al. |
| 6,330,491 B1 | 12/2001 | Lion |
| 6,332,090 B1 | 12/2001 | DeFrank et al. |
| RE37,531 E | 1/2002 | Chaco et al. |
| 6,337,631 B1 | 1/2002 | Pai et al. |
| 6,338,007 B1 | 1/2002 | Broadfield et al. |
| 6,339,732 B1 | 1/2002 | Phoon et al. |
| 6,345,260 B1 | 2/2002 | Cummings, Jr. et al. |
| 6,346,886 B1 | 2/2002 | De La Huerga |
| 6,347,553 B1 | 2/2002 | Morris et al. |
| 6,352,200 B1 | 3/2002 | Schoonen et al. |
| 6,353,817 B1 | 3/2002 | Jacobs et al. |
| 6,358,225 B1 | 3/2002 | Butterfield |
| 6,358,237 B1 | 3/2002 | Paukovits et al. |
| 6,361,263 B1 | 3/2002 | Dewey et al. |
| 6,362,591 B1 | 3/2002 | Moberg |
| 6,363,282 B1 | 3/2002 | Nichols et al. |
| 6,363,290 B1 | 3/2002 | Lyle et al. |
| 6,364,834 B1 | 4/2002 | Reuss et al. |
| 6,368,273 B1 | 4/2002 | Brown |
| 6,370,841 B1 | 4/2002 | Chudy et al. |
| 6,381,577 B1 | 4/2002 | Brown |
| 6,385,505 B1 | 5/2002 | Lipps |
| 6,393,369 B1 | 5/2002 | Carr |
| 6,397,190 B1 | 5/2002 | Goetz |
| 6,401,072 B1 | 6/2002 | Haudenschild et al. |
| 6,402,702 B1 | 6/2002 | Gilcher et al. |
| 6,406,426 B1 | 6/2002 | Reuss et al. |
| 6,407,335 B1 | 6/2002 | Franklin-Lees et al. |
| 6,408,330 B1 | 6/2002 | DeLaHuerga |
| 6,416,471 B1 | 7/2002 | Kumar et al. |
| 6,421,650 B1 | 7/2002 | Goetz et al. |
| 6,424,996 B1 | 7/2002 | Killcommons et al. |
| 6,427,088 B1 | 7/2002 | Bowman, IV et al. |
| 6,434,531 B1 | 8/2002 | Lancelot et al. |
| 6,434,569 B1 | 8/2002 | Tomlinson et al. |
| 6,438,451 B1 | 8/2002 | Lion |
| RE37,829 E | 9/2002 | Charhut et al. |
| 6,449,927 B2 | 9/2002 | Hebron et al. |
| 6,450,956 B1 | 9/2002 | Rappaport et al. |
| 6,458,102 B1 | 10/2002 | Mann et al. |
| 6,461,037 B1 | 10/2002 | O'Leary |
| 6,463,310 B1 | 10/2002 | Swedlow et al. |
| 6,468,242 B1 | 10/2002 | Wilson et al. |
| 6,470,234 B1 | 10/2002 | McGrady |
| 6,471,089 B2 | 10/2002 | Liff et al. |
| 6,471,645 B1 | 10/2002 | Warkentin et al. |
| 6,471,646 B1 | 10/2002 | Thede |
| 6,475,146 B1 | 11/2002 | Frelburger et al. |
| 6,475,148 B1 | 11/2002 | Jackson et al. |
| 6,475,180 B2 | 11/2002 | Peterson et al. |
| 6,478,737 B2 | 11/2002 | Bardy |
| 6,485,465 B2 | 11/2002 | Moberg et al. |
| 6,494,831 B1 | 12/2002 | Koritzinsky |
| 6,511,138 B1 | 1/2003 | Gardner et al. |
| 6,519,569 B1 | 2/2003 | White et al. |
| 6,537,244 B2 | 3/2003 | Paukovits |
| 6,542,902 B2 | 4/2003 | Dulong et al. |
| 6,542,910 B2 | 4/2003 | Cork et al. |
| 6,544,174 B2 | 4/2003 | West et al. |
| 6,544,228 B1 | 4/2003 | Heitmeier |
| 6,551,243 B2 | 4/2003 | Bocionek et al. |
| 6,551,276 B1 | 4/2003 | Mann et al. |
| 6,554,791 B1 | 4/2003 | Cartledge et al. |
| 6,554,798 B1 | 4/2003 | Mann et al. |
| 6,555,986 B2 | 4/2003 | Moberg |
| 6,558,321 B1 | 5/2003 | Burd et al. |
| 6,561,975 B1 | 5/2003 | Pool et al. |
| 6,562,001 B2 | 5/2003 | Lebel et al. |
| 6,564,104 B2 | 5/2003 | Nelson et al. |
| 6,564,105 B2 | 5/2003 | Starkweather et al. |
| 6,564,121 B1 | 5/2003 | Wallace et al. |
| 6,571,128 B2 | 5/2003 | Lebel et al. |
| 6,575,900 B1 | 6/2003 | Zweig et al. |
| 6,577,899 B2 | 6/2003 | Lebel et al. |
| 6,579,232 B2 | 6/2003 | Sakamaki et al. |
| 6,581,069 B1 | 6/2003 | Robinson et al. |
| 6,581,798 B2 | 6/2003 | Liff et al. |
| 6,584,336 B1 | 6/2003 | Ali et al. |
| 6,585,157 B2 | 7/2003 | Brandt et al. |
| 6,585,644 B2 | 7/2003 | Lebel et al. |
| 6,585,675 B1 | 7/2003 | O×Mahony et al. |
| 6,592,551 B1 | 7/2003 | Cobb |
| 6,593,528 B2 | 7/2003 | Franklin-Lees et al. |
| 6,602,469 B1 | 8/2003 | Maus et al. |

(56) References Cited

U.S. PATENT DOCUMENTS

| | | |
|---|---|---|
| 6,607,485 B2 | 8/2003 | Bardy |
| 6,610,973 B1 | 8/2003 | Davis, III |
| 6,613,009 B1 | 9/2003 | Bainbridge et al. |
| 6,616,633 B1 | 9/2003 | Butterfield et al. |
| 6,635,014 B2 | 10/2003 | Starkweather et al. |
| 6,648,821 B2 | 11/2003 | Lebel et al. |
| 6,659,948 B2 | 12/2003 | Lebel et al. |
| 6,664,893 B1 | 12/2003 | Eveland et al. |
| 6,668,196 B1 | 12/2003 | Villegas et al. |
| 6,669,663 B1 | 12/2003 | Thompson |
| 6,673,314 B1 | 1/2004 | Burbank et al. |
| 6,687,546 B2 | 1/2004 | Lebel et al. |
| 6,689,091 B2 | 2/2004 | Bui et al. |
| 6,694,191 B2 | 2/2004 | Starkweather et al. |
| 6,694,334 B2 | 2/2004 | DuLong et al. |
| 6,711,460 B1 | 3/2004 | Reese |
| 6,731,324 B2 | 5/2004 | Levy |
| 6,733,447 B2 | 5/2004 | Lai et al. |
| 6,735,497 B2 | 5/2004 | Wallace et al. |
| 6,740,075 B2 | 5/2004 | Lebel et al. |
| 6,746,398 B2 | 6/2004 | Hervy et al. |
| 6,758,810 B2 | 7/2004 | Lebel et al. |
| 6,768,425 B2 | 7/2004 | Flaherty et al. |
| 6,771,369 B2 | 8/2004 | Rzasa et al. |
| 6,775,602 B2 | 8/2004 | Gordon, Jr. et al. |
| 6,776,304 B2 | 8/2004 | Liff et al. |
| 6,790,198 B1 | 9/2004 | White et al. |
| 6,804,656 B1 | 10/2004 | Rosenfeld et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,811,707 B2 | 11/2004 | Rovatti et al. |
| 6,813,473 B1 | 11/2004 | Bruker |
| 6,813,519 B2 | 11/2004 | Lebel et al. |
| 6,814,255 B2 | 11/2004 | Liff et al. |
| 6,820,093 B2 | 11/2004 | De La Huerga |
| 6,842,736 B1 | 1/2005 | Brzozowski |
| 6,847,861 B2 | 1/2005 | Lunak et al. |
| 6,854,088 B2 | 2/2005 | Massengale et al. |
| 6,871,211 B2 | 3/2005 | Labounty et al. |
| 6,873,268 B2 | 3/2005 | Lebel et al. |
| 6,877,530 B2 | 4/2005 | Osborne et al. |
| 6,880,034 B2 | 4/2005 | Manke et al. |
| 6,885,288 B2 | 4/2005 | Pincus |
| 6,887,201 B2 | 5/2005 | Bardy |
| 6,892,941 B2 | 5/2005 | Rosenblum |
| 6,912,549 B2 | 6/2005 | Rotter et al. |
| 6,913,590 B2 | 7/2005 | Sorenson et al. |
| 6,915,265 B1 | 7/2005 | Johnson |
| 6,915,823 B2 | 7/2005 | Osborne et al. |
| 6,928,452 B2 | 8/2005 | De La Huerga |
| 6,950,708 B2 | 9/2005 | Bowman, IV et al. |
| 6,958,705 B2 | 10/2005 | Lebel et al. |
| 6,974,437 B2 | 12/2005 | Lebel et al. |
| 6,975,924 B2 | 12/2005 | Kircher et al. |
| 6,976,628 B2 | 12/2005 | Krupa |
| 6,979,306 B2 | 12/2005 | Moll |
| 6,980,958 B1 | 12/2005 | Surwit et al. |
| 6,981,644 B2 | 1/2006 | Cheong et al. |
| 6,985,870 B2 | 1/2006 | Martucci et al. |
| 6,991,002 B2 | 1/2006 | Osborne et al. |
| 6,995,664 B1 | 2/2006 | Darling |
| 7,006,893 B2 | 2/2006 | Hart et al. |
| 7,015,806 B2 | 3/2006 | Naidoo et al. |
| 7,017,622 B2 | 3/2006 | Osborne et al. |
| 7,017,623 B2 | 3/2006 | Tribble et al. |
| 7,028,723 B1 | 4/2006 | Alouani et al. |
| 7,096,212 B2 | 8/2006 | Tribble et al. |
| 7,117,902 B2 | 10/2006 | Osborne |
| 7,151,982 B2 | 12/2006 | Liff et al. |
| 7,194,336 B2 | 3/2007 | DiGianfilippo et al. |
| 7,209,891 B1 | 4/2007 | Addy et al. |
| 7,240,699 B2 | 7/2007 | Osborne et al. |
| 7,255,680 B1 | 8/2007 | Gharib |
| 7,277,579 B2 | 10/2007 | Huang |
| 7,277,757 B2 | 10/2007 | Casavant et al. |
| 7,317,967 B2 | 1/2008 | DiGianfilippo et al. |
| 7,321,861 B1 | 1/2008 | Oon |
| 7,343,224 B2 | 3/2008 | DiGianfilippo et al. |
| 7,403,901 B1 | 7/2008 | Carley et al. |
| 7,427,002 B2 | 9/2008 | Liff et al. |
| 7,493,263 B2 | 2/2009 | Helmus et al. |
| 7,499,581 B2 | 3/2009 | Tribble et al. |
| 7,509,280 B1 | 3/2009 | Haudenschild |
| 7,555,557 B2 | 6/2009 | Bradley et al. |
| 7,561,312 B1 | 7/2009 | Proudfoot et al. |
| 7,581,953 B2 | 9/2009 | Lehmann et al. |
| 7,599,516 B2 | 10/2009 | Limer et al. |
| 7,610,115 B2 | 10/2009 | Rob et al. |
| 7,630,908 B1 | 12/2009 | Amrien et al. |
| 7,636,718 B1 | 12/2009 | Steen et al. |
| 7,672,859 B1 | 3/2010 | Louie et al. |
| 7,698,019 B2 | 4/2010 | Moncrief et al. |
| 7,698,154 B2 | 4/2010 | Marchosky |
| 7,734,478 B2 | 6/2010 | Goodall et al. |
| 7,753,085 B2 | 7/2010 | Tribble et al. |
| 7,769,601 B1 | 8/2010 | Bleser et al. |
| 7,783,383 B2 | 8/2010 | Eliuk et al. |
| D624,225 S | 9/2010 | Federico et al. |
| 7,801,642 B2 | 9/2010 | Ansari et al. |
| 7,847,970 B1 | 12/2010 | McGrady |
| 7,853,621 B2 | 12/2010 | Guo |
| 7,904,822 B2 | 3/2011 | Monteleone et al. |
| 7,931,859 B2 | 4/2011 | Mlodzinski et al. |
| 7,937,290 B2 | 5/2011 | Bahir |
| 7,986,369 B1 | 7/2011 | Burns |
| 7,991,507 B2 | 8/2011 | Liff et al. |
| 8,170,271 B2 | 5/2012 | Chen |
| 8,191,339 B2 | 6/2012 | Tribble et al. |
| 8,215,557 B1 | 7/2012 | Reno et al. |
| 8,220,503 B2 | 7/2012 | Tribble et al. |
| 8,225,824 B2 | 7/2012 | Eliuk et al. |
| D667,961 S | 9/2012 | Marmier |
| 8,267,129 B2 | 9/2012 | Doherty et al. |
| 8,271,138 B2 | 9/2012 | Eliuk et al. |
| 8,280,549 B2 | 10/2012 | Liff et al. |
| 8,284,305 B2 | 10/2012 | Newcomb et al. |
| 8,374,887 B1 | 2/2013 | Alexander |
| 8,386,070 B2 | 2/2013 | Eliuk et al. |
| 8,548,824 B1 | 10/2013 | daCosta |
| 8,554,579 B2 | 10/2013 | Tribble et al. |
| D693,480 S | 11/2013 | Spiess et al. |
| 8,595,206 B1 | 11/2013 | Ansari |
| 8,666,541 B1 | 3/2014 | Ansari et al. |
| 8,678,047 B2 | 3/2014 | Tribble et al. |
| 8,719,217 B1 * | 5/2014 | Vivalda ............... G06F 16/283 707/608 |
| D715,958 S | 10/2014 | Bossart et al. |
| 9,053,218 B2 | 6/2015 | Osborne et al. |
| D733,480 S | 7/2015 | Shao |
| D738,152 S | 9/2015 | Grasselli et al. |
| D753,428 S | 4/2016 | Shao |
| 9,362,969 B1 | 6/2016 | Burgess et al. |
| 9,382,021 B2 | 7/2016 | Tribble et al. |
| 9,662,273 B2 | 5/2017 | Ranalletta et al. |
| 9,930,297 B2 | 3/2018 | Alexander et al. |
| 9,956,145 B2 | 5/2018 | Thompson et al. |
| 2001/0001237 A1 | 5/2001 | Stroda et al. |
| 2001/0003177 A1 | 6/2001 | Schena et al. |
| 2001/0007053 A1 | 7/2001 | Bardy |
| 2001/0007932 A1 | 7/2001 | Kamen et al. |
| 2001/0011153 A1 | 8/2001 | Bardy |
| 2001/0016699 A1 | 8/2001 | Burbank et al. |
| 2001/0017817 A1 | 8/2001 | De La Huerga |
| 2001/0021801 A1 | 9/2001 | Bardy |
| 2001/0025138 A1 | 9/2001 | Bardy |
| 2001/0025156 A1 | 9/2001 | Bui et al. |
| 2001/0027634 A1 | 10/2001 | Hebron et al. |
| 2001/0028308 A1 | 10/2001 | De La Huerga |
| 2001/0030234 A1 | 10/2001 | Wiklof |
| 2001/0031944 A1 | 10/2001 | Peterson et al. |
| 2001/0032101 A1 | 10/2001 | Statius Muller |
| 2001/0034502 A1 | 10/2001 | Moberg et al. |
| 2001/0034614 A1 | 10/2001 | Fletcher-Haynes et al. |

(56) References Cited

U.S. PATENT DOCUMENTS

| | | |
|---|---|---|
| 2001/0034616 A1 | 10/2001 | Giannini |
| 2001/0037057 A1 | 11/2001 | Bardy |
| 2001/0037083 A1 | 11/2001 | Hartlaub et al. |
| 2001/0037217 A1 | 11/2001 | Abensour et al. |
| 2001/0037220 A1 | 11/2001 | Merry et al. |
| 2001/0041920 A1 | 11/2001 | Starkweather et al. |
| 2001/0044588 A1 | 11/2001 | Mault |
| 2001/0044731 A1 | 11/2001 | Coffman et al. |
| 2001/0047125 A1 | 11/2001 | Quy |
| 2001/0051764 A1 | 12/2001 | Bardy |
| 2001/0053885 A1 | 12/2001 | Gielen et al. |
| 2002/0002326 A1 | 1/2002 | Causey, III et al. |
| 2002/0002473 A1 | 1/2002 | Schrier et al. |
| 2002/0004645 A1 | 1/2002 | Carlisle et al. |
| 2002/0007285 A1 | 1/2002 | Rappaport |
| 2002/0010568 A1 | 1/2002 | Rubbert et al. |
| 2002/0010679 A1* | 1/2002 | Felsher ............ G06F 19/328 705/51 |
| 2002/0013612 A1 | 1/2002 | Whitehurst |
| 2002/0016567 A1 | 2/2002 | Hochman et al. |
| 2002/0016568 A1 | 2/2002 | Lebel et al. |
| 2002/0016719 A1 | 2/2002 | Nemeth et al. |
| 2002/0016722 A1 | 2/2002 | Kameda |
| 2002/0019606 A1 | 2/2002 | Lebel et al. |
| 2002/0019748 A1 | 2/2002 | Brown |
| 2002/0022776 A1 | 2/2002 | Bardy |
| 2002/0025796 A1 | 2/2002 | Taylor et al. |
| 2002/0026104 A1 | 2/2002 | Bardy |
| 2002/0029157 A1 | 3/2002 | Marchosky |
| 2002/0029776 A1 | 3/2002 | Blomquist |
| 2002/0032582 A1 | 3/2002 | Feeney et al. |
| 2002/0032602 A1 | 3/2002 | Lanzillo, Jr. et al. |
| 2002/0038392 A1 | 3/2002 | De La Huerga |
| 2002/0040208 A1 | 4/2002 | Flaherty et al. |
| 2002/0044043 A1 | 4/2002 | Chaco et al. |
| 2002/0046062 A1 | 4/2002 | Kameda |
| 2002/0046185 A1 | 4/2002 | Villart et al. |
| 2002/0046346 A1 | 4/2002 | Evans |
| 2002/0052539 A1 | 5/2002 | Haller et al. |
| 2002/0052542 A1 | 5/2002 | Bardy |
| 2002/0052574 A1 | 5/2002 | Hochman et al. |
| 2002/0062227 A1 | 5/2002 | Yuyama |
| 2002/0062229 A1 | 5/2002 | Alban et al. |
| 2002/0065540 A1 | 5/2002 | Lebel et al. |
| 2002/0065686 A1 | 5/2002 | Monteleone et al. |
| 2002/0067273 A1 | 6/2002 | Jaques et al. |
| 2002/0072733 A1 | 6/2002 | Flaherty |
| 2002/0073250 A1 | 6/2002 | Ommering |
| 2002/0077852 A1 | 6/2002 | Ford et al. |
| 2002/0077865 A1 | 6/2002 | Sullivan |
| 2002/0082480 A1 | 6/2002 | Riff et al. |
| 2002/0082865 A1 | 6/2002 | Bianco et al. |
| 2002/0082868 A1 | 6/2002 | Pories et al. |
| 2002/0084904 A1 | 7/2002 | De La Huerga |
| 2002/0087120 A1 | 7/2002 | Rogers et al. |
| 2002/0091309 A1 | 7/2002 | Auer |
| 2002/0099283 A1 | 7/2002 | Christ et al. |
| 2002/0099301 A1 | 7/2002 | Bardy |
| 2002/0100762 A1 | 8/2002 | Liff et al. |
| 2002/0107476 A1 | 8/2002 | Mann et al. |
| 2002/0107707 A1 | 8/2002 | Naparstek et al. |
| 2002/0116226 A1 | 8/2002 | Auer et al. |
| 2002/0116509 A1 | 8/2002 | De La Huerga |
| 2002/0128606 A1 | 9/2002 | Cowan et al. |
| 2002/0128871 A1 | 9/2002 | Adamson et al. |
| 2002/0128880 A1 | 9/2002 | Kunikiyo |
| 2002/0133377 A1 | 9/2002 | Brown |
| 2002/0140675 A1 | 10/2002 | Ali et al. |
| 2002/0143254 A1 | 10/2002 | Maruyama |
| 2002/0156462 A1 | 10/2002 | Stultz |
| 2002/0158128 A1 | 10/2002 | Ashiuro |
| 2002/0165491 A1 | 11/2002 | Reilly |
| 2002/0169636 A1 | 11/2002 | Eggers et al. |
| 2002/0173875 A1 | 11/2002 | Wallace et al. |
| 2002/0188467 A1 | 12/2002 | Eke |
| 2002/0198473 A1 | 12/2002 | Kumar et al. |
| 2002/0198513 A1 | 12/2002 | Lebel et al. |
| 2002/0198624 A1 | 12/2002 | Greenwald |
| 2003/0006878 A1 | 1/2003 | Chung |
| 2003/0023177 A1 | 1/2003 | Bardy |
| 2003/0033532 A1 | 2/2003 | Marks |
| 2003/0036783 A1 | 2/2003 | Bauhahn et al. |
| 2003/0046114 A1 | 3/2003 | Davies et al. |
| 2003/0046280 A1 | 3/2003 | Rotter et al. |
| 2003/0046439 A1 | 3/2003 | Manke et al. |
| 2003/0050621 A1 | 3/2003 | Lebel et al. |
| 2003/0050731 A1 | 3/2003 | Rosenblum |
| 2003/0052787 A1 | 3/2003 | Zerhusen |
| 2003/0060753 A1 | 3/2003 | Starkweather et al. |
| 2003/0060754 A1 | 3/2003 | Reilly |
| 2003/0060765 A1 | 3/2003 | Campbell et al. |
| 2003/0060768 A1 | 3/2003 | Kiyatake |
| 2003/0065287 A1 | 4/2003 | Spohn et al. |
| 2003/0076736 A1 | 4/2003 | Buker et al. |
| 2003/0078534 A1 | 4/2003 | Hochman et al. |
| 2003/0079746 A1 | 5/2003 | Hickle |
| 2003/0083901 A1 | 5/2003 | Bosch et al. |
| 2003/0088238 A1 | 5/2003 | Poulsen et al. |
| 2003/0097092 A1 | 5/2003 | Flaherty |
| 2003/0114836 A1 | 6/2003 | Estes et al. |
| 2003/0117580 A1 | 6/2003 | Franz et al. |
| 2003/0125609 A1 | 7/2003 | Becker |
| 2003/0125611 A1 | 7/2003 | Bardy |
| 2003/0139701 A1 | 7/2003 | White et al. |
| 2003/0144878 A1 | 7/2003 | Wilkes et al. |
| 2003/0149599 A1 | 8/2003 | Goodall et al. |
| 2003/0154108 A1 | 8/2003 | Fletcher-Haynes et al. |
| 2003/0158508 A1 | 8/2003 | DiGianfilippo |
| 2003/0160683 A1 | 8/2003 | Blomquist |
| 2003/0163088 A1 | 8/2003 | Blomquist |
| 2003/0163223 A1 | 8/2003 | Blomquist |
| 2003/0163789 A1 | 8/2003 | Blomquist |
| 2003/0167035 A1 | 9/2003 | Flaherty et al. |
| 2003/0176933 A1 | 9/2003 | Lebel et al. |
| 2003/0179287 A1 | 9/2003 | Kozic et al. |
| 2003/0181851 A1 | 9/2003 | Mann et al. |
| 2003/0182164 A1* | 9/2003 | Shabot ............ G06Q 10/10 705/3 |
| 2003/0195397 A1 | 10/2003 | Bardy |
| 2003/0200117 A1 | 10/2003 | Manetta et al. |
| 2003/0201697 A1 | 10/2003 | Richardson |
| 2003/0212379 A1 | 11/2003 | Bylund et al. |
| 2003/0225596 A1 | 12/2003 | Richardson et al. |
| 2003/0225728 A1 | 12/2003 | Moura |
| 2003/0231803 A1 | 12/2003 | Huang |
| 2004/0002874 A1 | 1/2004 | Shaffer et al. |
| 2004/0017475 A1 | 1/2004 | Akers et al. |
| 2004/0019607 A1 | 1/2004 | Moubayed et al. |
| 2004/0115132 A1 | 1/2004 | Brown |
| 2004/0039260 A1 | 2/2004 | Bardy |
| 2004/0039264 A1 | 2/2004 | Bardy |
| 2004/0051368 A1 | 3/2004 | Caputo et al. |
| 2004/0055611 A1 | 3/2004 | Penny et al. |
| 2004/0064343 A1 | 4/2004 | Korpman et al. |
| 2004/0073329 A1 | 4/2004 | Engleson |
| 2004/0088187 A1 | 5/2004 | Chudy et al. |
| 2004/0088374 A1 | 5/2004 | Webb et al. |
| 2004/0111293 A1 | 6/2004 | Firanek et al. |
| 2004/0116862 A1 | 6/2004 | Ray |
| 2004/0117215 A1 | 6/2004 | Marchosky |
| 2004/0128162 A1 | 7/2004 | Schlotterbeck et al. |
| 2004/0129616 A1 | 7/2004 | Mori et al. |
| 2004/0148195 A1 | 7/2004 | Kalies |
| 2004/0158193 A1 | 8/2004 | Bui et al. |
| 2004/0172283 A1 | 9/2004 | Vanderveen et al. |
| 2004/0172289 A1 | 9/2004 | Kozic et al. |
| 2004/0172300 A1 | 9/2004 | Mihai et al. |
| 2004/0193328 A1 | 9/2004 | Zaitsu et al. |
| 2004/0193453 A1 | 9/2004 | Butterfield et al. |
| 2004/0204673 A1 | 10/2004 | Flaherty |
| 2004/0204954 A1 | 10/2004 | Lacko |
| 2004/0215490 A1 | 10/2004 | Duchon et al. |
| 2004/0220829 A1 | 11/2004 | Baharav et al. |
| 2004/0225528 A1 | 11/2004 | Brock |

(56) References Cited

U.S. PATENT DOCUMENTS

| | | |
|---|---|---|
| 2004/0235446 A1 | 11/2004 | Flaherty et al. |
| 2004/0236630 A1 | 11/2004 | Kost et al. |
| 2004/0248295 A1 | 12/2004 | Katsuhiko et al. |
| 2004/0260233 A1 | 12/2004 | Garibotto et al. |
| 2004/0260577 A1 | 12/2004 | Dahlin et al. |
| 2005/0001033 A1 | 1/2005 | Cheong et al. |
| 2005/0017864 A1 | 1/2005 | Tsoukalis |
| 2005/0021369 A1* | 1/2005 | Cohen .................. H04L 67/306 705/2 |
| 2005/0033124 A1 | 2/2005 | Kelly et al. |
| 2005/0033773 A1 | 2/2005 | Roberge et al. |
| 2005/0038680 A1 | 2/2005 | McMahon |
| 2005/0039742 A1 | 2/2005 | Hickle |
| 2005/0043665 A1 | 2/2005 | Vinci et al. |
| 2005/0045548 A1 | 3/2005 | Brugger et al. |
| 2005/0054923 A1 | 3/2005 | Pan |
| 2005/0060372 A1 | 3/2005 | DeBettencourt et al. |
| 2005/0065823 A1* | 3/2005 | Ramraj ................ G06F 21/6245 705/3 |
| 2005/0080651 A1 | 4/2005 | Morrison et al. |
| 2005/0108044 A1* | 5/2005 | Koster ................ G06F 19/3462 705/2 |
| 2005/0187794 A1 | 8/2005 | Kimak |
| 2005/0209737 A1 | 9/2005 | Kircher |
| 2005/0228238 A1 | 10/2005 | Monitzer |
| 2005/0279419 A1 | 12/2005 | Tribble et al. |
| 2006/0084042 A1 | 4/2006 | Weaver et al. |
| 2006/0124656 A1 | 6/2006 | Popovich, Jr. |
| 2006/0136095 A1 | 6/2006 | Rob et al. |
| 2006/0149416 A1 | 7/2006 | Mohapatra et al. |
| 2006/0161294 A1 | 7/2006 | DiMaggio |
| 2006/0173714 A1 | 8/2006 | Grotzinger, Jr. |
| 2006/0178578 A1 | 8/2006 | Tribble et al. |
| 2006/0181391 A1 | 8/2006 | McNeill et al. |
| 2006/0235881 A1 | 10/2006 | Masarie et al. |
| 2007/0043767 A1 | 2/2007 | Osborne et al. |
| 2007/0047980 A1 | 3/2007 | Limer et al. |
| 2007/0088568 A1 | 4/2007 | Goodall et al. |
| 2007/0100660 A1* | 5/2007 | Carosso ................ G06Q 10/10 705/2 |
| 2007/0100662 A1* | 5/2007 | Suwalski ............. G06Q 10/06 705/2 |
| 2007/0110305 A1 | 5/2007 | Corcoran et al. |
| 2007/0125442 A1 | 6/2007 | Tribble et al. |
| 2007/0168228 A1 | 7/2007 | Lawless |
| 2007/0179806 A1 | 8/2007 | Knowlton et al. |
| 2007/0189597 A1 | 8/2007 | Limer et al. |
| 2007/0192139 A1 | 8/2007 | Cookson et al. |
| 2007/0216998 A1 | 9/2007 | Sander |
| 2007/0239482 A1 | 10/2007 | Finn et al. |
| 2007/0239997 A1 | 10/2007 | Qu et al. |
| 2008/0046292 A1 | 2/2008 | Myers et al. |
| 2008/0056556 A1 | 3/2008 | Eller et al. |
| 2008/0059228 A1 | 3/2008 | Bossi et al. |
| 2008/0091467 A1 | 4/2008 | Moncrief et al. |
| 2008/0119958 A1 | 5/2008 | Bear et al. |
| 2008/0125897 A1 | 5/2008 | DiGianfilippo et al. |
| 2008/0147554 A1 | 6/2008 | Stevens et al. |
| 2008/0195246 A1 | 8/2008 | Tribble et al. |
| 2008/0306926 A1 | 12/2008 | Friedlander et al. |
| 2009/0024414 A1* | 1/2009 | Mansour ................ G16H 40/20 705/3 |
| 2009/0080408 A1 | 3/2009 | Natoli et al. |
| 2009/0097368 A1 | 4/2009 | Vlutters et al. |
| 2009/0138340 A1 | 5/2009 | Borr et al. |
| 2009/0188937 A1 | 7/2009 | Kim |
| 2009/0205877 A1 | 8/2009 | Claypool |
| 2009/0210252 A1 | 8/2009 | Silver |
| 2009/0216560 A1* | 8/2009 | Siegel ................ G06Q 10/06 705/3 |
| 2009/0235194 A1 | 9/2009 | Arndt et al. |
| 2009/0258331 A1 | 10/2009 | Do et al. |
| 2009/0285762 A1 | 11/2009 | Flower |
| 2009/0313044 A1 | 12/2009 | Hague et al. |
| 2009/0323170 A1 | 12/2009 | Lin |
| 2009/0324032 A1 | 12/2009 | Chen |
| 2010/0017031 A1 | 1/2010 | Rob et al. |
| 2010/0091281 A1 | 4/2010 | Suzuki |
| 2010/0094653 A1 | 4/2010 | Tribble et al. |
| 2010/0128165 A1 | 5/2010 | Newcomb et al. |
| 2010/0157293 A9 | 6/2010 | Rzasa et al. |
| 2010/0185456 A1 | 7/2010 | Kansal |
| 2010/0241270 A1 | 9/2010 | Eliuk et al. |
| 2011/0119088 A1 | 5/2011 | Gunn |
| 2011/0191121 A1 | 8/2011 | Fioravanti |
| 2011/0202366 A1 | 8/2011 | Akers et al. |
| 2011/0208350 A1 | 8/2011 | Eliuk et al. |
| 2011/0267465 A1 | 11/2011 | Alexander et al. |
| 2012/0022885 A1* | 1/2012 | Murayama ............. G16H 40/20 705/2 |
| 2012/0097290 A1 | 4/2012 | Mikhaeil |
| 2012/0200596 A1 | 8/2012 | Gotou et al. |
| 2012/0211565 A1 | 8/2012 | Colavito et al. |
| 2012/0303388 A1 | 11/2012 | Vishnubhatla et al. |
| 2013/0079581 A1 | 3/2013 | Agamaite et al. |
| 2013/0090947 A1 | 4/2013 | Nockley |
| 2013/0136330 A1* | 5/2013 | Takagi .................. A61B 6/563 382/131 |
| 2013/0197445 A1 | 8/2013 | Schabbach et al. |
| 2013/0262138 A1 | 10/2013 | Jaskela et al. |
| 2013/0279774 A1 | 10/2013 | Helgason et al. |
| 2013/0304510 A1 | 11/2013 | Chan et al. |
| 2013/0314535 A1 | 11/2013 | Yuyama et al. |
| 2013/0342676 A1 | 12/2013 | Amano |
| 2014/0022569 A1 | 1/2014 | Matsui et al. |
| 2014/0067407 A1* | 3/2014 | Sathe .................... G06Q 50/22 705/2 |
| 2014/0156064 A1 | 6/2014 | Crawford et al. |
| 2014/0156294 A1 | 6/2014 | Tribble et al. |
| 2014/0214436 A1 | 7/2014 | Utech et al. |
| 2014/0350950 A1 | 11/2014 | Jaskela et al. |
| 2015/0205932 A1 | 7/2015 | Tribble |
| 2015/0227719 A1 | 8/2015 | Ranalletta |
| 2015/0272320 A1 | 10/2015 | Ranalletta et al. |
| 2015/0278477 A1 | 10/2015 | Tribble |
| 2015/0286799 A1 | 10/2015 | Padmani |
| 2016/0072985 A1 | 3/2016 | Sandmann et al. |
| 2016/0092638 A1 | 3/2016 | Padmani |
| 2016/0092639 A1 | 3/2016 | Padmani |
| 2016/0140315 A1 | 5/2016 | Diaz et al. |
| 2016/0210437 A1 | 7/2016 | Padmani et al. |
| 2016/0371462 A1 | 12/2016 | Wallen |
| 2017/0372034 A1 | 12/2017 | Tribble |

FOREIGN PATENT DOCUMENTS

| | | |
|---|---|---|
| CN | 1131076 | 12/2003 |
| EP | 0237588 | 9/1987 |
| EP | 0462466 | 12/1991 |
| EP | 0505627 | 9/1992 |
| EP | 0522527 | 1/1993 |
| EP | 0439355 | 9/1994 |
| EP | 0844581 | 5/1998 |
| EP | 0960627 | 12/1999 |
| EP | 0970655 | 1/2000 |
| EP | 1072994 | 2/2001 |
| EP | 1107158 A1 | 6/2001 |
| EP | 1097671 | 2/2003 |
| GB | 994977 A | 6/1965 |
| GB | 2210713 | 2/1987 |
| GB | 2279784 | 1/1995 |
| GB | 2285135 | 6/1995 |
| GB | 2379037 | 2/2003 |
| JP | 53137644 | 12/1978 |
| JP | 61066950 | 4/1986 |
| JP | 63068133 | 3/1988 |
| JP | 2111375 | 4/1990 |
| JP | 3423055 B2 | 1/1994 |
| JP | 6086813 | 3/1994 |

(56) References Cited

FOREIGN PATENT DOCUMENTS

| | | |
|---|---|---|
| JP | 06327636 | 11/1994 |
| JP | 07204253 A | 8/1995 |
| JP | 104585 | 1/1998 |
| JP | 10014890 | 1/1998 |
| JP | 10079770 | 3/1998 |
| JP | 2000036032 A | 2/2000 |
| JP | 03055131 | 4/2000 |
| JP | 2002011095 | 1/2002 |
| JP | 2002092181 A | 3/2002 |
| JP | 2002520718 | 7/2002 |
| JP | 2003022322 | 1/2003 |
| JP | 2004078970 | 3/2004 |
| JP | 2004326436 | 11/2004 |
| JP | 2004340770 A | 12/2004 |
| JP | 2005252710 A | 9/2005 |
| JP | 2005284703 | 10/2005 |
| JP | 2005284703 A | 10/2005 |
| JP | 2006033291 A | 2/2006 |
| JP | 2006334062 | 12/2006 |
| JP | 2007198934 A | 8/2007 |
| JP | 2008139201 A | 6/2008 |
| JP | 4276654 B2 | 6/2009 |
| JP | 2009265827 A | 11/2009 |
| JP | 2010056619 A | 3/2010 |
| JP | 2010170504 A | 8/2010 |
| JP | 2010533927 A | 10/2010 |
| JP | 2011151430 A | 8/2011 |
| JP | 2012078265 | 4/2012 |
| JP | 5342197 B2 | 11/2013 |
| JP | 5747150 B2 | 7/2015 |
| JP | 6086813 | 3/2017 |
| KR | 20000036642 | 7/2000 |
| KR | 1020000036642 | 7/2000 |
| KR | 20010094703 A | 11/2001 |
| KR | 1020010094703 | 11/2001 |
| KR | 20050054379 | 12/2003 |
| KR | 20110115927 A | 10/2011 |
| KR | 1020110115927 | 10/2011 |
| KR | 20130001500 | 1/2013 |
| WO | WO8400493 | 2/1984 |
| WO | WO9524010 A1 | 9/1995 |
| WO | WO9634291 A1 | 10/1996 |
| WO | WO9741525 | 11/1997 |
| WO | WO9814275 A1 | 4/1998 |
| WO | WO9815092 A1 | 4/1998 |
| WO | WO9824358 A1 | 6/1998 |
| WO | WO9833433 A1 | 8/1998 |
| WO | WO9859487 | 12/1998 |
| WO | WO9904043 | 1/1999 |
| WO | WO9910029 | 3/1999 |
| WO | WO9942933 | 8/1999 |
| WO | WO9944162 | 9/1999 |
| WO | WO9959472 | 11/1999 |
| WO | WO0013588 | 3/2000 |
| WO | WO0029983 | 5/2000 |
| WO | WO0043941 | 7/2000 |
| WO | WO0052437 | 9/2000 |
| WO | WO0052626 | 9/2000 |
| WO | WO0057339 | 9/2000 |
| WO | WO0060449 | 10/2000 |
| WO | WO0069331 | 11/2000 |
| WO | WO0072181 | 11/2000 |
| WO | WO0078374 | 12/2000 |
| WO | WO0101305 | 1/2001 |
| WO | WO0102979 | 1/2001 |
| WO | WO0106468 | 1/2001 |
| WO | WO0145774 | 6/2001 |
| WO | WO0217777 | 7/2002 |
| WO | WO02091276 A1 | 11/2002 |
| WO | WO03025826 A2 | 3/2003 |
| WO | WO03094073 | 11/2003 |
| WO | WO2004070557 | 8/2004 |
| WO | WO2004070994 | 8/2004 |
| WO | WO-2005043440 A1 * 5/2005 ............. G06Q 50/24 |

OTHER PUBLICATIONS

Written Opinion dated Apr. 4, 2018 in corresponding Singapore Patent Application No. 11201704359V.

AHRQ Health Information Technology Program—Update 2005-06 Fact Sheet,, http://www.ahrq.gov/research/findings/factsheets/it/hitfact/index.html—3 pages.

Albert A. Cook, "An integrated nursing-pharmacy approach to a computerized medication dispensing/administration system," Hospital Pharmacy, May 1985, pp. 321-325, vol. 20, JB Lippincott Company, Philadelphia, PA.

Allan T. Pryor, "Current State of Computer-based Patient Record Systems," Aspects of the Computer-based Patient Record, 1992, pp. 67-82, Springer-Verlag, New York, NY.

Anderson, Howard "A Narrative on the History of the Development of Telepharmacy in North Dakota from the Board of Pharmacy's Perspective Recorded by Excerpts from Board Minutes", Feb. 2006.

Angaran, "Telemedicine and telepharmacy: Current status and future implications", Am J Health-Syst Pharm, vol. 56, Jul. 15, 1999, pp. 1404-1405.

Ann Slone Endo, "Using Computers in Newborn Intensive Care Settings," American Journal of Nursing, Jul. 1981, pp. 1336-1337.

Anonymous, "Chains covet customized pharmacy integration" Drug Store New, Aug. 18, 2003, vol. 25, No. 10—p. 73.

Automated Dispensing Technologies: Directory of Vendors, http://pharmacyautomation.com/vendors.html, Jun. 5, 2003—3 pages.

Auto Syringe® AS40A Infusion Pump Technical Manual, 1995, 89 pages, Baxter Healthcare Corporation, Deerfield, IL.

Auto Syringe® AS40A: Model AS40A Infusion Pump Operation Manual, undated, 78 pages, Baxter Healthcare Corporation, Deerfield, IL.

Baxa Corporation, DoseEdge The Leading Edge in Dose Management, Brochure, published copyright date 2010—5 pages.

Baxa Corporation, Product Catalog 2010-2011, published at least by Sep. 15, 2012, https://web.archive.org/web/20120915210739http://www.baxa.com/resources/docs/BaxaCatalog.pdf (52 pages).

Bell Atlantic Healthcare Systems, Inc., court exhibit, StatLan Functions and Features, Specification, release 3.5, dated Nov. 12, 1992, 49 pages.

Ben Schneiderman, "Designing the User Interface: Strategies for Effective Human-Computer Interaction," 2d Ed., 1992, Chapter 5: Direct Manipulation (56 pages), Addison-Wesley Publishing Company.

"Block Medical: Growing with Home Infusion Therapy," taken from INVIVO, The Business and Medicine Report, Apr. 1991, pp. 7-9.

Bynum et al., "The Effect of Telepharmacy Counseling on Metered-Dose Inhaler Technique among Adolescents with Asthma in Rural Arkansas", Telemedicine Journal and e-health, vol. 7, No. 3, 2001, Mary AnnLiebert, Inc., pp. 207-218.

Cabral, Jr. et al., "Multmedia Systems for Telemedicine Systems for Telemedicine and Their Communications Requirements," IEEE Communications Magazine Jul. 1996, pp. 20-27.

Cardinal Health Introduces Rxe-source(SM) to Address Pharmacist Labor Shortage and Medication Safety Challenges at Hospitals. PR Newswire, Feb. 25, 2003—5 pages.

Casey, Michelle M. et al., "Pharmacist Staffing and the Use of Technology in Small Rural Hospitals: Implications for Medication Safety" Upper Midwest Rural Health Research Center, Dec. 2005—51 pages.

Cato Reference Manual, Support for Trial Version (Abridged), Vienna, May 2004 Jun. 1, 2004.

Cato Reference Manual, Vienna, May 2005 May 1, 2005.

Charles Safran, M.D. et al., "Computer-Based Support for Clinical Decision Making," Clinical Computin, vol. 7, No. 5 (1990), pp. 319-322.

Clayton M. Curtis, "A Computer-based Patient Record Emerging from the Public Sector: The Decentralized Hospital Computer Program," First Annual Nicholas E. Davies Award Proceedings of the CPR Recognition Symposium, 1995, pp. 75-132, Computer-based Patient Record Institute, Inc., Bethesda, MD.

Clement J. McDonald, M.D. et al, "The Three-Legged Stool: Regenstrief Institute for Health Care," Third Annual Nicholas E.

(56) References Cited

OTHER PUBLICATIONS

Davies Award Proceedings of the CPR Recognition Symposium, 1997, pp. 131-158, Computer-based Patient Record Institute, Inc., Bethesda, MD.
Clement J. McDonald, M.D. et al., The Regenstrief Medical Record System: 20 Years of Experience in Hospitals, Clinics, and Neighborhood Health Centers,: M.D. Computing, 1992 pp. 206-217, vol. 9, No. 4, Springer-Verlag, New York, NY.
Clifton, G. Dennis et al., "Provision of pharmacy services to underserved populations via remote dispensing and two-way videoconferencing" Am J Health-Syst Pharm, vol. 60, Dec. 15, 2003 oe pp. 2577-2582.
Dan Murphy, "Nuclear Pharmacy Primer", Radiation Protection Management, vol. 20, No. 5 (2003), pp. 1-10.
Dan Scheraga; "Tech firms answer chain pharmacy's call for productivity," Drug Store News; Dec. 15, 2003; 25, 17; ProQuest Research Library, p. 31-32.
Daniel Andresen et al., "Scalability Issues for High Performance Digital Libraries on the World Wide Web," Proceedings of ADL '96, 1996, pp. 139-148, IEEE.
Daniel J. Nigrin et al., "Glucoweb: A Case Study of Secure, Remote Biomonitoring and Communication," Proceedings of the 2000, 5 pages, American Medical Informatics Association, Bethesda, MD.
Darryl V. Wareham et al., "Combination Medication Cart and Computer Terminal in Decentralized Drug Distribution," American Journal of Hospital Pharmacy, Jun. 1983, pp. 976-978, vol. 40, American Society of Hospital Pharmacists.
Dart, Luann, "Digital Doses" Rural Electric, Jan. 2005—pp. 28-31.
Deborah J. Mayhew, "Principles and Guidelines in Software user Interface Designs," 1992, selected portions of Chapter 9, 17 pages, Prentice-Hall, Inc.
Defendants Initial Invalidity Contentions with Exhibits A and B dated Sep. 8, 2014; Civil Action No. 1:14-cv-00222.
Dennis D. Cote et al., "Robotic system for i.v. antineoplastic drug preparation: Description and preliminary evaluation under simulated conditions," American Journal of Hospital Pharmacy, Nov. 1989, pp. 2286-2293, vol. 46, American Society of Hospital Pharmacists.
Donna Young; "Loan repayments help pharmacists provide care in medically underserved areas," American Journal of Health-System Pharmacy; Nov. 1, 2003; pp. 2186-2188, vol. 60.
Environmental Scan of Pharmacy Technicians; M. MacInnis; Canadian Pharmacists Association; Sep. 2001.
Exhibit 1, Publications Manually Reviewed for the Search to U.S. Pat. No. 8,347,887 titled "System and Method for Remotely Supervising and Verifying Pharmacy Functions" As of Jun. 25, 2014.
Exhibit 1001 U.S. Pat. No. 8,374,887, Alexander issued Feb. 12, 2013.
Exhibit 1002 Patent File History U.S. Pat. No. 8,374,887.
Exhibit 1003, Declaration of Mr. Brian T. Hart from U.S. Pat. No. 8,374,887.
Exhibit 1004, Declaration of Wayne H. Grant from U.S. Pat. No. 8,374,887.
Exhibit 1005, 22 TAC §§291.20, 291.36, and 291.71-291.74 date issued Mar. 5, 2015 from U.S. Pat. No. 8,374,887.
Exhibit 1006 U.S. Pat. No. 6,711,460 Reese issued Mar. 23, 2004 from U.S. Pat. No. 8,374,887.
Exhibit 1009, Peterson et al., The North Dakota Telepharmacy Project: Restoring and Retaining Pharmacy Services in Rural Communities; the journal of Pharmacy Technology, vol. 20, No. 1, Jan./Feb. 2004—pp. 1-39 from U.S. Pat. No. 8,374,887.
Exhibit 1010, Declaration of Benjamin E. Weed from U.S. Pat. No. 8,374,887.
Exhibit 1011, Complaint—Alexander v. Baxter, (W.D.Texas 2014) filed Mar. 13, 2014 from U.S. Pat. No. 8,374,887.
Exhibit 1012, Charles F. Seifert et al., "The Training of a Telepharmacist: Addressing the Needs of Rural West Texas," American Journal of Pharmaceutical Education, 2004; 68 (3) Article 60—pp. 1-9 from U.S. Pat. No. 8,374,887.
Exhibit 1013, Assignment Emily H. Alexander to Becton, Dickinson and Company; U.S. Appl. No. 13/747,231; Reel 034110/Frame 0789 from U.S. Pat. No. 8,374,887.
Exhibit 1014, Exhibit A—Corrected Parties' Claims Construction Terms, Proposed Construction and cites Civil, 1:14cv-00222-LY— pp. 1-7 from U.S. Pat. No. 8,374,887.
Exhibit 1015, Information about Telepharmacy presentation 42503 and Presentation Telepharmacy at Texas Tech; Jon Phillips—1-27 from U.S. Pat. No. 8,374,887.
Exhibit 1017, Declaration of Dr. Roger W. Anderson in Support of Becton, Dickinson & Company's Response to Baxter's Motion for Summary Judgment of Invalidity Based Upon 35 U.S.C. § 101 filed Jan. 15, 2015 from U.S. Pat. No. 8,374,887.
Exhibit 1018, Plaintiff's Claim Construction Brief, 1:14-cv-222-LY filed Oct. 17, 2014 from U.S. Pat. No. 8,374,887.
Exhibit 1019, Plaintiff's Reply Claim Construction Brief, 1:14-cv-222-LY filed Nov. 7, 2014 from U.S. Pat. No. 8,374,887.
Exhibit 1020, The United States Pharmacopeia—the Official Compendia of Standards; 2004 from U.S. Pat. No. 8,374,887.
Exhibit 1021, Curriculum Vitae of Brian T Hart from U.S. Pat. No. 8,374,887.
Exhibit 1022, Curriculum Vitae of Wayne H Grant—Expert oversight— Expert Witness—Litigation Support from U.S. Pat. No. 8,374,887.
Exhibit 1023, Charles D Peterson et al., "The North Dakota Telepharmacy Project: Restoring and Retaining Pharmacy Services in Rural Communities," J Pharm Technol, 2004; vol. 20—pp. 028-039 from U.S. Pat. No. 8,374,887.
Exhibit 1025, Affidavit of Christopher Butler with attached Telemedicine Report Archive dated Mar. 4, 2015—6 pages from U.S. Pat. No. 8,374,887.
Exhibit 1026, Affidavit of Christopher Butler with attached presentation Telepharmacy at Text Tech—Jon Phillips dated Mar. 4, 2015—31 pages from U.S. Pat. No. 8,374,887.
Exhibit 1027, Order on Motion for Summary Judgment filed Aug. 3, 2015 from U.S. Pat. No. 8,374,887.
Exhibit 1028, Final Judgment filed Aug. 3, 2015 from U.S. Pat. No. 8,374,887.
Exhibit 1029 Charles Seifert from U.S. Pat. No. 8,374,887.
Exhibit 1030 Deposition of Charles Seifert Dec. 4, 2015 from U.S. Pat. No. 8,374,887.
Exhibit 1031 Deposition of Diane B. Ginsburg, PhD. Dec. 16, 2015 from U.S. Pat. No. 8,374,887.
Exhibit 1032 Texas Administrative Code, Title 22, Chapter 291, Subchapter A, Section 291.23 as in effect on Feb. 1, 2004 from U.S. Pat. No. 8,374,887.
Felkey, Bill G., "Integrating Technology at the Point of Care", Insight, Jan. 2004—pp. 8-10.
Formula for Patient Safety; ScriptPro; Aug. 17, 2003.
Fred Puckett, "Medication-management component of a point-of-care information system," Am. J. Health-Syst.Pharm., Jun. 15, 1995, pp. 1305-1309, vol. 52, American Society of Health-System Pharmacists, Inc.
"GE ImageQuant TL 7.0 Image Analysis Software" User Manual, May 2007, http://nba.uth.tmc.edu/Assets/pdf/otherityphoon-supporting-files/IQTL-UserManual.pdf, Uppsala, Sweden.
Gerald E. Meyer et al., "Use of bar codes in inpatient drug distribution," Am. J. Hosp. Pharm., May 1991, pp. 953-966, vol. 48, American Society of Hospital Pharmacists, Inc.
Ghent, Natale, "Pharmacists go digital to fight shortage", Pharmacy Practice 20.11 (Nov. 2004): 47—2 pages.
Gilad J. Kuperman, M.D. et al., "Innovations and research review: The impact of the HELP computer system on the LDS Hospital paper medical record," Topics in Health Record Management, 1991, pp. 76-85, vol. 12, Issue 2, Aspen Publishers, Inc.
"Global Med Announces First SAFETRACE TX™ Sale," Apr. 1, 1999, 2 pages.
Global Med Technologies, Inc. Introduces PeopleMed™.com, inc., A Chronic Disease Management Application Service Provider (ASP) Subsidiary, Jan. 11, 2000, 2 pages, Global med Technologies, Inc., Denver, CO.
Gretchen A. Barry et al., "Bar-code technology for documenting administration of large-volume intravenous solutions," American

(56) References Cited

OTHER PUBLICATIONS

Journal of Hospital Pharmacy, Feb. 1989, pp. 282-287, vol. 46, American Society of Hospital Pharmacists.
H. Paul Hammann et al., "A World Wide Web Accessible Multi-Species ECG Database," 1997, pp. 7-12, ISA.
Halverson, Daniel R. IsoRx: TelePharmacy Software presentation—23 pages.
Henry J. Lowe et al., "WebReport: A World Wide Web Based Clinical Multimedia Reporting System," 1996, pp. 314-318, AMIA, Inc.
"Hospitals battle errors with bar codes," Mar. 24, 2004, 3 pages, MSNBC.
Howard L. Bleich et al., "Clinical Computing in a Teaching Hospital," Use and Impact of Computers in Clinical Medicine, 1987, pp. 205-223 and selected pages, Springer-Verlag, New York, NY.
http://isorx.com/ Jan. 29, 2004.
http://www.scriptpro.com/products//sp-200/main.htm, Feb. 13, 2004, Product listing for SP 200® Robotic Prescription Dispensing System.
http://www.scriptpro.com/products/space/space200.htm, Feb. 10, 2004, Product listing for SP Automation Center 200TM (Space 200TM) Prescription Dispensing Automation Center.
Hughes, Shirley, " Bedside Terminals: Clinicom," Clinical Computing, Jan./Feb. 1988, pp. 22-28, vol. 5, No. 1.
IPR Decision Paper No. 8 Entered Aug. 13, 2015 from U.S. Pat. No. 8,374,887.
IPR Final Written Decision Paper No. 29 Entered Jul. 11, 2016 from U.S. Pat. No. 8,374,887.
James Kazmer et al., "The Creation of Virtual Electronic Medical Record," 1996, 17 pages.
Jennifer Langham; "Taking Automation to New Levels," Insight, the QS/1 Magazine, Oct. 2002; pp. 2-5.
John Frady; "What's New in RxCare Plus 17.2," Insight, the QS/1 Magazine, Apr. 2002; pp. 2-3, 14.
Jones, et al., "Use of a remote computerized system for study documentation in clinical trials" Drug Information Journal, Oct.-Dec. 1998, vol. 32, No. 4 oe pp. 1153-1163.
Karen E. Bradshaw et al., "Physician decision-making—Evaluation of data used in a computerized ICU," International Journal of Clinical Monitoring and Computing, 1984, pp. 81-91, vol. 1, Martinus Nijhoff Publishers, Netherlands.
Kastango, Eric S. and Bradshaw, Brian D., "USP chapter 797: Establishing a practice standard for compounding sterile preparations in pharmacy" Am J Health-Syst Pharm., Sep. 15, 2004, vol. 61—pp. 1928-1938.
Kenneth N. Barker et al., "Effect of an automated bedside dispensing machine on medication errors," American Journal of Hospital Pharmacy, Jul. 1984, pp. 1352-1358, vol. 41, No. 7, American Society of Hospital Pharmacists.
Keeys, Christopher A. et al., "Providing nighttime pharmaceutical services through telepharmacy" Am J Health-Syst Pharm, Apr. 15, 2002, vol. 59—pp. 716-721.
Khan, Shamima et al., "Is There a Successful Business Case for Telepharmacy?" Telemedicine and e-Health, vol. 14, No. 3, Apr. 2008, pp. 235-245.
Kimber, Michael B. et al., "Telepharmacy-Enabling Technology to Provide Quality Pharmacy Services in Rural and Remote Communities" Journal of Pharmacy Practice and Research, vol. 36, No. 2, 2006—128-133.
Kodak DirectView PACS—Rural Hospital Joins the Big Leagues PACS/Enterprise Information management (EIM) Solution—www.kodak.com/go/medical—4 pages.
Kosub, David, "Device allows pharmacy care in remote areas" Pharmacy Practice, vol. 20, No. 10, Oct. 2004—pp. 12-13.
Koutnik, Eileen, Assistnat Editor, Pharmacy Times, "The Pharmacy of Tomorrow" Pharmacy Times, Aug. 1, 2003—3 pages.
Larry B. Grandia, B.S.E. et al., "Building a computer-based patient Record System in an Evolving Integrated Health System," First Annual Nicholas E. Davies Award Proceedings of the CPR Recognition Symposium, 1995, pp. 19-55, Computer-based Patient Record Institute, Inc., Bethesda, MD.
Lefkowitz, Sheldon et al., "A Trial of the Use of Bar Code Technology to Restructure a Drug Distribution and Administration System," 1991, pp. 239-242, Hospital Pharmacy, vol. 26.
LP, "ATM-STyle Drug Dispensers Taking Hold in Areas With Limited Pharmacist Services" Pharmacy Practice News, Jan 2004, vol. 31, No. 1—4 pages.
"The Longitudinal Clinical Record: A View of the Patient," taken from Proceedings of the 1994 Annual HIMSS Conference, Feb. 14, 1994, pp. 239-250, Healthcare Information and Management Systems Society, Chicago, Illinois, USA.
Lustig, Ahuva, "Medication error prevention by pharmacists—An Israeli solution" Pharmacy World & Science, 2000, vol. 22, No. 1—pp. 21-25.
Medicaid Memo—Department of Medical Assistance Services (Converting NDCs from 10-digits to 11-digits) May 31, 2007.
Medcin® Technical Overview, undated, 111 pages, Medicomp Systems.
Michael H. Mackin, "Impact of Technology on Environmental Therapeutic Device Design," Medical Instrumentation, Feb. 1987, pp. 33-35, vol. 21, No. 1, Association for the Advancement of Medical Instrumentation.
Michelle M. Casey, M.S., Jill Klingner, R.N., M.S., and Ira Moscovice, Ph.D.; "Access to Rural Pharmacy Services in Minnesota, North Dakota, and South Dakota," Working Paper Series, Jul. 2001, #36.
Monane et al., "Improving Prescribing Patterson for the Elderly Through an Online Drug Utilization Review Intervention", JAMA, Oct. 14, 1998, vol. 280, No. 14—pp. 1249-1252.
Morris, Aisha M., Schneider, Philip J., Pedersen, Craig A. and Mirtallo, Jay M. "National survey of quality assurance activities for pharmacy-compounded sterile preparations" Am J Health-Syst Pharm, Dec. 15, 2003, vol. 60—pp. 2567-2576.
Murray, Michael D. et al. "Effects of Computer-based Prescribing on Pharmacist Work Patterns" Journal of the American Medical Informatics Association, Nov./Dec. 1998, vol. 5, No. 6—pp. 546-553.
Napoli, M. et al., "Picture archiving and communication in radiology", Rays. Jan.-Mar. 2003—PubMed—NCBI http://www.ncbi.nlm.m=nih.gov/pubmed/14509181—Abstract.
Nissen et al., Can telepharmacy provide pharmacy services in the bush, School of Pharmacy, University of Queensland, Brisbane, Australia, Journal of Telemedicine and Telecare 2003, vol. 9 (Suppl. 2): S2:39-41.
North Dakota Century Code Statute Law—State Board of Pharmacy—219 pages.
Parks, Liz, "Annual report of retail pharmacy: Using central-fill to maximize dispensing" Drug Store News, Aug. 20, 2001 vol. 24, No. 11—pp. 51, 75.
Parsons, et al., "Digital Media—Can I Change a Graphic's File Size?", New Perspectives on Computer Concepts—Course Technology, 2011, Cengage Learning, Boston, MA.
Paul H. Perlstein et al., "Computer-Assisted Newborn Intensive Care," Pediatrics, Apr. 1976, pp. 494-501, vol. 57, No. 4, American Academy of Pediatrics, Inc., Evanston, Illinois.
Paul H. Perlstein et al., "Future Directions for Device Design and Infant Management," Medical Instrumentation, Feb. 1987, pp. 36-41, vol. 21, No. 1, Association for the Advancement of Medical Instrumentation.
PCA II Multi-Mode Cartridge Operator's Manual, Sep. 1995, approx. 40 pages, Baxter Healthcare Corporation, Deerfield, IL.
Pesce, James, "Bedside Terminals: Medtake," Clinical Computing, Jan. /Feb. 1988, pp. 16-21, vol. 5, No. 1.
Peter Lord et al., MiniMed Technologies Programmable Implantable Infusion System, Annals New York Academy of Science, pp. 66-71, describing clinical trials from Nov. 1986.
Peterson et al., The North Dakota Telepharmacy Project Restoring and Retaining Pharmacy Services in Rural Communities—Presentation North Dakota State University, Fargo, North Dakota.
Petition for Inter Partes Review *Baxter International Inc.* v. *Becton, Dickinson and Company* for U.S. Pat. No. 8,374,887, pp. 1-69.

(56) References Cited

OTHER PUBLICATIONS

Pharmacy Automation ONLINE Vendors Page; Internet Archive Wayback Machine; http://pharmacyautomation.com/vendors.html—3 pages.
Pharmacy Data Management (PDM) Technical Manual/Security Guide Version 1.0, Sep. 1997—55 pages.
Pharmacy education and practice out of sync? (Roundtable) Chain Drug Review, vol. 25, No. 6, Mar. 17, 2003, RX2 (6).
Prem S. Chopra, Virgil A. Thomason, and Dell M. Stinett; "Voice-Activated Networked Workstation for a Physically Disabled Physician," 10-7803-2050-6/94 1994 IEEE, pp. 478-479.
Product literature, Baxter Healthcare Corporation, "Flo-Gard® 6201 Volumetric Infusion Pump," 1992, 2 pages.
Product literature, Baxter Healthcare Corporation, "MultiPlex™ Series 100 Fluid Management System," 1988, 2 pages.
Product literature, Baxter Healthcare Corporation, "MultiPlex™ Series 100 Fluid Management System," undated, 2 pages.
Remote Dispensing Regulations, NABPLAW Sep. 2003.
Woodall, Sandra C., Remote Order Entry and Video Verification; Reducing After-Hours Medication Errors in a Rural Hospital; S. Woodall; Joint Commission on Accreditation of Healthcare Organizations; vol. 30; No. 8; Aug. 2004.
Rich Muller; "NRx QS/1's Premium Pharmacy Software," Insight, the QS/1 Magazine, Jul. 2003; pp. 2-3, 12-15.
Rouse, et al., Academy of Managed Care Pharmacy et al., "White paper on pharmacy technicians 2002: Needed changes can no longer wait" Am J Health-Syst Pharm, Jan. 1, 2003, vol. 60—pp. 37-51.
Rule Section 291.36—Class A Pharmacies Compounding Sterile Pharmaceuticals—1 page.
Schrenker, Richard and Cooper, Todd, "Building the Foundation for Medical Device Plug-and-Play Interoperability".
Seifert et al.; "The Training of a Telepharmacist: Addressing the Needs of Rural West Texas," American Journal of Pharmaceutical Education 2004; 68 (3) Article 60. Jul. 16, 2004.
Standard Specification for Transferring Clinical Laboratory Data Messages Between Independent computer Systems, Annual Book of ASTM Standards, Mar. 25, 1988, pp. 1-16, E 1238-88, Global Engineering Documents, Philadelphia, PA.
Standard Specification for Transferring Clinical Observations Between Independent Computer Systems, Annual Book of ASTM Standards, Jun. Mar. 1994, pp. 132-210, E 1238-94, Philadelphia, PA.
Standard Specification for Transferring Clinical Observations Between Independent Computer Systems, Aug. 10, 1997, 79 pages, ASTM E 1238-97, West Conshohocken, PA, United States.
Standard Specification for Transferring Information Between Clinical Instruments and Computer Systems, Annual Book of ASTM Standards, Jun. 1991, 15 pages, E 1394-91, Philadelphia, PA.
Suzanne Carter, RN, Ed.D. et al., "The Computer-based Patient Record: The Jacobi Medical Center Experience," Second Annual Nicholas E. Davies Award Proceedings of the CPR Recognition Symposium, 1996, pp. 71-95, Computer-based Patient Record Institute, Inc., Bethesda, MD.
T. Allan Pryor et al., "help—A Total Hospital Information System," Proceedings of the Fourth Annual Symposium on Computer Applications in Medical Care, Nov. 2-5, 1980, pp. 3-7, vol. 1, Institute for Electrical and Electronics Engineers, New York, NY.
T.E. Bozeman et al., "The Development and Implementation of a Computer-Based Patient Record in a Rural Integrated Health System," Third Annual Nicholas E. David Award Proceedings of the CPR Recognition Symposium, 1997, pp. 101-130, Computer-based Patient Record Institute, Inc., Bethesda, MD.
"Telepharmacy project expands students' practice experience" Telemedicine Report, vol. 6, No. 1, Jan. 2004 oe 4 pages.
The World's First Fully Integrated Workflow Manager for I.V. Rooms, IntelliFlowRx Brochure, For Health Technologies Inc,. United States, May 2008.
Title 22. Examining Boards, 22 TAC Section 1.161; texinfo.library.unt.edu/Texasregister/html/2001/sep-14/PROPOSED/22.EXAMING BOARDS.html—Sep. 20, 2014, pp. 1-70.
Ukens, Carol, "Pharmacist shortage boosts telepharmacy" Drug Topoics, Jun 3, 2002; 146, 11—p. 53.
Valeriy Nenov et al., "Remote Analysis of Physiological Data from Neurosurgical ICU Patients," Journal of the American Medical Informatics Association, Sep./Oct. 1996, pp. 318-327, vol. 3, No. 5.
"Victor J. Perini et al.,""Comparison of automated medication-management systems,: Am. J. Hosp. Pharm., Aug. 1, 1994, pp. 1883-1891, vol. 51, American Society of Hospital Pharmacists, Inc.".
Vincenzo Della Mae et al., "HTML generation and semantic markup for telepathology," Computer Networks and ISDN Systems, 1996, pp. 1085-1094, vol. 28, Elsevier Science B.V.
Website information for Cartharsis Medical Technology Products, Dec. 9, 2001, 15 pages.
Website information for MedPoint™, Mar. 13, 2003, 20 pages, Bridge Medical, Solana Beach, CA.
William R. Dito et al., "Bar codes and the clinical laboratory: adaptation perspectives," Clinical Laboratory Management Review, Jan./Feb. 1992, pp. 72-85, Clinical Laboratory Management Association, Inc.
Wills, Robert D., "Drug Images and Drug Imprints" Insight, Apr. 2001—p. 7.
Yvonne Mari Abdoo, "Designing a Patient Care Medication and Recording System that Uses Bar Code Technology," Computers in Nursing, May/Jun. 1992, pp. 116-120, vol. 10, No. 3.
Jon Phillips, Telepharmacy at Texas Tech, PowerPoint, Jan. 26, 1997, https://web.archive.org/web/20040509162423/http://www.ttuhsc.edu/telemedicine/Powerpoint/Telepharmacy%20presentation%2042503.ppt.
A.H. McMorris et al. "Are Process Control Rooms Obsolete?", Control Engineering, pp. 42-47, Jul. 1971.
Standard Specification for Transferring Clinical Observations between Indepdendent Computer Systems, Annual Book of ASTM Standards, Nov. 14, 1991, pp. 1-64, ASTM E 1238-91,Philadelphia, PA.
Standard Specification for Transferring Information Between Clinical Instruments and Computer Systems, Dec. 10, 1997; 15 pages, ASTM E 1394-97, West Conshohocken, PA, United States.
Web site information, Information Data Management, Inc.'s PCMS: Plasma Center Management System, Dec. 14, 2001, 11 pages.
Web site Information, Wyndgate Technologies' SafeTrace Tx™, undated, 15 pages.
Specification for Low-Level Protocol to Transfer Messages Between Clinical Laboratory Instruments and Computer Systems, Mar. 11, 1991; 7 pages, ASTM E 1381-91, Philadelphia, PA, United States.
Atherton, H.D., Dollberg, S., Donnelly, M.M., Perlstein, P. H. Roath, S.B., "Computerized Temperature Control of the Low-Birth-Weight Infant: A 20-Year Retrospective and Future Prospects," Biomedical Instrumentation and Technology, Jul./Aug. 1994, pp. 302-309, vol. 28 No. 4.
Friesdorf, W., Grob-Alltag, F., Konichezky, S., Schwilk, B., Fattroth, A., Fett, P., "Lessons learned while building an integrated ICU workstation," International Journal of Clinical Monitoring and Computing, 1994, pp. 89-97, vol. 11.
Gammon, K., Robinson, K., "Bedside Data System Aids Pharmacy," Computers in Healthcare, Dec. 1988, pp. 3537, vol. 9 No. 12.
Graseby 3100 Syringe Pump, Graseby Medical Ltd., A Cambridge Electronic Industries Company, England, 2 pages.
Kampmann, J., Lau, G., Kropp, ST., Schwarzer, E., Hernandez Sande, C., "Connection of electronic medical devices in ICU according to the standard 'MIB'," International Journal of Clinical Monitoring and Computing, 1991, pp. 163-166, vol. 8.
Angaran, "Telemedicine and telepharmacy: Current status and future implications", Am J Health-Syst Pharm, vol. 56, Jul. 15, 1999 (32 pages).
Carson, Ewart et al., "A Systems Methodology for the Development and Evaluation of a Telematic Home Haemodialysis Service," Proceedings—19th International Conference—IEEE/EMBS Oct. 30-Nov. 2, 1997, Chicago, Illinois, pp. 907-910.

* cited by examiner

DOSE PREPARATION DATA ANALYTICS

CROSS-REFERENCE TO RELATED APPLICATION

This application claims priority from U.S. Provisional Application No. 62/088,358 filed on Dec. 5 2014 entitled "DOSE PREPARATION DATA ANALYTICS," the contents of which are incorporated by reference herein as if set forth in full.

FIELD

The present disclosure generally relates to the field of healthcare data management and in particular to facilitating data analytics for use with dose order record information such that specific, limited access to a multidimensional repository of data is provided, for example, based on a facility corresponding to a user of the tool and data related to the facility.

BACKGROUND

Healthcare facilities such as hospitals or the like often provide dose order information to a pharmacy in connection with a request to prepare a dose order record for administration to a patient. Traditional approaches to processing the dose orders received at a pharmacy included, for instance, printing physical labels for each dose order to be prepared. In turn, any activity in the pharmacy in relation to the dose orders was premised on the use of the physical labels for workflow management. In addition to the susceptibility for such physical labels to be lost, misplaced, or confused, the ability for pharmacy staff to organize, manage, or communicate the dose orders represented by the physical labels was limited.

In addition to the limitations of traditional approaches in connection with the preparation of dose orders at a pharmacy, the ability to quantify, track, and otherwise review pharmacy activity after preparation of the dose orders was also limited. For instance, the use of physical labels, which would be attached to the dose order upon completion of the preparation, left no means for logging or auditing the activities performed in the pharmacy in relation to specific dose orders absent tedious manual recordation of pharmacy work. Manual recordation of pharmacy work is time consuming, prone to error, and unreliable, and thus does not present a viable option for quantifying, tracking, and reviewing pharmacy activity. In turn, valuable information in relation to the activity of the pharmacy was not visible to pharmacy or hospital management.

Pharmacy workflow management applications have been developed to assist in the preparation, tracking, organization, and documentation of dose orders that are to be prepared or have been prepared by a pharmacy or the like. For example, co-owned U.S. patent application Ser. No. 14/022,415 entitled "MANAGEMENT, REPORTING AND BENCHMARKING OF MEDICATION PREPARATION" filed on Sep. 10, 2013, the entirety of which is incorporated by reference in its entirety. In this regard, dose order records that include received and/or appended dose order information and/or dose order metadata may be generated and stored at a facility that prepares dose orders for administration to a patient. Additionally such dose order records may be stored at a central server that is in operative communication with a plurality of facilities. In this regard, dose order records from a plurality of facilities may be collectively stored at the central server (e.g., for purposes related to data back up or the like).

SUMMARY

In view of the foregoing, it has been recognized that dose order information from a plurality of facilities that is stored at a central location (e.g., a central server) may be advantageously utilized to provide reporting, metrics, or the like with respect to the stored data related to one or more facilities. Specifically, a data analytics tool may be provided that is in operative communication with the central server that may access the data stored at the central server to provide data analytics (e.g., dynamic reports or the like). As the data analytics tool may access the data at the central server, such analytics may be provided in relation to one or more facilities without each individual facility having to maintain an interface to the data analytics tool. However, as the data at the central server may include data from a plurality of different facilities, it has also been recognized that providing selective access to such report may advantageously allow for centralized application of a data analytics tool while maintaining security and restricted access to individuals from respective ones of the facilities when accessing data at the central server.

As such, the present disclosure describes healthcare data management that provides the ability to provide data analytics tools for use in relation to multidimensional data regarding dose order records. Specifically, the present disclosure contemplates allowing selective access to a multidimensional data set. For instance, dose order records from a plurality of facilities may be collectively stored as a multidimensional data set. A base data cube class definition may be generated that uses an identification of a user accessing the tool to determine a subset of the records to which the user has access. In this regard, the base cube class definition may have a data dimension that allows the filtering of data records for presentation to a user in a dynamically generated report. In this regard, additional data cube class definitions may inherit from the base data cube class definition so that a user may only retrieve report data corresponding to data to which they are authorized for access.

In this regard, a first aspect includes a method for providing a user selective access to a data analytics tool for processing a multidimensional data set corresponding to dose order records for use in providing data analytics to the user regarding a subset of the dose order records of the multidimensional data set. The method includes storing a multidimensional data set comprising information corresponding to a plurality of dose order records. The plurality of dose order records of the multidimensional data set comprises at least one indication of a facility corresponding to the dose order records. The multidimensional data set comprises dose order records corresponding to a plurality of facilities. The method further includes receiving user information from a user at one of the plurality of facilities. The user information is indicative of a given facility from which the user is accessing a data analytics tool. The method also includes providing the data analytics tool access to the multidimensional data set to generate a dynamically generated report regarding a subset of the multidimensional data set corresponding to the given facility from which the user is accessing the data analytics tool. Additionally, the method includes presenting to the user at a user interface the dynamically generated report regarding the subset of the multidimensional data set corresponding to the given facility from which the user is accessing the data analytics tool.

A number of feature refinements and additional features are applicable to the first aspect. These feature refinements and additional features may be used individually or in any combination. As such, each of the following features that will be discussed may be, but are not required to be, used with any other feature or combination of features of the first aspect.

For instance, in an embodiment the data analytics tool may include a plurality of data cube class definitions applicable to the multidimensional data set to generate the dynamically generated report. The plurality of data cube class definitions may include a base cube class definition from which all others of the plurality of data cube class definitions depend. The base cube class definition may include at least one data dimension related to the at least one indication of a facility corresponding to the dose order records. In turn, the method may include applying the base cube class definition to the multidimensional data set based on the user information indicative of a given facility from which the user is accessing the data analytics tool and building a data cube based on the applying that limits the data accessible by the user to the subset of the multidimensional data set corresponding to the given facility from which the user is accessing the data analytics tool.

In an embodiment, the building may include performing at least one data transformation operation on the subset of the multidimensional data set, wherein the at least one data transformation operation is defined in the base cube class definition. The at least one data transformation may include automatically transcribing a first data field for each given dose order record in the subset with a second data field of the respective ones of the dose order records of the subset. The at least one data transformation may be applied only to a given type of dose order records. The type of dose order records may be total parenteral nutrition (TPN) doses, the first data field may be a dose description field, and the second field may be a drug name field for the given dose.

In an embodiment, the method may further include invoking another of the data cube class definitions depending from the base cube class definition for application to the subset of the multidimensional data set corresponding to the given facility from which the user is accessing the data analytics tool to generate the dynamically generated report regarding the subset of the multidimensional data set. In certain applications, the plurality of data cube class definitions may include a parameter indicative of whether data cubes built using the data cube class definitions include protected health information (PHI). The parameter may be dynamically generated based on at least one dimension of the data cube class definition.

In an embodiment, the receiving may include receiving login information at a local server resident at the facility from which the user is accessing the data analytics tool to initiate a user session, authenticating the user to a central server based on the login information received at the local server, and populating a session variable related to the user session based on authenticated user login information. The session variable may include the user information indicative of the given facility from which the user is accessing the data analytics tool. In this regard, the method may include a delegated authentication process that may, in at least some applications, include passing a token at least partially based on the session variable to the data analytics tool. The token may be compared to available tokens at the central server to determine if the user is to be granted access to the data analytics tool. Accordingly, upon matching the token to one of the available tokens, the token may be issued to the user and the corresponding available token is removed from the central server. In some applications, the session variable includes a role definition for the user generated based at least in part on the login information received by the user. The role definition may include indications as to the ability of the user in relation to viewing reports, editing reports, viewing cube class definitions, editing cube class definitions, viewing pivot tables, editing pivot tables, viewing dashboards, and editing dashboards.

The method may further include logging user activity in relation to the use of the data analytics tool by the user. The logging may include recording information regarding the user and the usage of the data analytics tool by the user. The logging may include recording the identity of the dynamically generated report presented to the user. The logging may include recording whether the dynamically generated report presented to the user contained protected health information (PHI). The multidimensional data set may include data regarding the identity of doses, data regarding the steps of preparing the doses, data regarding the timing of doses, data regarding errors that occurred during dose preparation, data regarding product waste, data regarding drug usage, data regarding drug therapies administered, and data regarding drug interactions.

A second aspect includes a system for implementation of a data analytics tool for processing a multidimensional data set corresponding to dose order records for data analytics regarding a subset of the dose order records of the multidimensional data set. The system includes a central server that is in operative communication with a plurality of local servers, each of the local servers being disposed at a corresponding respective facility that prepares doses corresponding to dose orders for administration to a patient. The central server receives information regarding dose order records corresponding to the dose orders from the local servers. The system also includes a database at the central server that stores a data structure comprising a multidimensional data set including a plurality of dose order records received from the plurality of local servers. Each of the plurality of dose order records of the multidimensional data set comprises at least one indication of the facility from which the dose order record was received. The system may also include a local server interface in operative communication with the plurality of local servers for receiving from at least one of the plurality of local servers user information from a user at one of the plurality of facilities. The user information is indicative of a given facility from which the user is accessing a data analytics tool. The system also includes a data analytics interface that facilitates operative communication with a data analytics tool. The data analytics interface provides a data analytics tool access to the multidimensional data set stored in the database to generate a dynamically generated report regarding a subset of the multidimensional data set corresponding to the given facility from which the user is accessing the data analytics tool based on the user information received from the local server interface. The system also includes a user interface for presenting to the user at a user interface the dynamically generated report regarding the subset of the multidimensional data set corresponding to the given facility from which the user is accessing the data analytics tool.

A number of feature refinements and additional features are applicable to the second aspect. These feature refinements and additional features may be used individually or in any combination. As such, each of the features discussed above in connection with the first aspect may be, but are not required to be, used with any other feature or combination of features of the second aspect.

A third aspect includes a system for providing a user selective access to a data analytics tool for processing a multidimensional data set corresponding to dose order records for use in providing data analytics to the user regarding a subset of the dose order records of the multidimensional data set. The system includes a central server that is in operative communication with a plurality of local servers, each of the local servers being disposed at a corresponding respective facility that prepares doses corresponding to dose orders for administration to a patient. The central server receives information regarding dose order records corresponding to the dose orders from the local servers. The system also includes a database at the central server that stores a data structure comprising a multidimensional data set including a plurality of dose order records received from the plurality of local servers. Each of the plurality of dose order records of the multidimensional data set comprises at least one indication of the facility from which the dose order record was received. The system also includes a local server interface in operative communication with the plurality of local servers for receiving from at least one of the plurality of local servers user information from a user at one of the plurality of facilities. The user information is indicative of a given facility from which the user is accessing a data analytics tool. The system also includes a data analytics tool in operative communication with the database for access to the multidimensional data set stored in the database to generate a dynamically generated report regarding a subset of the multidimensional data set corresponding to the given facility from which the user is accessing the data analytics tool based on the user information received from the local server interface. The system also includes a user interface for presenting to the user at a user interface the dynamically generated report regarding the subset of the multidimensional data set corresponding to the given facility from which the user is accessing the data analytics tool.

A number of feature refinements and additional features are applicable to the third aspect. These feature refinements and additional features may be used individually or in any combination. As such, each of the features discussed above in relation to the first aspect may be, but are not required to be, used with any other feature or combination of features of the third aspect.

DETAILED DESCRIPTION

The following description is not intended to limit the invention to the forms disclosed herein. Consequently, variations and modifications commensurate with the following teachings, skill and knowledge of the relevant art, are within the scope of the present invention. The embodiments described herein are further intended to explain modes known of practicing the invention and to enable others skilled in the art to utilize the invention in such, or other embodiments and with various modifications required by the particular applications(s) or use(s) of the present invention.

Figure 1:
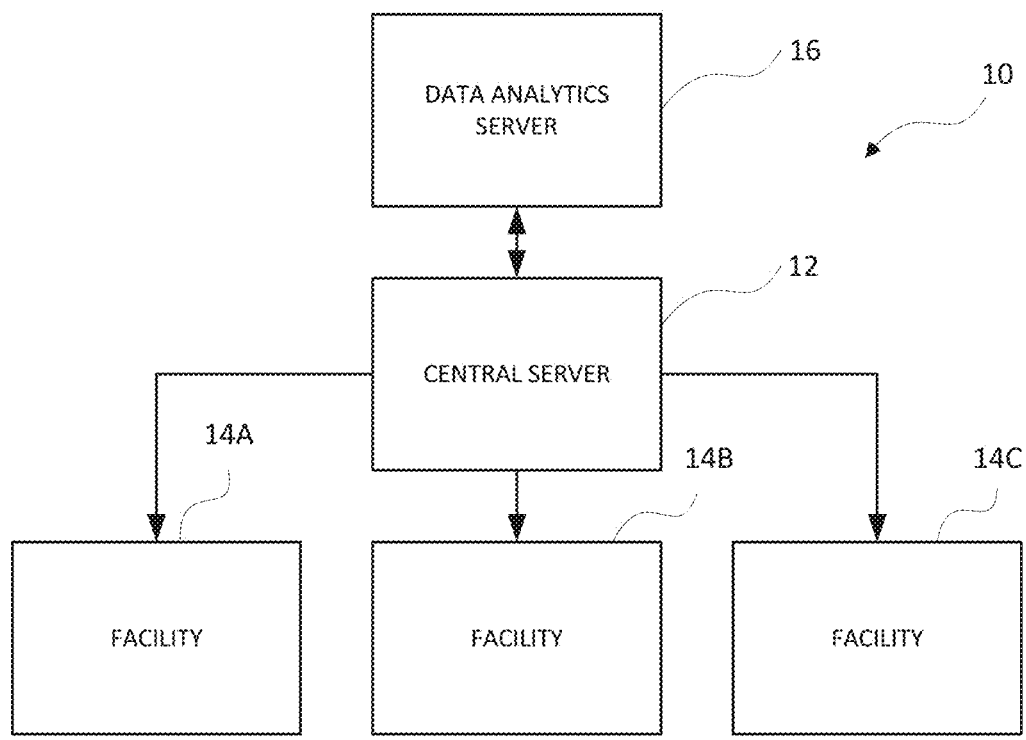
FIG. 1 is a schematic view of an embodiment of a system for selective, secure data analytics in relation to an aggregated multidimensional data set from a plurality of facilities.

With reference to FIG. 1, a system 10 that facilitates selective, secure data analytics in a distributed environment as described herein is depicted. The system 10 may include a central server 12. The central server 12 may be in operative communication with a plurality of facilities 14. For instance, as shown in FIG. 1, the central server 12 may be in operative communication with a first facility 14A, a second facility 14B, and a third facility 14C. While three facilities 14A, 14B, and 14C are shown in FIG. 1 for purposes of illustration, it will be understood that fewer or additional facilities 14 may be provided in operative communication with the central server 12 and the three facilities 14A-14C depicted in FIG. 1 are for illustrative purposes only.

Accordingly, in at least one embodiment, the facilities 14 may comprise unaffiliated and discrete healthcare facilities 14 capable of preparing medication doses for administration to patients. The central server 12 may be hosted by another discrete and unaffiliated third-party that may be separate from any of entities of the facilities 14. For instance, the central server 12 may be hosted and/or executed by an application provider that provides one or more client applications for execution by the facilities 14 to facilitate a pharmacy workflow management application. Specifically, the central server 12 may be executed or hosted by an application provider that provides the pharmacy workflow management application each facility 14.

As such, the facilities 14A, 14B, and 14C may execute a pharmacy workflow management application that may allow for the facilities 14A, 14B, and 14C to receive, process, organize, prepare, track, or otherwise manage dose orders to be prepared at each of the respective facilities 14A, 14B, or 14C. In this regard, each facility 14 may generate dose order information related to dose orders processed at each respective one of the facilities 14. In turn, facilities 14 may be in operative communication with the central server 12 and may provide dose order data to the central server 12.

In this regard, dose order data may include any one or more classes of information regarding dose orders processed. For instance, the dose order data may include information corresponding with the dose order received at the pharmacy (e.g., including information entered by way of a physician order entry (POE) system, received by a pharmacy information system (PhIS), or the like). The dose order data may also include data appended to and/or generated in connection with the preparation of a dose order. This information may include data related to the products (e.g., drug products, pharmacy products, or hardware) used to prepare the dose order. As such, the information may include information regarding one or more drugs (or all drugs) used to prepare the dose such as a national drug code (NDC), a lot number, and expiration, etc. The information may also include preparation metadata such as information related to the identity of personnel taking action with respect to a dose, time events related to a dose, images associated with dose preparation and/or verification, errors that were detected or occurred during dose processing, information related to a pharmacist review of a dose, tracking information regarding a dose in the pharmacy and/or administration environment, etc. In short, the dose order data may comprise any information regarding the dose order or preparation of the dose order that is recorded, generated, appended, or otherwise associated with the dose order.

Additionally, a data analytics server 16 may be operative communication with the central server 12. As will be discussed in greater detail below, the data analytics server 16 may comprise a data analytics tools that may be applied to data at the central server 12 to generate, for example, dynamically generated reports for use in data analytics with respect to the data to which the data analytics tool is applied at the central server 12. The data analytics tool may include data cube class definitions that define data organization and transactions carried out with respect to data to facilitate generation of dynamic reports for use in data analytics. Such data cube class definitions are described in greater detail below. In any regard, it may be appreciated that the data cube class definitions may be applied to data at the central server 12 to facilitate data analytics with respect to the data to which the data cube class definitions provided by the data analytics tool as applied.

As such, users from each respective facility 14 may be operative to access the data analytics tool provided by the analytics server 16 to invoke the data analytics tool for use in connection with data stored on the central server 12. As outlined briefly above, while provision of the data analytics server 16 in operative communication with the central server 12 may simplify the interface complexity of the system 10 (e.g., in contrast providing a data analytics server connection directly to each facility), the interface with a central server 12 may result in the need to provide selective, secure access to the data stored in the central server 12. Specifically, as the central server 12 may store data from a plurality of facilities 14, it may be that users from a given facility (e.g., the first facility 14A) should not be provided access to data from other facilities (e.g., the second facility 14B or third facility 14C). That is, selective access to users may be provided such that users of a given facility may only be provided access to data analytics with respect to data for the facility from which the user is accessing the data analytics tool. In this regard, the system 10, as described in greater detail below, may provide selective, secure access to a data analytics tool with respect to a portion of data specific to the facility 14 from which the data analytics tool is accessed.

While the following disclosure mentions providing selective access on a facility by facility basis by determining a facility from which a user is accessing the data analytics tool, it may be appreciated that a user accessing the tool from a given facility may be an organizational user. That is, a plurality of facilities may comprise an organization. As such, a user accessing the tool from a given one of the facilities comprising the organization may have credentials sufficient access data from the plurality of facilities comprising the organization. Thus while potentially referenced herein as a facility by facility determination of access to data, the system may be executed such that any data at the central server may be analyzed using the data analytics tool so long as a user accessing the tool has sufficient credentials to view the data and utilize the tool.

Figure 2:
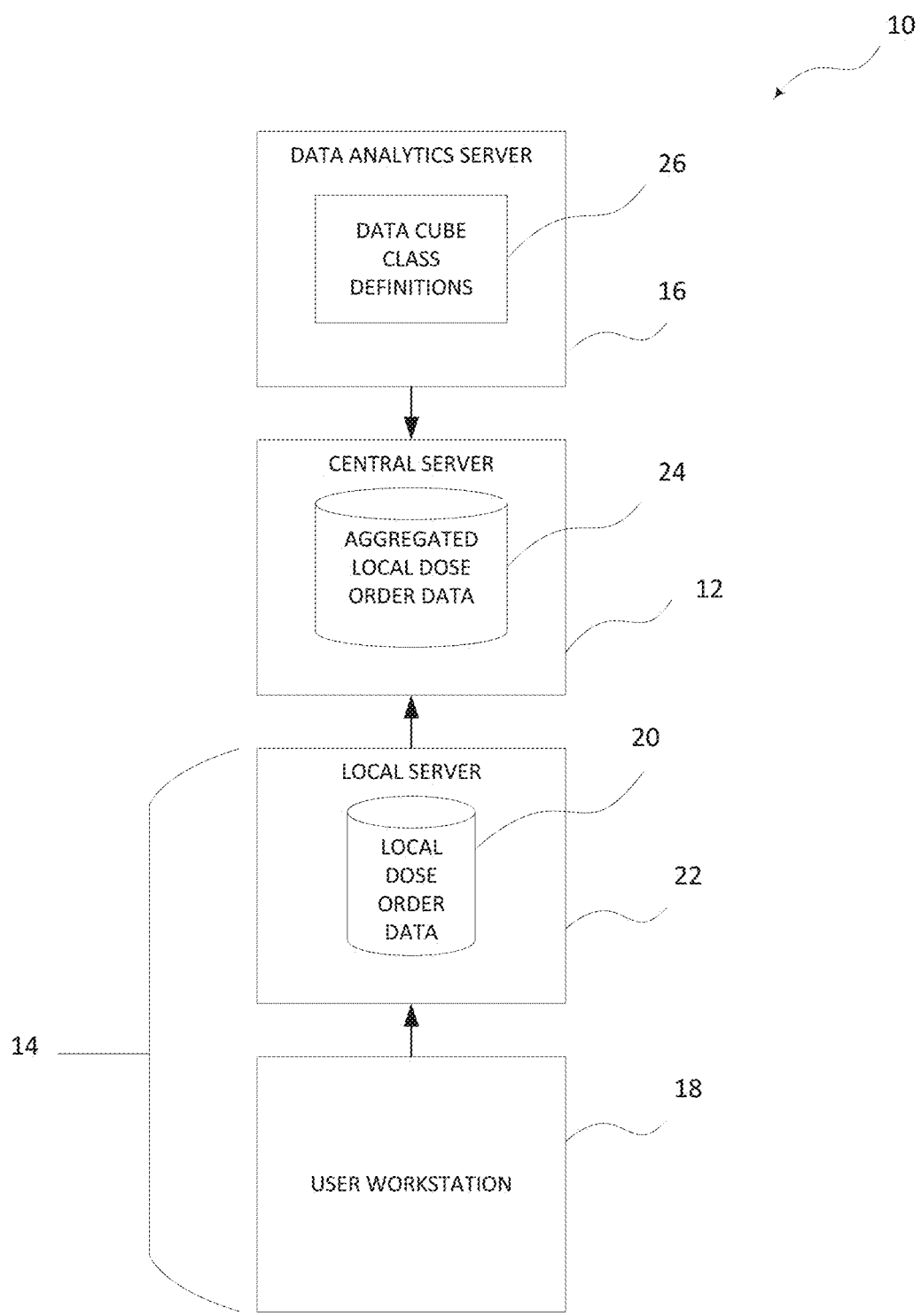
FIG. 2 is a schematic view of an embodiment of a data flow in relation to an example facility relative to the system of FIG. 1.

FIG. 2 further depicts a schematic view of the system 10 that illustrates information flow between portions of the system 10. In FIG. 2, a user workstation 18 and local server 22 may be provided at each instance of a facility 14. While a single instance of the facility 14 is depicted in FIG. 2, it may be appreciated that, in connection with the disclosure of FIG. 1, a plurality of facilities 14 each having a user workstation 18 and local server may undergo a similar information flow is that described with respect to the given facility 14 depicted in FIG. 2. Furthermore, while single user workstation 18 is depicted in operative communication with the local server 20, it may be appreciated that a plurality of user workstations 18 may be provided in operative communication with the local server 20 and may generally follow the description provided herein. The user workstation 18 may be in operative communication with the local server 20 and may exchange dose order data between the user workstation 18 the local server 20. This data exchange may include exchange of dose order information between a local dose order data repository 22 (e.g., stored in a database or the like at the local server 20) and the user workstation 18. This may facilitate provision of dose order information to the user workstation 18 for use in preparation of doses, generation or capture of dose order information, review of prepared dose orders by a pharmacist, or other activities provided by a pharmacy workflow manager.

The local dose order data 22 may be provided from the local server 20 to the central server 12. In this regard, the central server 12 may store aggregated local dose order data 24. For instance, the aggregated local dose order data 24 may include dose order data received a plurality of facilities as illustrated in FIG. 1. As may be appreciated, the dose order data at the aggregated local dose order data 24 may include an indicator as to the facility (or organization) from which the data 24 was received. In turn, the data analytics server 16 may include data cube class definitions 26. As described in greater detail below, the data cube class definitions 26 may define values, measures, calculated measures, indexes, or other data operations performed on data at the central server 12 to facilitate data analytics in connection with the data analytics tool provided by the data analytics server 16. In this regard, the data cube class definitions 26 may be invoked with respect to data, or a subset of data, provided in the aggregated local dose order data repository 24 located central server 12.

As described above, it is been recognized that the provision of a data analytics tool relative to aggregated data at the central server 12 may provide attendant efficiencies in that a single interface with respect to the central server 12 may be maintained such that interfaces between each given facility 14 and a data analytics server 16 need not be provided or maintained. As such and for example, development of new data cube class definitions 26 may be provided to all users of the data cube without having to specifically develop such cubes for use by each facility 14 individually. However, in connection with performing data analytics on the aggregated local dose order data repository 24, it may be necessary to provide a mechanism that allows for users from respective ones of the facility to access only data at the central server 12 to which the user has corresponding credentials to view. Otherwise, data integrity with respect to each individual one of the facilities 14 may be lost.

Figure 3:
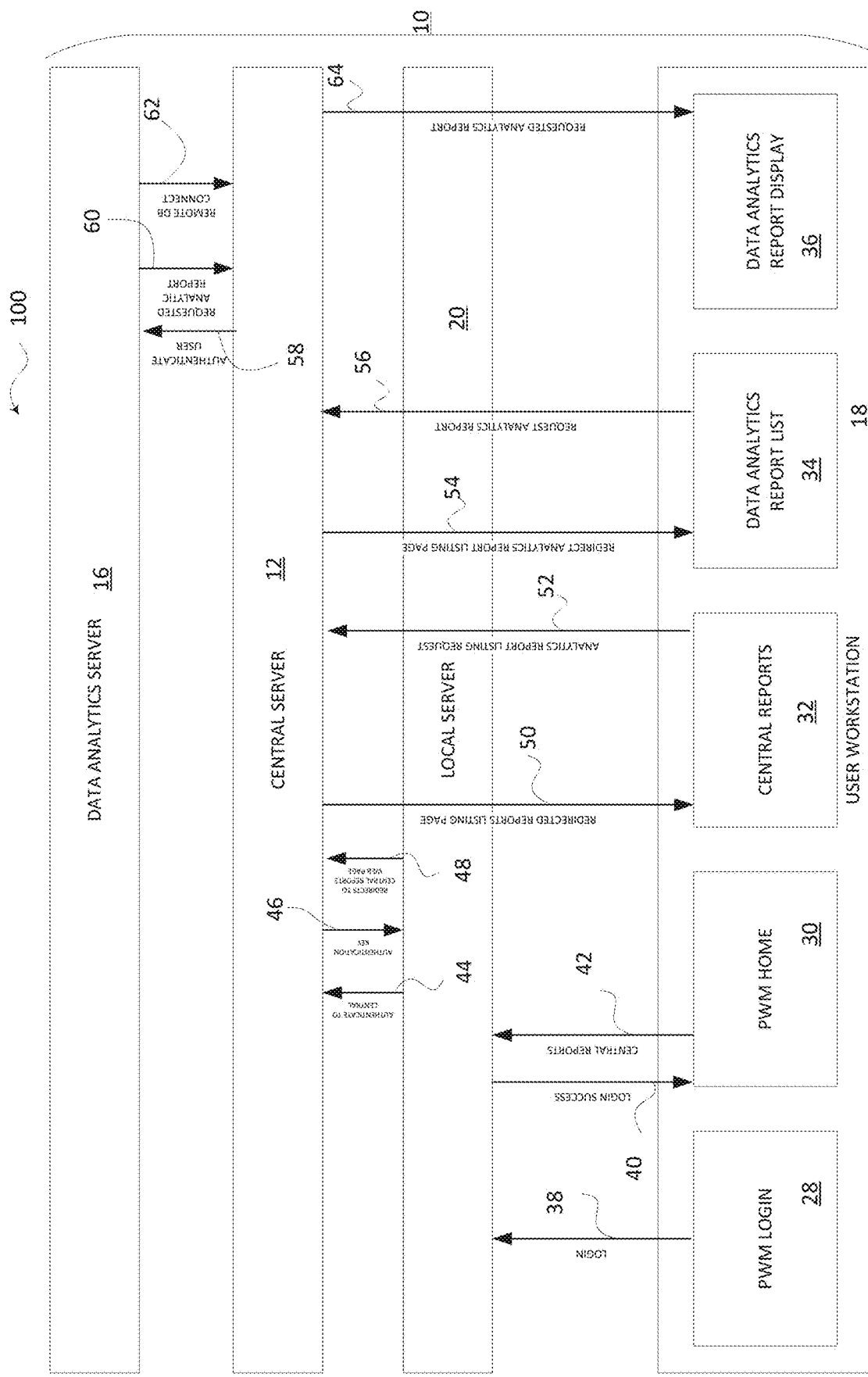
FIG. 3 is a schematic depiction of an embodiment of operation of a system for selective, secure data analytics.

Accordingly, as contemplated herein, a user authentication process may be provided whereby a user may be required to provide user information that may in turn be used to determine a facility from which the user is accessing data analytics tool. Based upon the user identification information, the determination of the data to which the user has access may be appropriately limited to data corresponding to the facility (or organization) corresponding to the user. Accordingly, FIG. 3 depicts a schematic view of a process flow 100 depicted in relation to the system 10 which allows for a user to be authenticated in connection with access to a data analytics tool provided by the data analytics server 16. The authentication of the user may also provide user identification information that may be utilized to determine what data to which the user has access at the central server 12 for use in connection with the data analytics tool. In this regard, the process flow 100 may be utilized to appropriately limit the data to which a user has access to at the central server 12 in connection with the data analytics tool provided by the data analytics server 16. The authentication process may be referred to as a delegated authentication process (as described in greater detail below) as some of the authentication of a user may be performed at a local server 22 and/or central server 12 remote from the data analytics server 16. As such, traditional data analytics tools may require direct access there to for operation on a single data source. However, in the presently described concepts, the data source may, in fact, comprise a plurality of aggregated data sources stored remotely from the data analytics server. As such, the delegated authentication process may allow for access to the remote data in a way such that appropriate data is provided with limited access to appropriate users.

Initially, with respect to FIG. 3, various user interface states associated with user workstation 18 are referenced in relation to the user workstation 18. Accordingly, as may be appreciated by those skilled in the art, the user interface states may correspond to web pages, user interface screens, or other resources accessed by way of a network connection (e.g., including a local area network or wide area network connection). In this regard, the user workstation 18 may be in operative communication with the local server 20, central server 12, and/or data analytics server 16 by way of one or more network connections. In turn, web resources such as web pages or other tools may be accessed at the user workstation 18 to provide the user interface states referenced in FIG. 3. In any regard, the user interface states referenced in FIG. 3 may be rendered at the user workstation 18 in order to allow user to interact with the system 10 is described in greater detail below. As such, the user workstation 18 may, in at least certain embodiments, comprise a thin client that functions to provide functionality provided by a remote access by way the user workstation 18.

Figure 5:
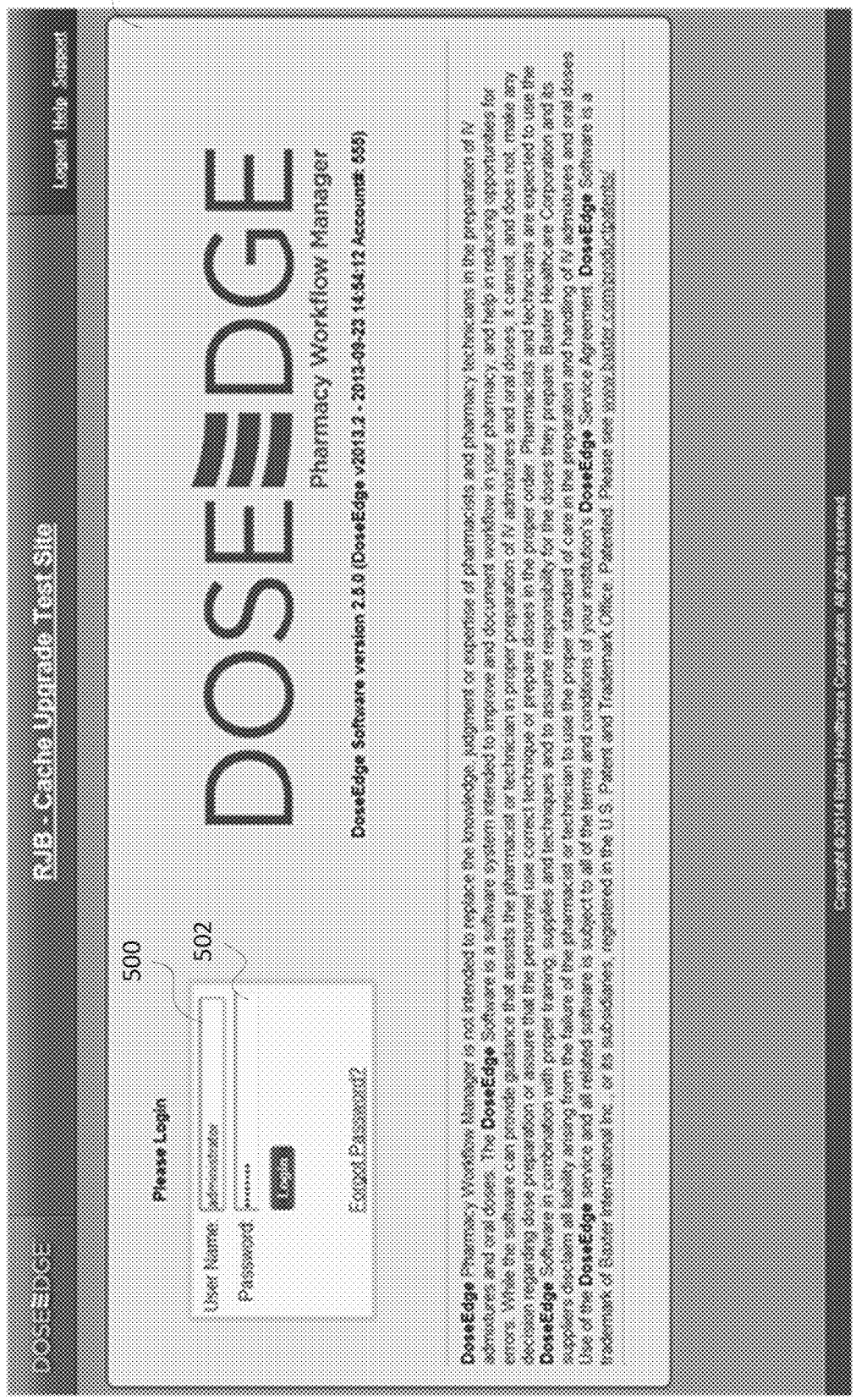
FIG. 5 is a screen shot of an embodiment of a pharmacy workflow management login screen.

The user workstation 18 may initially display a pharmacy workflow management login screen 28. One such example of a pharmacy workflow management login screen 28 is depicted in FIG. 5. In this regard, a user name field 500 and password field 502 may provided on the log in screen 28 presented at the user workstation 18. In turn, a user may enter a username into the user name field 500 and a password into the password field 502. For example, each user at a facility 14 may be assigned a unique username password combination the service identify the user accessing the system 10. As such, the local server 20 may include a record of authorized username password combinations to provide authenticated access to a user attempting to access the system 10.

Accordingly, the user name and password combination entered into the user name field 500 and password field 502 may comprise user authentication information. The provided user authentication information 38 may be communicated to the local server 20. In turn, the local server 20 may process the provided user authentication information (e.g., in reference to the record of authorized username password combinations) to determine whether the user attempting to access the system 10 is authorized to do so. If the user is so authorized (e.g., the user name and password combination provided matches an authorized username password combination stored in the repository the local server 20), the local server 20 may initiate a response 40 that comprises information related to a pharmacy workflow home screen 30. The response 40 may provided to the user workstation 18 such that the pharmacy workflow home screen 30 is displayed to you user workstation 18.

Figure 6:
FIG. 6 is a screen shot of an embodiment of a pharmacy workflow management home screen.

With further reference to FIG. 6, an example of a pharmacy workflow manager home screen 30 is depicted. As may be appreciated, the pharmacy workflow manager home screen 30 may include a plurality of links with respect to functionality provided by the pharmacy workflow manager resident at the local server 20. Of interest in the present discussion, the pharmacy workflow manager home screen 30 may include a link 504 that is utilized access the management reports resource provided by the central server 12. In turn, in the event the user wishes to access management reports, the user may click on the management reports link 504. In turn, a request 42 may be provided to the local server 20 requesting access to the management reports resource provided by the central server 12. In turn, the local server 20 may provide to the central server 12 authentication information 44 corresponding with the user requesting access to the management reports. The authentication information 44 may be analyzed at the central server 12 to authenticate the user (e.g., based on the user name and password information provided during the login 38, other information provided by the local server 20, user credential information management the central server 12, and/or other appropriate information).

Figure 7:
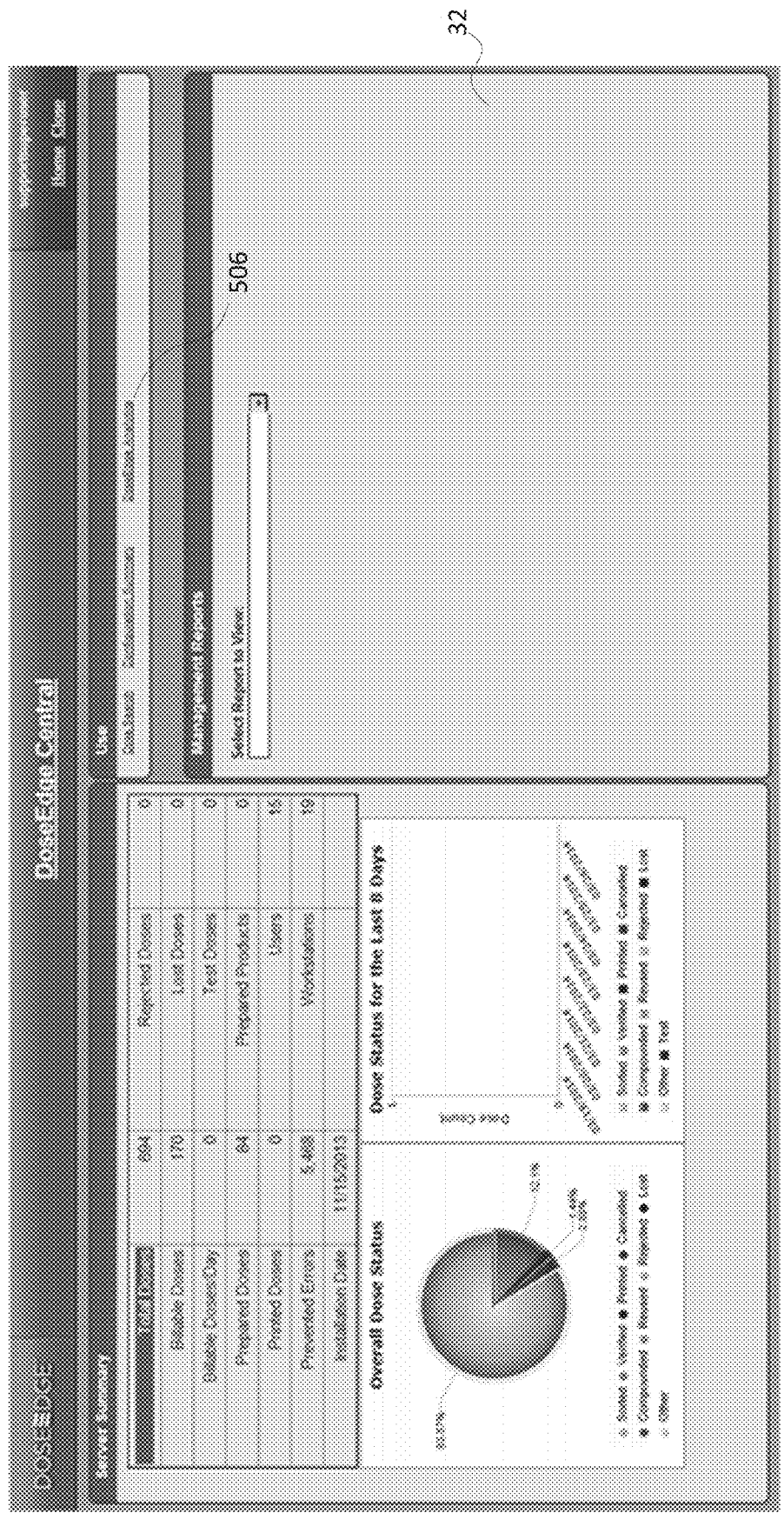
FIG. 7 is a screen shot of an embodiment of a pharmacy central reports screen.

Accordingly, the central server may utilize the authentication information 44 to authenticate the user is having appropriate permissions to access the management reports tool at the central server 12. In turn, the central server 12 may return an authentication key 46 to the local server 20. The local server 20 may in turn provide a redirect command 48 to the central server 12. Upon receipt of the redirect command 48 at the central server 12, the central server 12 may provide a redirection command 50 to the user workstation 18 that redirects the user workstation 18 to a central report screen 32 provided by the central server 12. An example of the central report screen 32 is depicted in FIG. 7. The central report screen 32 may provide static reports regarding the facility from which the user is accessing the central report screen 32. In this regard, the reports provided by the central port screen 32 may not be dynamic and/or provide data analytics tools otherwise provided by the data analytics server 16 as will be described in greater detail below. Thus, as may be appreciated the central reports screen 32 may be provided directly from the central server 12 once the local user is authenticated to the central server 12.

Figure 8:
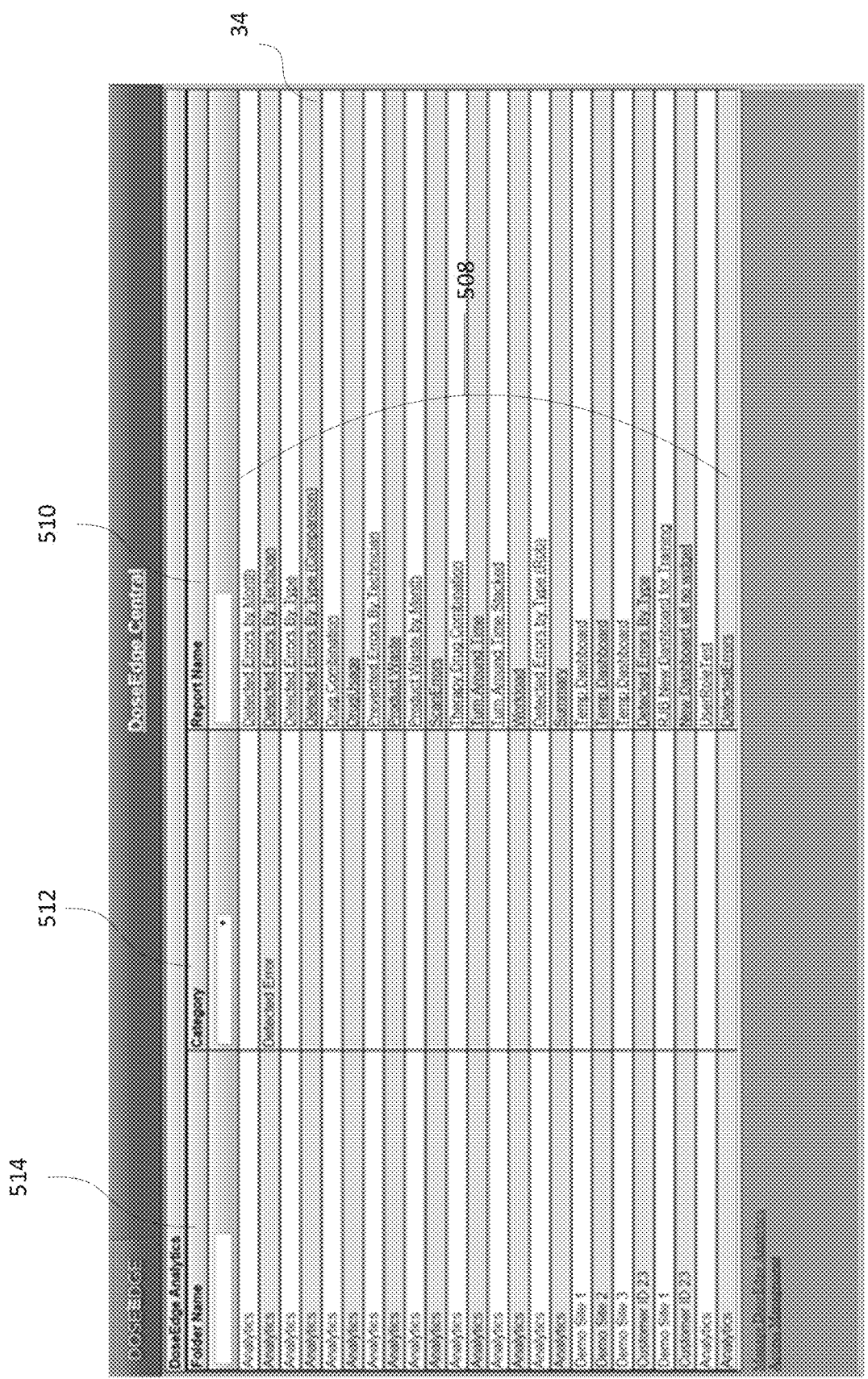
FIG. 8 is a screen shot of an embodiment of a data analytics report list screen.

Additionally, if access the data analytics server 16 is authorized for the given user accessing the central report screen 32, a link 506 to the analytics tool may be provided. The link 506 at the central reports screen 32 may be selected to generate a request 52 for access to an analytics report listing page. In this regard, upon selection of the link 506, the request 52 may be provided to the central server 12 requesting the analytics report listing from the central server 12. In turn, the central server 12 may redirect the user to the data analytics report list screen 34 by providing a redirect command 54 to the user workstation 18. An example of a data analytics report listing screen 34 is provided in FIG. 8. The data analytics report list screen 34 may include a plurality of links 508 to different reports that may be furnished by the data analytics server 16. For instance, different reports 508 may each be furnished by a different data cube class definition as will be discussed in greater detail below.

The data analytics report listing screen 34 may provide the reports 508 in an organized fashion. In this regard, the links 508 to the reports may be provided in a report listing 510. The report listing 510 may include categories 512 that may be arranged in folders 514 for organization of the report links 508. A folder 514 may be generated that may be specific to a given facility and/or given user. In this regard, with the appropriate responsibility or role, a user may be operative to save a copy of a data cube and/or a report generated based on a data cube into the user or facility specific folder. In this regard, a user may be operative to modify the resulting report as desired when saving to the folder. The modifiable report may be saved in a nonpublic folder for access by only that given user or users from a particular facility. Upon selection of a link to report name 508, a request 56 may be provided to the central server 12 requesting the report.

Figure 9:
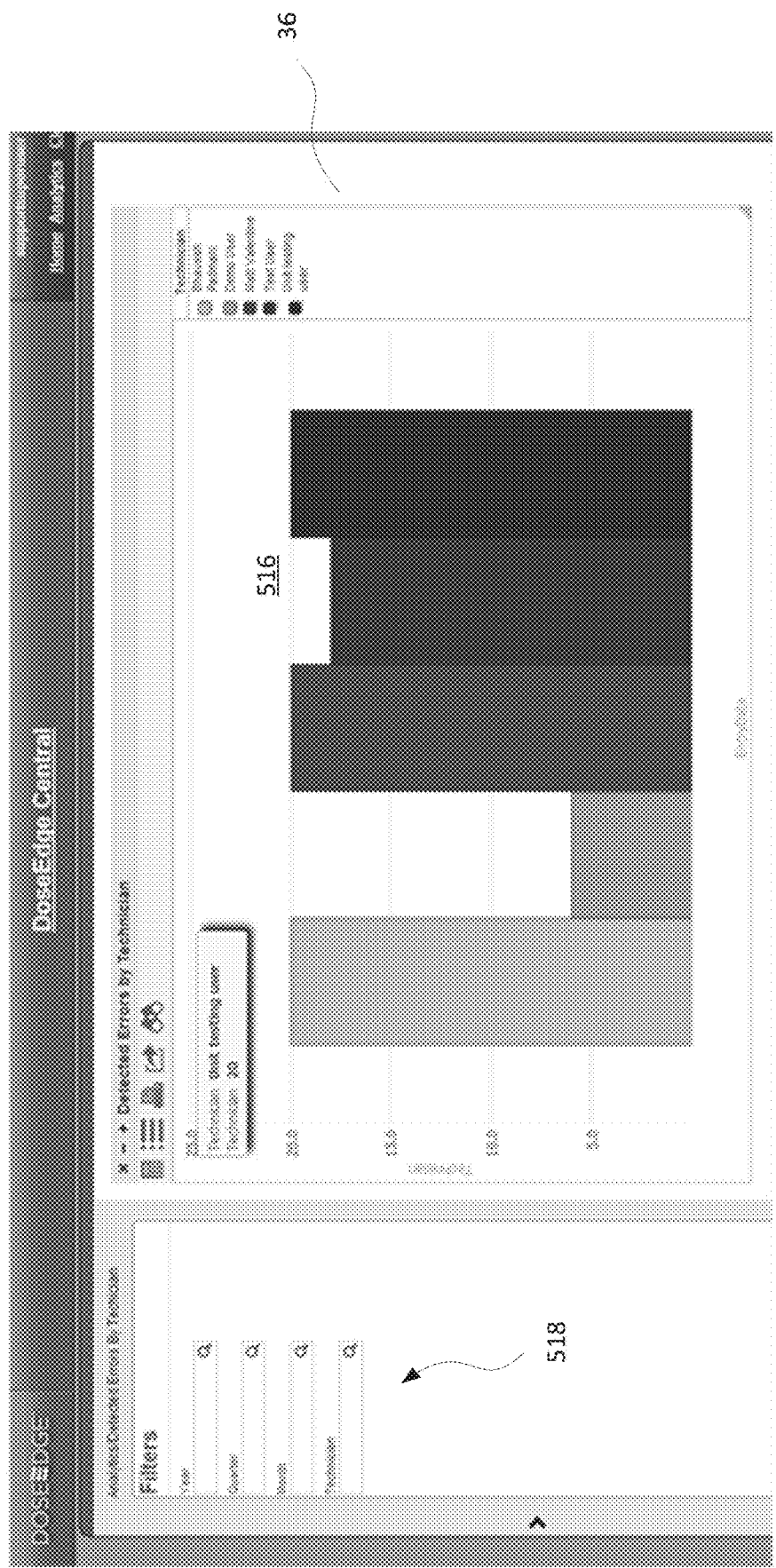
FIG. 9 is a screen shot of an embodiment of a data analytics report display screen.

Upon receipt of the request 56 for a selected report 508, the central server 12 may provide authentication information 58 to the data analytics server 16 to authenticate the user. For instance, the authentication information 58 may comprise or be at least partially based upon user information provided login 38. Upon authentication of the user to the data analytics server 16, a data cube class definition corresponding to the selected report may be invoked and applied to data at the central server 12. In this regard, the requested analytic report may have a corresponding data cube class definition is maintained at the data analytics server 16 that may be provided to furnish the requested analytic report. In this regard, the data cube class definition may be provided 60 to the central server 12 for application to data maintained at the central server 12 to facilitate provision of the requested analytics report by a communication 64 of the report to a data analytics report display screen 36. One such example of the data analytics report display webpage 36 shown in FIG. 9.

The data analytics report display screen 36 may be populated with the requested data analytics report 64 return to the user workstation 18. In the example provided in FIG. 9, a bar graph 516 provided that is generated based on application of the data cube class definition corresponding to the report (e.g., in this case "Detect Errors by Technician"). Furthermore, filtering parameters 518 may be selected to be applied (e.g., as defined by the data cube class definition used to generate report) to further filter the data presented in the graph 516. In this regard, as may be appreciated, the report displayed in the data analytics report display screen 36 may be dynamic in that the user may select various parameters to dynamically alter the presentation of the report real time. Other examples of reports that may be presented in the data analytics report display screen 36 may include charts, graphs, pivot tables (e.g., the axes of which may be selectable by a user in real time utilizing the data analytics tool), dashboards, or other data analytics tools. Furthermore, the ability to view and/or modify these various parameters associated with the report may be at least partially based upon an assigned role or resource privilege granted to a user during the authentication process for the user.

As described briefly above, the reports that may be delivered for display in a data analytics report display screen 36 may be at least partially derived upon application of a data cube class definition to data at the central server 12. A data cube class definition may be used to create a data cube for use in generation of the report. A data cube is a multidimensional data structure used to aggregate data from the associated underlying data table(s) and/or data source(s). While the term "cube" is utilized, a data cube may include more than three dimensions. As such, use of the term "cube" does not restrict a data cube to three data dimensions. Rather, a data cube may have dimensions that may correspond to associated fields in a database table of the source of the data (e.g., including any of the fields described above in relation to the dose order data), which may include many more than three dimensions. Dimensions may also be provided with levels, which may be hierarchical (e.g., to provide drilldown functionality in resulting reports based on a data cube). A data cube also may have measures comprising data elements that are values based on underlying data (e.g., that result from application of a function to the data). For example, measures such as an average, a sum, a minimum, a maximum, or other function may be applied to generate a measure included in a data cube. In this regard, the measures may be provided in the underlying data source or may be calculated based on the data in the underlying data source.

A data cube class definition may be developed to develop specific measures, dimensions, levels, values, indices, or other tools used in the data analytics process. Once all of the measures, dimensions, values, indices, etc., are defined for a data cube in the data cube class definition, and then the cube must be compiled. Compilation creates all of the necessary classes required to define and access the data in the form of the data cube. The final step is to build the data cube. The step of building the data cube populates all of the cube dimensions with data so that it can be viewed and reported on. In this regard, a batch job may, on a periodic basis, execute to synchronize the data from the source tables (e.g., the data stored at the central server 12) to the data cube as defined by the data cube class definition.

Once built, the data cube may be static, yet used by a user to generate dynamic reports (e.g., tables, charts, graphs, pivot tables, dashboards, etc.) based on the underlying data cube. The data analytics tool may have various levels of responsibility that may be used to perform various functions relative to the data analytics tools. For instance, a user may be authorized to utilize an architect tool that allows data cube class definitions to be created. Additionally, a user may be authorized to utilize an analyzer tool that allows for creation of reports, pivot tables, or other analysis tools based on a built data cube. Furthermore, a user may be allowed to utilize a viewing tool that displays results from pre-defined reports, pivot tables, dashboards, or other predefined analytics report outputs (e.g., designed by the analyzer tool). An administrator level of access may be provided that facilitates access to all levels, and other specific roles may be developed with privileges related to a plurality, but potentially less than all, responsibility levels of the data analytics tool.

Figure 4:
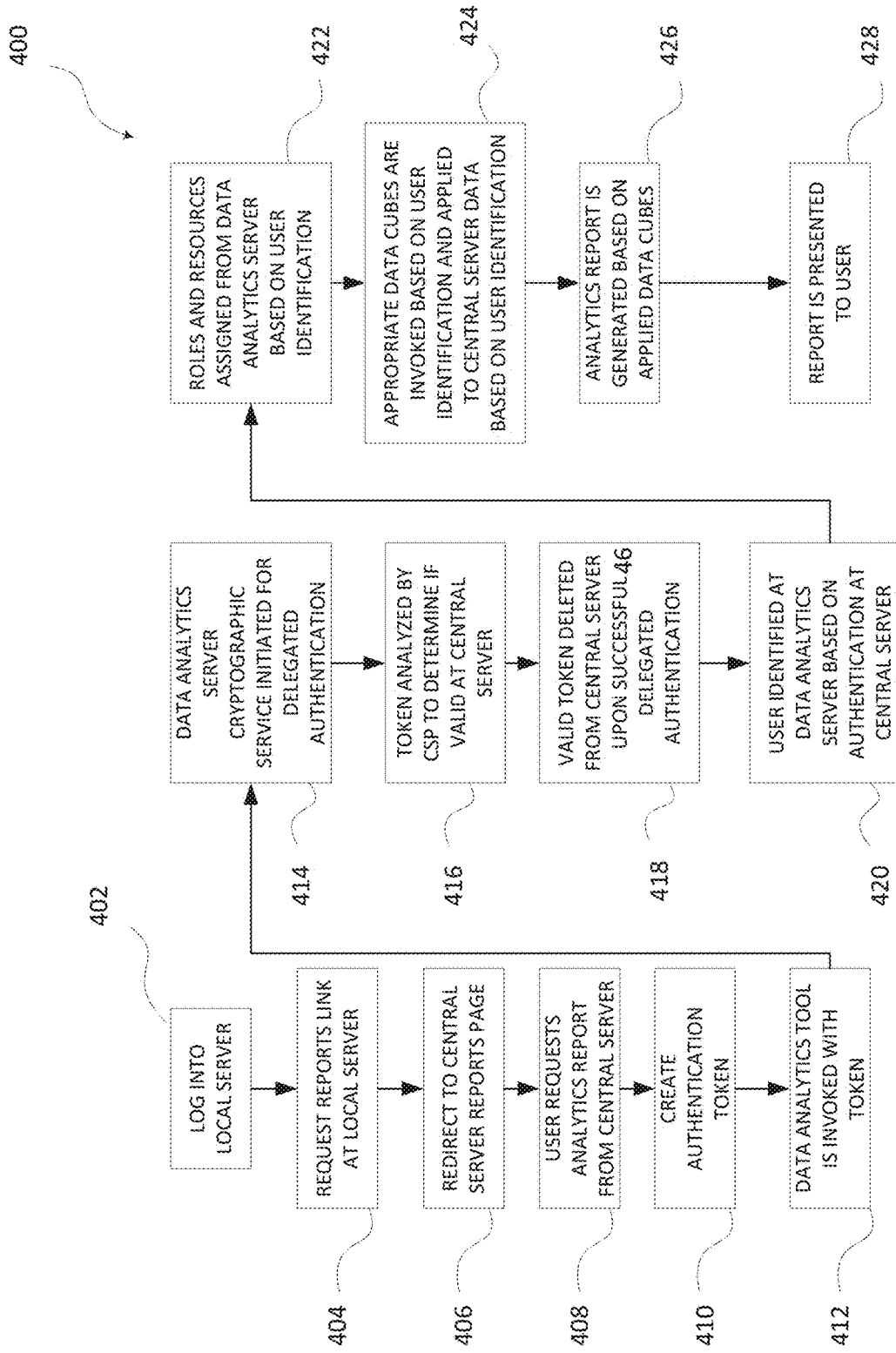
FIG. 4 is a flowchart depicting an embodiment of delegated user authentication for use in a system for data analytics.

With further reference to FIG. 4, a delegated authentication process 400 may be utilized by the system 10. The delegated authentication process 400 is shown in the form of a flowchart in FIG. 4. The delegated authentication process 400 may allow for an authenticated user that has provided sufficient credentials to access the central server 12 to be authenticated in a delegated fashion such that the analytics server 16 provides a data analytics tool relative to data stored in central server 12 upon the delegated authentication by the central server 12. The process 400 may initiate with a user logging onto a local server 402. As described above, the logging onto the local server 402 may include providing a username and password. In turn, the local server may include a database of valid username and password combinations to determine whether a user is authorized to access the local server. Upon successfully logging into the local server 402, the user may be presented with an option to request 404 access to a reports tool at the local server. Upon requesting 404 access to the reports tool at the local server, the user may be redirected 406 to the central server reports page. In this regard, the central server may provide a webpage that is displayed to the user.

The central server reports page may include a link to an analytics report if the user has sufficient credentials to access the analytics report and/or if the central server reports page is configured for the site from which the user is accessing the central server. Upon the user requesting 408 an analytics report from the central server, the central server may create 410 an authentication token that is in turn stored in a database at the central server. The central server may also invoke 412 a data analytics tool. When the data analytics tools invoke 412, the token that is created 410 may be passed to the data analytics server when the data analytics tool is invoked 412.

In this regard, when the data analytics server receives request to access a data analytics tool provided on the data analytics server, the data analytics server may initiate 414 a cryptographic service provider to perform the delegated authentication of the user requesting access to the data analytics tool. Specifically, the cryptographic service may contact the central server with the information regarding the token that is received from a user access request. If the token matches a token provided in the database at the central server, the user may be authenticated. In turn, the valid token is deleted 418 from the central server to prevent unauthorized future use of that particular token. In this regard, upon a user requesting 408 access to the analytics report from the central server, a token is created 410 and stored at the central server. The user may be redirected to invoke 412 the data analytics tool and the corresponding token created may be provided along with the request. In this regard, when the data analytics server receives a request for authentication, the cryptographic service provider may contact the central server to determine whether the token provided in the request matches one created in the database. In this regard, unauthorized requests for access to the data analytics server using a token that does not have a corresponding token stored in the central server may not be authenticated, thus reducing the ability for the tool to be accessed by unauthorized users with fraudulent or expired tokens. In this regard, the token may be analyzed by the cryptographic service provider to determine 416 if the requested user access is authenticated. In turn, the user may be identified 420 at the data analytics server at least in part based on the authentication from the central server. That is, the login information provided to the local server 402 may be in turn pass to the central server.

Additionally, the central server may provide the user information to the data analytics server 420 to identify the user. This information may comprise a session variable that may, for example, identify the user as described below and/or include information regarding a role and/or resources available to the user based on the user's credentials. This may include defining a user and or facility attempted to access the data analytics server. In turn, based on the user identification, roles and resources may be assigned 422 from the data analytics server to the user attempting to access the data analytics server to invoke a data analytics tool. In this regard, appropriate data cubes may be invoked 424 based on the user identification that are in turn applied to the central server data based on the user identification. As described above, the appropriate data cubes may filter data at the central server such that a user from a given facility may only access the data corresponding to that facility when utilizing the data analytics tool. Furthermore, depending upon the roles and resources assigned at 422, different ones of the data cubes may be provided to the user to run various different reports regarding a data. In turn, an analytics report may be generated 426 based on the plight data cubes and report may presented 428 the user.

Specifically, upon identification of the user requesting access the data analytics tool provided on the data analytics server, the authentication may include logging a user into to a data analytics environment as a data analytics user with the appropriate roles assigned. For instance, during delegated authentication, the requesting user may be logged-in with a user name in the format <customerID>|<userID>|<username>, where <customerid> is the customer ID (e.g., corresponding to a facility) from which the user is accessing the central report pages. For example, the user identification may be provided as part of a session variable communicated to the data analytics server. Rather than the customer ID, a 0 may be used to populate this field for support users accessing the data analytics will from the central server directly, <userID> may be the user ID corresponding to the user (e.g., with 0 being used again for support users accessing the data analytics tool directly from the central server), and the username may be the user's login id. As an example, the Administrator user from customer ID 5, with a central server user id of 10 will be logged in as "5|10|Administrator".

In turn, when accessing data for generation of reports using the data analytics tool, the user identification (e.g., such as that described above) may be utilized to limit the data to which a data cube class definition is applied or limit the data to which a user may access when generating a report. For instance, in one implementation, a base cube class definition may be provided from which all other data cube class definitions dependent. In this regard, all data cube class definitions may inherit from the base cube class definition. To prevent unauthorized access from the local server, all developed data analytics tool data cube class definitions inherit from the base cube class definition that comprises a special security filter class definition. In this regard, the base queue class definition may include an organization identifier and a customer identifier as default dimensions, in addition to any other dimensions to be included in the cube definition. The base cube class definition may use these two properties to include only records from the specific customer or organization account based upon the received user identification information during the user authentication process. This acts as a security mechanism to prevent users from accessing other customer data on the central server.

For instance, to filter central server data based on a user's access to organization or site data, the base cube detects whether the user is an organization level user or a site level user. Based on the evaluation, a multidimensional expression filter string is assembled based on either the organization or sites that the user belongs to. Once the filter string is assembled, the multidimensional expression filter is applied to all data in the base cube (e.g., which must include dimensions corresponding to the organization ID or client ID) and limits the information that the user sees in any report. As such, the base cube class definition may, in conjunction with the user identification information received during the authentication process, serve to limit access for a user to data only corresponding to the facility (or organization) to which the user belongs or from which the user is accessing the tool. As such, while the data analytics tool operates on aggregated data corresponding to a plurality of facilities, the base cube class definition from which all other data cube class definitions depend, may serve to limit access to data correspond to the user's facility. Because internal users (e.g., users accessing the data analytics tool from the central server directly) must also be able to access the data from the data analytics tool, the base cube class definition also detects whether or not the user has accessed the environment from the local server or directly using the central server. It may accomplish this by determining if the session variables for a given user session in which a user requests access to the data analytics tool is populated with the expected parameters. If so, then access is assumed to by via the local server. If not, then access is assumed to by via the central server screens and a check is made of the roles attributed to the user session definition to see if the correct roles are assigned to the user accessing the data analytics tool from the central server.

Additionally, a protected heath information (PHI) parameter may be used to indicate if PHI information is exposed by the cube. This will allow reports to be generated to identify cubes with PHI information. Cubes containing PHI information may also require a specific resource attributable to specific users to access the cube. This will limit access to pivot tables and dashboards derived from those cubes containing PHI. In this regard, a particular concern regarding exchange of medical information includes maintaining the privacy of patients as it relates to the exchange of medical information. For instance, medical information may include patient identifying information (e.g., potentially including PHI). In this regard, dissemination of medical information may subject to restrictions due to regulatory issues (e.g., the Health Insurance Portability and Accountability Act (HIPAA) in the United States) may prohibit dissemination of medical information with PHI or other privacy concerns. While HIPAA may define PHI, it may be appreciated that as used herein PHI may include data included in the HIPAA definition as well as other data. For instance, any patient identifying information (e.g., patient name, patient identification number, etc.) may be defined as PHI.

Furthermore, data cube class definitions may include data transformations that are applied to data from the data source. These transformations may include generating calculated measures based on underlying source data. The transformations may also include modification to the source data. For example, in one specific example related to total parenteral nutrition (TPN) doses, certain dose order record fields may be acted upon by a corresponding data cube class definition. In this regard, a data cube class definition, during the build process, may replace a given dose order field (e.g., a DoseDescription field) with the value from another field (e.g., the DoseDrugNames field). This transformation may be applied only to a certain type of doses (e.g., for TPN doses as determined by a record flag indicating whether the dose order is a TPN order or based on a drug contained in the order). As such, during cube building, a record from the source data table will be determined if the record contains the appropriate fields (e.g., "DoseDescription", "TPN", and "DoseDrugNames" following the example above). Once a record is determined to be a TPN order to which the data transformation applies, the data analytics server will check the TPN field and if it is set to 1 (the dose is TPN) then the value of field "DoseDrugNames" may be copied into the field "DoseDescription".

Additionally, each data cube class definition is such that when building the data, the cube will not load any records from sites designated with the "Data Exclusion" flag. In this regard, the base cube class definition may determine if a record is for a customer site with the data exclusion designation and if so, it will skip the record from being loaded. The data exclusion designation 522 is set in the server detail page 520 shown in FIG. 10.

Figure 10:
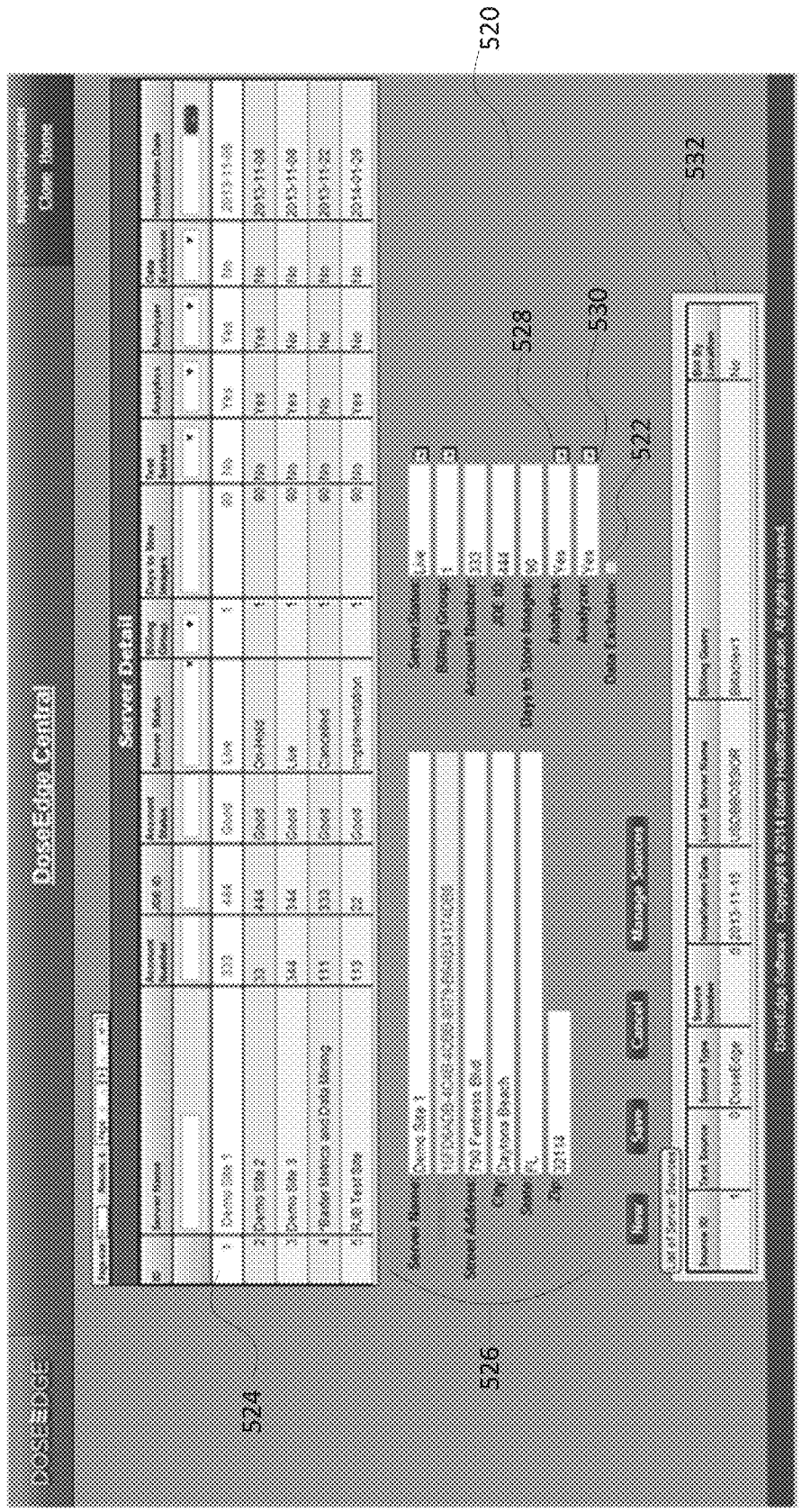
FIG. 10 depicts an embodiment of a data analytics tool configuration setup.

In this regard and with further reference to FIG. 10, a server detail page 520 is shown that allows for configuration of behavior of the data analytics tool when accessed by various servers. In this regard, a listing 524 of local servers is provided that may provide users access to the data analytics tool. For each server in the listing 524, a server configuration field 526 is provided. In this field 526, details regarding the server (e.g., location address, server status, billing information, account number, server configuration details, etc.) may be configured. Specifically, an analytics access selection field 528 may allow an administrator to set permissions related users from a given local server having access to the data analytics tool (e.g., thus determining whether a link 506 to the data analytics tool is provided on the central reports screen 32 of FIG. 7. Furthermore, an analytics analyzer selection field 530 may be provided that is used to set permissions related users from a given local server having access to an analyzer of the data analytics tool (e.g., where reports, dashboards, pivot tables, or the like may be generated). Additionally, a data source listing 532 may be provided in relation to each particular data source of a given server in the listing 524.

With returned reference to data cube class definitions, certain useful data transformation techniques may be provided for use with a data cube class definition. For instance, a protected health information (PHI) parameter may be provided (e.g., with all cubes) to identify if the cube exposes PHI information. If a parameter indicative of PHI being present is determined to be true, then the cube contains PHI fields, otherwise the cube is not considered to contain PHI fields. The PHI parameter may be dynamically generated based on the underlying data source to which the cube class definition is applied (e.g., whether any source data is determined to have PHI).

Additionally, a delta time function may be provided. The delta time function may be used to calculate the time difference between two times. Each time value may be passed as a parameter to the function and the time difference (e.g., as measured in minutes, hours, days, seconds, etc.) is returned as the value of the dimension. As such, when a cube measure is created that will use the time function, a measure name may also created that is representative of the time measure being extracted. For instance, a measure called "DeliveredTimeMinutes" could be defined as the difference between the time the dose was delivered to the patient and the time it was received in the pharmacy. Continuing the example, the data cube class definition having the cube measure "DeliveredTimeMinutes" may have instructions such that a specific method call performs the actual calculation and the source data elements are the time values to be compared. For instance, the specific method call may return the difference of the defined time measures to be compared and return the value as a positive integer.

Furthermore, one or more custom time functions may be created. Custom functions can be created to evaluate any number of desired results. For a custom time reporting function that relies on multiple inputs to evaluate an elapsed time, a custom time function that may take four time inputs and evaluates the dose preparation time based on coded criteria using the four input values may be provided. This method may take the four defined time value and perform specific calculations thereto (e.g., evaluating the time doses were at various stages of processing defined by the four inputs).

Additionally, record filtering may be provided by a data cube class definition. This may allow for record filtering to eliminate records from the cube dataset that are not needed. This may be thought of as similar to adding a WHERE clause to and SQL statement. In this regard, by setting up an "if" statement to determine if a record should be included or not records can be excluded from the fact table when building the cube. For instance, in an example a data cube class definition may filter records based on the contents of one or more given dimensions in the cube (e.g., Type and ErrorCategory).

Additionally, the cube definition may include the listing tag which defines the fields to display to the users when they drill-down within a pivot table or dashboard. A pivot table may have multiple listings defined. When defining a pivot table based on a cube, the pivot table designer may select which listing to display when the end-user drills down on the pivot table. The dashboards based on that pivot table may also inherit the ability to drill down in the data to display the listing specified during the pivot table design.

Furthermore, a data cube class definition may include an operation that is utilized to de-identify patient information contained within the data for a given data cube. For example, a hash function or the like may be applied to the patient information, thereby rendering the resulting data in the data cube non-identifying of the patient. In further embodiments, the source data for a data cube class definition may be a data source in which the patient identifying information has been removed (e.g. by a hash function or the like).

Additionally, upon a user accessing the data analytics tool, a log event may be created that provide logging information with respect to the user accessing the data analytics tool and various specific resources accessed during a session. In this regard, log entries for a given user session and/or navigation occurring within the user session may be generated (e.g., by a logging module at the central server 12 and/or data analytics server 16). These log sessions may provide access regarding a particular session to achieve user is defined and may provide details regarding specific navigation of the user during the session. In turn, the user logs may be reviewed to determine which users access is accessed which resources and particular parameters in connection with that access. In connection therewith, a schema 600 corresponding to an embodiment of a user log is depicted in FIG. 11.

Figure 11:
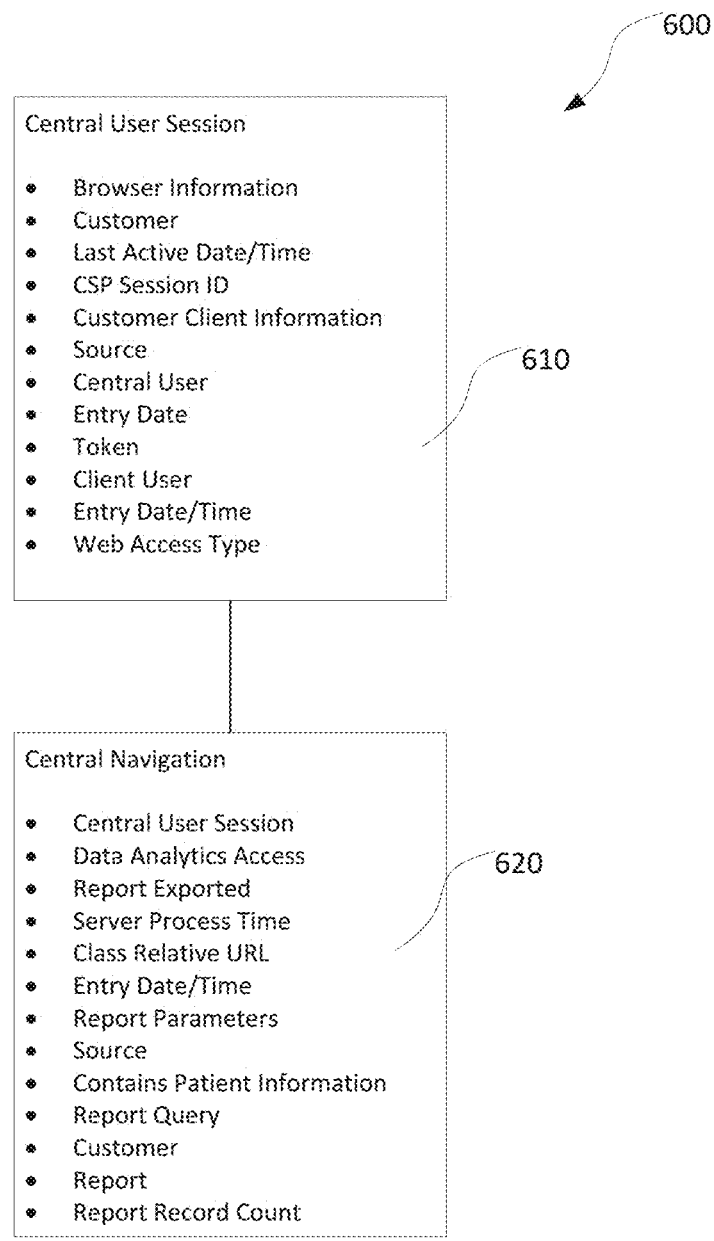
FIG. 11 depicts an embodiment of a logging schema that may be used in connection with a data analytics tool.

Accordingly, with further reference to FIG. 11, the schema 600 used to generate log records may include a central user session log 610 created for each session by a user. Sub-records in the form of central navigation log 620 may be created for each central user session log 610 that tracks specific navigation of the user during the session corresponding to the central user session log 610. In this regard, a session log record may be generated according to the schema for the central user session log 610. Accordingly, the session log 610 may include the property "Browser Information" as a string that stores the browser used by the user. The session log 610 may also include a property "CSP Session ID" that corresponds to a reference to the cryptographic service provider session identifier used to serve the user session being logged (e.g., potentially corresponding to the token received from the user). The log 610 may also include the property "Central User" that links to the user related to this session. This may indicate a central user accessing the tool directly from the central server as a support user from central server if applicable. The log 610 may also include a property "Client User" that comprises a link to the user related to this session from the client application. The log 610 may also include a property "Customer" that includes the identity of the customer from which the user is accessing the tool. The log 610 may also include the property "Customer Client Information" that may include the site statistics to get specific details about the client from which the user is accessing the tool. The log 610 may also include the property Entry Date that indicates the date the session was entered. The log 610 may also include the property "Entry Date Time" that comprises the date/time the session was entered. The log 610 may also include the property "Last Active Date Time" that corresponds to the date/time the session was last active or updated. The log 610 may include the property "Source" that provides information regarding the customer source if the user was redirected from a local server. The log 610 may also include the property "Token" as that corresponds to the uniquely identifiable token described above. Furthermore, the log 610 may include the property "Web Access Type" that comprises an identity of the specific application of the data analytics tool that was accessed.

Additionally, for each session log, sub-records comprising a central navigation log 620 corresponding to session activity or navigation may be created. The central navigation log 620 may include properties such as, for example, the property "Central User Session" that links to the central user session log 610 associated with the navigation being logged. The log 620 may also include the property "Class Relative URL" corresponding to the class accessed. The property "Contains Patient Information" may be a true/false indication as to whether the resource (e.g., page, report, tool) being accessed contains PHI information. In this regard, either the a parameter "HASPHI" may be set to 1, or the report definition field "ContainsPHI" may be set to 1 if a report is being executed that includes PHI. The log 620 may also include the property "Customer" that indicates 1 the customer from which the user is accessing the tool. The property "Data Analytics Access" may indicate the resources from the data analytics tool utilized (e.g., including the data cube definitions invoked or the like). The property "Entry Date" may correspond to the date the session was entered, and the property "Entry Date Time" may correspond to the date/time the session was entered. The log 620 may also include the property "Report" that indicates the identity of a report accessed, if any. The property "Report Exported" may include an indicator as to whether the report was exported. The property "Report Parameters" may include the parameters selected by the user when running a report or otherwise utilizing the data analytics tool. The property "Report Query" may include an identity of the query executed to generate a report, and "Report Record Count" may include the record returned by the report. The property "Server Process Time" may correspond to the processing time in ms (milliseconds). The property "Source" may include an indication of the customer source if the user was redirected from a local server.

In relation to the foregoing description, it may be appreciated that the data analytics tool described herein may be utilized in a number of different contexts in relation to dose order data. Thus, while dose order data is referenced throughout the present disclosure, such data may include and/or provide for far reaching data analytics. For instance, as described above the dose order data upon which the data analytics tool may be invoked may include a plurality of different dose order data classes that may include information related to the dose order, the preparation of the dose order, products used during the preparation of the dose order, or any other related information. In this regard, it may be appreciated that a plurality of different categories of data cube class definitions may be provided in a data analytics tool. Importantly, all such data cube class definitions may depend from the base cube class definition that permits selective, secure access to the facility (or organization) specific data corresponding to a given user.

For instance, a number of categories of data cube class definitions may be provided. For example, the data cube class definitions may relate to, as way of example, general pharmacy workflow activity, pharmacy performance metrics, pharmacy exceptions, pharmacy usage and waste, data related to products and therapies, compliance data, and user logs. In this regard, examples of data cube class definitions in the general pharmacy workflow activity category may include a data cube class definition corresponding to basic statistics regarding dose orders, dose order items, dose preparation information, dose claim activities, dose scan events, dose verification history, and procedure summaries. In this regard, the data cube class definition corresponding to basic dose statistics may include dose dimensions related to, for example, dose administration time, whether the dose was a first dose in a series of doses, the dose route (e.g., intravenous, oral, intramuscular, etc.), whether the dose a hazmat dose, whether the dose is a high-risk doses, the nursing unit corresponding to the dose, whether the dose is a STAT dose, whether the dose is a total parenteral nutrition (TPN) dose, the type of TPN dose, whether the dose includes an unknown drug, the technician that prepared the dose, the workstation that was used to prepare the dose, whether the dose is a stock dose, whether the dose is a dilution dose, the dose status, the dose preparation date, the dose entry hour, and the dose entry minute. Furthermore, any of the foregoing dimensions may include normalized versions of the dimensions (e.g. for instance in the case of normalized drug names, normalized amounts, normalized units, or the like). Furthermore, some data cube class definitions that provide dose order summary data may include measures related to the total volume of the dose, the final volume of the dose, a QS volume of the dose, a QS diluent name, a stock dose count, a dilution dose count, a number of rework doses, in-line verification of a dose, the number of images per prepared dose, the number of fully compounded doses by a compounder, the number of dose manual additions, the number of doses with material requests, the number of doses having expanded drug names, the number of doses by status, the number doses by route, the number of attachments for a dose order record, and a normalized dose description. For data cube class definitions regarding dose order items, the data cube class definitions may relate to dimensions corresponding to the dose status (e.g., to filter our records that have not actually been delivered to a patient), a dose description, a dose description normalized based on formulary drug names, base units, and diluents, whether the dose is a stock dose, whether the dose is a dilution dose, whether the dose is a hazmat dose, whether the dose is a high risk dose, the total volume of the dose (e.g., including contributions small products), the final volume of the dose (e.g., as specified for the dose order by an electronic medical record (EMR) system or hospital information system (HIS)), the QS volume, and a QS diluent name. Data cube class definitions related to the dose preparation information may include data dimensions corresponding to the preparation mode used to prepare a dose, preparation mode options the time the dose was prepared, and a calculated QS volume for a dose. Data cube class definitions may relate to the occurrence of a pharmacist claiming a dose during verification (e.g., from another use who has a session verifying the dose). In this regard, dose claim data cube class definitions may include data dimensions corresponding to whether a dose was claimed during verification, whether the individual claiming the dose disposed of the dose that was claimed, the reason a claim was successful or unsuccessful, whether the claim was overwriting another user's claim, the time a claim is active, the overwriting user, the overridden user, and a dose identifier. Data cube class definitions related to dose scan events may include data dimensions related to the scan event name, the dose order identifier, the product lot identifier, a catalog identifier, a user identifier for the scan, and the event target (e.g., calculated to determine the dose order, product blog, or kit event type). Data cube class definitions related to dose verification history may include data dimensions corresponding to the user identifier of the user who verifies the dose, the date/time the dose is verified, the results of the verification, the reason provided during verification (e.g., for requeue, cancellation, and rework orders), the dose identifier, the verification type, the disposition of the dose, a reason for remake, and a rejected product log. Data cube class definitions related to procedure records may include the entry date and time of the dose, the completed date and time of the dose, the user identifier of the technician used to prepare the dose, the workstation identifier of the workstation used to prepare the dose, the name of the dose, a central formulary procedure ID (e.g., corresponding to a procedure presented the user in the preparation), a procedure type, a completed action count, a required action count, a total action count, and a completion time.

Additionally, a number of performance data cube class definitions may be provided that may include information regarding dose turnaround time and system performance. For data cube class definitions regarding dose turnaround time, the data cube may include dimensions related to a workstation used to prepare the dose, a preparation location name, a technician name, a patient location, a nursing unit corresponding to the dose, a priority of the dose, whether the dose is a STAT dose, whether the dose is a hazmat dose, a number of items in the dose, whether the dose is a stock order, dose drug names, and a preparation date/time. Furthermore, a number of measures may provided for a data cube class definition related to the dose turnaround time including an average time preparation, a delivered time, a waiting for preparation time, a time to resume preparation after an in-line verification or rework, a time until dose distribution, a average time to verify the dose, and an average time to sort the dose. The data cube class definition regarding system performance may include data dimensions corresponding to the time/date of a log, the calculated record length of the session, a function name, an average data analytics server execution time, and average client server execution time, a maximum data analytics server execution time, a maximum client server execution time, a minimum data analytics server execution time, a minimum client server execution time, and an execution count.

Furthermore, a number of data cube class definitions related to dose exceptions may be provided. Examples may include data cube class definitions related to prevented error (e.g., scan errors), detected errors, bypass reasons, dose order modifications, and alerts. Accordingly, prevented errors may correspond to errors identified by the pharmacy workflow management application automatically without human intervention (e.g., scan errors or the like) and the detected errors may include errors identified by a human interacting with the pharmacy workflow management application such as a pharmacist during a dose review. A data cube class definition related to scan errors may include data dimensions related to doses containing a prevented error generated during dose preparation, a dose category, a dose identifier, a scanned barcode, a scan formulary product information, scan product log information, technician information, and workstation information. The data cube class definition related detected errors may include detected error data generated at the pharmacist check station. Data dimensions contained within the detected errors data cube class definition may include a reason for remaking a dose, pharmacist information, technician information, workstation information, preparation location, a nursing unit associated with the dose, a dose route for the dose, whether the dose is a hazmat dose, a type of hazmat dose, whether the dose is a TPN order, a the dose description. A data cube class definition related to bypass reasons may include information related to doses in connection with a bypass print operation whereby the dose order, upon being received by the pharmacy workflow management application, is bypassed for printing of the dose order by a label printer in a traditional fashion. As such, data dimension for the bypass reasons data cube class definition may include an indication that the dose was bypassed, a time and date of the order entry, drug information corresponding to the dose order, information regarding the source of the data order, etc. A data queue class definition regarding dose order modifications may include data dimensions including what modification was made to the dose including an administration date/time update, a discontinuation of a dose, a change in priority for dose, a movement of the dose onto or off of a hold status, an expiration date/time of a dose due to using a stock product with an earlier expiration date, whether an adjustment was done automatically by the system or intentionally by user, who made a modification, and why a modification was necessary (e.g., if the site is configured to enter reason for modification). A data cube class definition related to dose alerts may include data dimensions corresponding to whether a dose is subject to an alert during the preparation process and other dose identifying information that may allow trends with relation to a dose alert to be determined Other data cube class definitions may include data dimensions regarding received alerts (e.g., from within a pharmacy workflow management system or from an external alert provider) regarding dose orders, patients, drugs, or some other portion of data stored by a pharmacy workflow management application.

Data cube class definitions may also relate to usage and waste metrics in the pharmacy. Examples may include data cube class definitions related to product waste, drug waste, and products siblings. Accordingly, a product waste data cube class definition may include data dimensions corresponding to data from unused/expired products such as product preparation location, preparing technician information, dose status, dose name, an NDC code for drugs in the dose, a total volume of the dose, a current volume of the dose, an expiration date of the dose, a number of prepared doses, an unused volume ratio (i.e., the current volume divided by the total volume), a cost for the dose (e.g., referenced from a formulary record for a drug or product associated with the dose), and whether the dose was a multi-use dose. For instance, a resulting report based on the product waste data cube generated from the product waste class definition may include an aggregate of an amount of drug wasted over a given time period and/or the cost associated with that corresponding waste (e.g., using underlying data and/or measures defined in the data cube class definition). A drug waste data cube class definition may include data dimensions corresponding to a product log identifier, an entry date, an expiration date, an activation date, a number of beyond use hours for the dose, a drug name, an amount of the dose, units of the dose, whether the dose is a hazmat dose, whether the dose is a high risk dose, and whether the dose of the diluent dose. In this regard, the beyond use hours data dimension may be a calculated measure that includes the difference between the expiration date and activation date and hours.

The product and therapy category of the data cube class definitions may include data cube class definitions related to therapy summaries and drug combinations. Accordingly, a data queue class definition related to therapy summaries may include data dimensions corresponding to the ability to see a drug therapy instance in terms of average duration (e.g., a number of days, number of doses, or total dose amounts) including, for example, a customer identifier, a source identifier, an entry date for the dose, drug names for the dose, a dose description, and a therapy ID. The drug combination data cube class definition may include a "crosstab" showing the frequency of a combination of drugs when given together. Data dimensions for this data cube class definition may include a customer identifier, a source identifier, an entry date for the dose, a drug name associated with the dose, an amount of the dose, a unit of the dose, and a dose identifier.

A number of data cube class definitions may be related to compliance tracking. Examples may include data cube class definitions related to schedule task histories and weight measurements. The schedule task histories data cube class definition may include data dimensions that may allow for compliance tracking with scheduled tasks to be completed in relation to workstations. In this regard, the data dimensions for the data cube may include workstation tasks, a missed task dose count (e.g., including the number of bad doses because a clean task is not completed on time), information on completed tasks (e.g., including the user, time, workstation, whether the task was overdue, and an overdue time), how many doses were prepared on an overdue workstation by user, a frequency type, a frequency value, a previous completion date/time, a previous due date time, and next due date time. A weight measurement data cube class definition may include data corresponding to weight measurements recorded dose preparation workstation. Furthermore, data queue class definitions related to compliance tracking may allow for filtering and/or searching of doses based on a number of different data dimensions such as, for example, dose type, dose preparation date, technician, location, or any other appropriate dimension. Furthermore, the dynamic report generated based on the compliance tracking may allow for a user to drill down through various dimension levels. At a given level, user may select to view individual dose order records comprising a given set of data (e.g., a chart cell or graph portion may correspond to a certain number of doses, which may be revealed as a listing of the specific dose order records referenced by the chart cell a graph portion upon selection by the user). That is, the report may allow a user to define or select various parameters that allow a user to access a list of doses that meet a criteria established by the user using the selection of various parameters. The compliance tracking data cube may include a link that allows a user to retrieve a dose order log corresponding to a given dose order contained in the listing of specific dose order records. The dose order log may include any or all information related to the selected dose order (e.g., including data regarding the dose order record outside of the data dimensions of the data cube used to filter or search for the dose order itself). That is, the dose order log may include any or all information regarding the dose order log even if that dose order information does not comprise a dimension contained in the data cube used to obtain the link to access the dose order log for the dose order record. In an application, the dose order log linked to in the compliance tracking data cube may correspond to a dose order log with a specific format and/or data content dictated by an authority such as a government regulatory body or the like for use in determining regulatory compliance.

Additionally, a number of data cube class definitions may be related to user logs. Examples may include data related web sessions, data related to workstation sessions, data related to central user sessions, and data related to central user navigation, and audit logs. A data queue class definition for web sessions information may include data dimensions corresponding to information relevant to web-based user sessions including, for example, an IP address of the user, a login date/time, a logout date/time, a browser name, a browser version, a browser extension installation version, a length of the session, a indication of the breakdown between site configuration time and dose preparation functionality time, an average response time from the server for web service calls, and an average response time for webpage requests. The data cube class definition related to workstation sessions may include data dimensions related to a login date/time for workstation, a logout date/time for the workstation, a workstation software version, the workstation name, a work station location, a username accessing the workstation, and a last activity date/time. A data cube class definition related to central user sessions may include data dimensions corresponding to a central session log, a total session time, and a browser type/version. A queue class definitions related to central user navigation may be based on a central navigation log. An audit log data class definition may be operative to compare a full snapshot of audit logs and identify which fields have changed.

Other data cube class definitions may be provided without limitation that may leverage various ones of the data dimensions present in dose order information. Furthermore, the source data to which data cube class definitions may extend beyond dose order data. For instance, additional data sources (e.g., located at hospital information systems, pharmacy information systems, laboratories, surgical data repositories, formulary records, national healthcare databases, etc.) may be accessible by the data analytics tool. In this regard, data cube class definitions that reference such data sources may be provided. Additionally, data cube class definitions may be provided for use in building data cubes that reference multiple data sources (e.g., including dose order data as well as other data sources such as those listed above including hospital information systems, pharmacy information systems, laboratories, surgical data repositories, and national healthcare databases). In any regard, the foregoing data cube class definitions may be utilized in building corresponding data cubes. In this regard, one or more reports may be generated that reference a data cube for presentation of data to a user. The reports may take the form of pivot tables, dashboards, charts, graphs, or other report mechanisms. The reports may be filterable based on various different data dimensions such as, for example, dose order types, dates, dose statuses, technician, pharmacist, or any other data dimension included in the data cube and defined relative to the report (e.g., which may be modifiable by a user with appropriate role or responsibility). Furthermore, the reports may include drill downs based on the dimension levels as discussed above to provide increasingly detailed data based on a subset of data for a given dimension. In this regard, a user may be able to utilize the reports to identify trends, anomalies, patterns, or other information from the data presented in the dynamic report generated based on a data cube.

While the invention has been illustrated and described in detail in the drawings and foregoing description, such illustration and description is to be considered as exemplary and not restrictive in character. For example, certain embodiments described hereinabove may be combinable with other described embodiments and/or arranged in other ways (e.g., process elements may be performed in other sequences). Accordingly, it should be understood that only the preferred embodiment and variants thereof have been shown and described and that all changes and modifications that come within the spirit of the invention are desired to be protected.

What is claimed is:

1. A system for implementation of a data analytics tool for processing a multidimensional data set corresponding to dose order records for data analytics regarding a subset of the dose order records of the multidimensional data set, comprising:

a central server that is in operative communication with a plurality of local servers, each of the local servers being disposed at a corresponding respective facility that prepares doses corresponding to dose orders for administration to a patient, wherein the central server receives information regarding dose order records corresponding to the dose orders from the local servers;

a database at the central server that stores a data structure comprising a multidimensional data set including a plurality of dose order records received from the plurality of local servers, wherein each of the plurality of dose order records of the multidimensional data set comprises at least one indication of the facility from which the dose order record was received;

a local server interface in operative communication with the plurality of local servers for receiving from at least one of the plurality of local servers user information from a user at one of the plurality of facilities, wherein the user information includes at least one identifier including a user ID, a username, and a customer ID, wherein the customer ID corresponds to a given facility from which the user is accessing the data analytics tool;

a data analytics interface that facilitates operative communication with the data analytics tool, wherein the data analytics interface provides the data analytics tool access to the multidimensional data set stored in the database to generate a dynamically generated report regarding a subset of the multidimensional data set corresponding to the given facility from which the user is accessing the data analytics tool based on the user information received from the local server interface, wherein the user information corresponding to the given facility from which the user is accessing the data analytics tool restricts access to data other than the subset of the multidimensional data set; and a user interface for presenting to the user at a user interface the dynamically generated report regarding the subset of the multidimensional data set corresponding to the given facility from which the user is accessing the data analytics tool.

2. The system of claim 1, wherein the data analytics tool comprises a plurality of data cube class definitions applicable to the multidimensional data set to generate the dynamically generated report, and wherein the at least one identifier is used at least in part to limit the data to which a respective user has access.

3. The system of claim 2, wherein the plurality of data cube class definitions comprise a base cube class definition from which all others of the plurality of data cube class definitions depend.

4. The system of claim 3, wherein the base cube class definition includes at least one data dimension related to the at least one indication of a facility corresponding to the dose order records.

5. The system of claim 4, further comprising:

a data analytics tool executed on a data analytics server in operative communication with the central server for applying the base cube class definition to the multidimensional data set based on the at least one identifier corresponding to a given facility from which the user is accessing the data analytics tool, wherein the data analytics tool is operative to build a data cube based on the applying that limits the data accessible by the user to the subset of the multidimensional data set corresponding to the given facility from which the user is accessing the data analytics tool.

6. The system of claim 5, wherein the data analytics tool is further operative to perform at least one data transformation operation on the subset of the multidimensional data set, wherein the at least one data transformation operation is defined in the base cube class definition.

7. The system of claim 6, wherein the at least one data transformation comprises automatically transcribing a first data field for each given dose order record in the subset with a second data field of the respective ones of the dose order records of the subset.

8. The system of claim 7, wherein the at least one data transformation is applied only to a given type of dose order records.

9. The system of claim 8, wherein the type of dose order records are total parenteral nutrition (TPN) doses, the first data field comprises a dose description field, and the second field comprises a drug name field for the given dose.

10. The system of claim 5, wherein the central server is further operative to invoke another of the data cube class definitions depending from the base cube class definition for application to the subset of the multidimensional data set corresponding to the given facility from which the user is accessing the data analytics tool to generate the dynamically generated report regarding the subset of the multidimensional data set.

11. The system of claim 3, wherein the plurality of data cube class definitions include a parameter indicative of whether data cubes built using the data cube class definitions include protected health information (PHI).

12. The system of claim 11, wherein the parameter is dynamically generated based on at least one dimension of the data cube class definition.

13. The system of claim 1, wherein the local server is operative to receive login information from the user accessing the data analytics tool to initiate a user session, wherein the local server is operative to communicate with the central server to authenticate the user to the central server based on the login information received at the local server, and wherein the central server is operative to populate a session variable related to the user session based on authenticated user login information.

14. The system of claim 13, wherein the data analytics tool further comprises a cryptographic service that is operative to receive a token from a user attempting to access the server, wherein the token is at least partially based on the session variable populated by the central sever, and wherein the cryptographic service is operative to compare the token to available tokens at the central sever to determine if the user is to be granted access to the data analytics tool.

15. The system of claim 14, wherein upon matching the token to one of the available tokens, the token is issued to the user and the corresponding available token is removed from the central server.

16. The system of claim 3, wherein the session variable includes a role definition for the user generated based at least in part on the login information received by the user.

17. The system of claim 16, wherein the role definition includes indications as to the ability of the user in relation to viewing reports, editing reports, viewing cube class definitions, editing cube class definitions, viewing pivot tables, editing pivot tables, viewing dashboards, and editing dashboards.

18. The system of claim 1, further comprising a logging module operative to log user activity in relation to the use of the data analytics tool by the user.

19. The system of claim 18, wherein the logging comprises recording information regarding the user and the usage of the data analytics tool by the user.

20. The system of claim 19, wherein the logging comprises recording the identity of the dynamically generated report presented to the user.

21. The system of claim 20, wherein the logging comprises recording whether the dynamically generated report presented to the user contained protected health information (PHI).

22. The system of claim 1, wherein the multidimensional data set comprises data regarding the identity of doses, data regarding the steps of preparing the doses, data regarding the timing of doses, data regarding errors that occurred during dose preparation, data regarding product waste, data regarding drug usage, data regarding drug therapies administered, data regarding drug interactions, and data corresponding to alerts at a pharmacy workflow management application.

* * * * *